United States Patent [19]

Szmuszkovicz

[11] 4,179,501

[45] Dec. 18, 1979

[54] ANALGESIC N-(2-AMINOCYCLOALIPHATIC-)AZIDOBENZAMIDES

[75] Inventor: Jacob Szmuszkovicz, Kalamazoo, Mich.

[73] Assignee: The Upjohn Company, Kalamazoo, Mich.

[21] Appl. No.: 904,475

[22] Filed: May 10, 1978

Related U.S. Application Data

[62] Division of Ser. No. 741,467, Nov. 12, 1976, Pat. No. 4,098,904.

[51] Int. Cl.² .................. A61K 31/165; C07C 117/00
[52] U.S. Cl. ............................. 424/226; 260/326.4; 260/347.3; 260/349; 544/400; 546/192; 549/59; 549/69
[58] Field of Search ............... 260/349, 558 R, 558 D, 260/558 P, 558 A, 558 S, 326.4, 329 AM, 347.3; 424/324, 226; 546/192; 544/400

[56] References Cited

U.S. PATENT DOCUMENTS

| | | | |
|---|---|---|---|
| 3,373,195 | 3/1968 | Pribyl et al. | 260/558 P X |
| 3,499,033 | 3/1970 | Szmuszkovicz | 260/558 P X |
| 3,510,492 | 5/1970 | Szmuszkovicz | 260/293.79 |
| 3,647,804 | 3/1972 | Rynbrandt et al. | 260/293.63 |
| 3,825,595 | 7/1974 | Roll | 260/558 D X |
| 3,847,982 | 11/1974 | Herr et al. | 260/558 R |
| 3,933,497 | 1/1976 | Singh | 260/349 X |
| 3,975,443 | 8/1976 | Harper et al. | 424/324 X |
| 4,098,904 | 7/1978 | Szmuszkovicz | 424/324 |

OTHER PUBLICATIONS

Stevens et al., Chemical Abstracts, vol. 75, Abst. No. 88275a (1971).

*Primary Examiner*—John D. Randolph
*Attorney, Agent, or Firm*—John T. Reynolds

[57] ABSTRACT

Cis- and trans-N-(2-aminocycloaliphatic)benzamide compounds of the formula

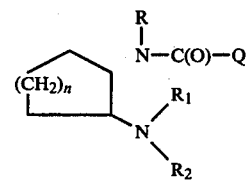

e.g., N-methyl-N-[2-(N-pyrrolidinyl)cyclohexyl]-3,4-dichlorobenzamide, and their pharmaceutically acceptable salts, have been found to have potent analgesic activity, and compositions containing these compounds useful in pharmaceutical dosage unit form for alleviating pain in warm blooded animals, as well as methods for alleviating pain in animals with these compositions. Processes for preparing the compounds are also disclosed.

10 Claims, No Drawings

ANALGESIC N-(2-AMINOCYCLOALIPHATIC)AZIDOBENZAMIDES

This is a division of application Ser. No. 741,467, filed Nov. 12, 1976 now U.S. Pat. No. 4,098,904.

INTRODUCTION

This invention relates to N-(2-aminocycloaliphatic)-benzamides and naphthaylamides which have been found to be useful for relieving pain in animals. More particularly, this invention provides some new N-(2-aminocycloaliphatic)benzamide and naphthamide compositions containing such compounds, methods for using the compounds and compositions, and processes for preparing these compounds.

BACKGROUND OF THE INVENTION

Szmuszkovicz U.S. Pat. No. 3,510,492 discloses and claims some 2-anilino- and 2-anilinomethylcycloalkylamines which are useful as antidiabetic drugs in that they can be administered in low dosages for reducing blood sugar. However, that patent does not teach or suggest the compounds of this invention or the uses which have been found for these compounds. This U.S. Pat. No. 3,510,492 also discloses but does not claim compounds of the formula

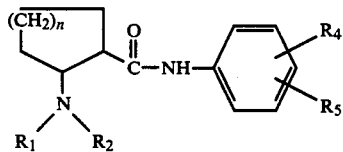

as compounds of structure XV in column 4 thereof, where n is 1 to 4, $R_1$ and $R_2$ are hydrogen, $C_1$ to $C_4$-alkyl, benzyl or $R_1$ and $R_2$ together with the nitrogen to which they are bonded denote a cyclic amino group of the formula

containing 5 to 9 nuclear atoms, and $R_4$ and $R_5$ are hydrogen, $C_1$ to $C_4$-alkyl, $C_1$ to $C_4$-alkoxy, hydroxy, halogen or trifluoromethyl.

Rynbrandt et al., U.S. Pat. No. 3,647,804 discloses some 2-amino-cycloalkane-1-carboxamides and diamines which are said to be useful pharmaceutical drugs because of their hypoglycemic, sedative, and anti-inflammatory activities, but that patent does not suggest the amide types of this invention or the pharmacological activities claimed for the compounds of this invention.

F. Winternitz, et al., in *Bull. Soc. Chim.*, France, 382 (1956) discloses the compound N-(2-dimethylaminocyclohexyl benzamide for the purpose of obtaining a solid derivative of a liquid diamino compound but that article contains no reference to biological data.

N. J. Harper et al., in *J. Chem. Soc.*, 4280 (1964) discloses compounds of the formula

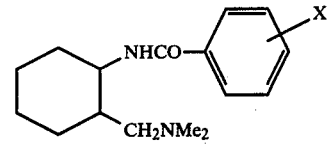

where X is hydrogen, m-fluoro or p-chloro. The stereochemistry of those compounds was not indicated with certainty. In a hot plate test, using pethidine (meperidine) as standard (activity=1) the analgesic activity of these amide compounds where X was p-chloro was 0.22. In the electroshock test it was 34 percent as active as diphenylhydantoin, but all of those compounds lacked activity in the antiamphetamine and antireserpine tests.

R. T. Brittain et al. in the *Brit. J. Pharm.*, 49, page 158 p. (1973) disclose some 1-amino-1-benzoamidomethyl-cyclohexane analgesic compounds of the formulae:

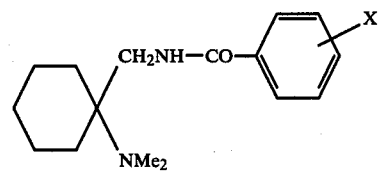

wherein X is hydrogen, 4-F, 3,4-di-Cl, 2-Cl, 3-Cl or 4-Cl.

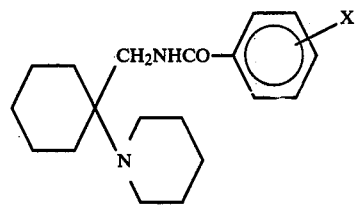

where X is 4-fluoro, 3,4-dichloro or 2-chloro; and

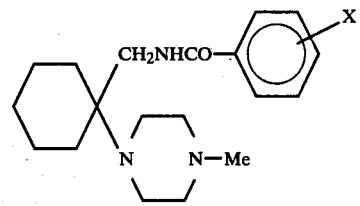

where X is hydrogen or 3,4-dichloro, but those compounds are not 1,2-cyclohexyldiamine derivatives, as are the compounds of this invention.

Those skilled in the analgesic art continue to search for new and useful compounds.

OBJECTS OF THE INVENTION

It is an object of the invention to provide some new N-(2-aminocycloaliphatic)benzamide and -naphthamide compounds which have been found to have a high order of analgesic activity and which are useful in pharmaceutical dosage unit form for alleviating pain in animals, some of which are more potent than morphine and methadone in standard pharmacological laboratory analgesic tests, and some of which exhibit only low apparent physical dependence liability.

Another object of this invention is to provide compositions useful in pharmaceutical dosage unit form for alleviating pain in animals as well as methods for alleviating pain in animals with these compositions.

Other objects, aspects and advantages of this invention will become apparent from reading the remaining specification and claims which follow.

SUMMARY OF THE INVENTION

Briefly, this invention provides some new N-(2-aminocycloaliphatic)benzamides and -naphthamide compounds which have been found to possess a high order of analgesic activity. Compositions of these compounds and a pharmaceutical carrier are useful in dosage unit form for treating pain in animals including humans and the more potent of which are more active than morphine and methadone in pharmacological laboratory tests. In addition, some of these benzamide and naphthamide derivatives also have advantages over morphine and methadone in that they possess low apparent physical dependence liability. Compositions of these compounds and/or their pharmaceutically acceptable salts in an appropriate pharmaceutical carrier are useful in dosage unit form for treating pain in humans and other domestic and commercially valuable warm blooded animals. These compounds and compositions containing them are useful in treatment of the animal to alleviate pain regardless of origin, for example, traumatic pain, bone pain, cancer pain, post surgical pain, homotopic pain, menstrual pain, headache, and the like. The analgesic property of these compounds also makes these compounds useful as antitussives.

DETAILED DESCRIPTION OF THE INVENTION

More particularly, this invention provides some new compounds of the formula

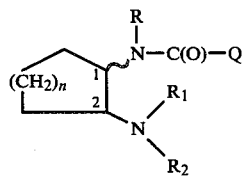

(I)

wherein
the wavy line (∼) at the 1-position of the cycloaliphatic ring denotes cis- or trans-stereoconfiguration of the 1-position substituent with respect to the substituent in position 2 of the same cycloaliphatic ring;

$n$ is 1 to 8 preferably 1 to 4;

R is hydrogen or $C_1$ to $C_3$-alkyl;

$R_1$ and $R_2$, taken separately are hydrogen, $C_1$ to $C_3$-alkyl, or when $R_1$ is hydrogen or $C_1$ to $C_3$-alkyl, $R_2$ is $C_1$ to $C_6$-alkyl, $CH_2CF_3$, —$C_3$ to $C_6$-(allylic)alkenyl, a group of the formula

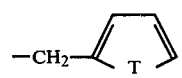

wherein T is —O— or —S—; $C_2$ to $C_5$-hydroxyalkyl, phenyl-$C_2$ to $C_3$-alkyl, $C_3$ to $C_6$-cycloalkyl, $C_3$ to $C_4$-cycloalkylmethyl, or $R_1$ and $R_2$ taken together with the nitrogen to which they are bonded complete a saturated, monocyclic nitrogen heterocyclic ring containing only carbon and nitrogen ring atoms and containing from 3 to 5 carbon atoms, and not more than two nitrogen ring forming atoms; said saturated monocyclic nitrogen heterocyclic rings having 3 to 4 ring carbon atoms permissively being substituted in the 3-position with hydroxy, $C_1$ to $C_3$-alkyl, $C_1$ to $C_3$-alkyloxy, $C_1$ to $C_3$-alkanoyloxy, and said saturated, monocyclic nitrogen heterocyclic rings having 5 ring carbon atoms permissively being substituted in the 3- or 4-position thereof with hydroxy, $C_1$ to $C_3$-alkyl, $C_1$ to $C_3$-alkyloxy, $C_1$ to $C_3$-alkanoyloxy; said saturated monocyclic nitrogen heterocyclic ring including an N-piperazinyl ring, permissively being substituted on the N'-nitrogen with a $C_1$ to $C_3$-alkyl group; and Q is 1-naphthyl, 2-naphthyl or the radical

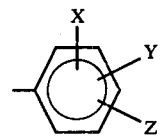

wherein each of X, Y and Z is hydrogen, a halogen having an atomic number of from 9 to 35, cyano, nitro, sulfo (—$SO_3H$), methanesulfonyl (—$SO_2CH_3$), $C_1$ to $C_3$-alkanoyl, hydroxy, trifluoromethyl, $C_1$ to $C_3$-alkyl, $C_1$ to $C_3$-alkyloxy, $C_3$ to $C_6$-(allylic)alkenyloxy, azido, benzoyl, or phenyl, and at least one of X, Y and Z is a substituent other than hydrogen, and when one of X, Y and Z is azido, cyano, phenyl, the remaining X, Y or Z moieties are hydrogen, and when R is hydrogen, and n is 2, and Q is

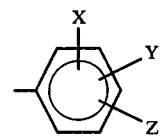

which is disubstituted, X is hydrogen and Y and Z cannot be any combination of $C_1$ to $C_3$-alkyloxy, nitro or hydroxy;

and when R is hydrogen, and n is 2 and Q is

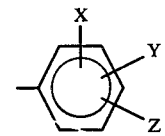

which is monosubstituted X and Y are hydrogen and Z cannot be $C_1$ to $C_3$-alkyloxy, hydroxy, methanesulfonyl, or 3-chloro; and when X is hydroxy, at least one of Y and Z is a halogen having an atomic number of from 9 to 35, or nitro and when N is 1 R must be $C_1$ to $C_3$-alkyl and when one of X, Y, and Z is sulfo (—$SO_3H$) or methanesulfonyl (—$SO_2CH_3$), R is $C_1$ to $C_3$-alkyl; and the pharmaceutically acceptable salts thereof.

In the above formula I compounds, the term "$C_1$ to $C_3$-alkyl" means methyl, ethyl, n-propyl and isopropyl groups. The term $C_1$ to $C_4$-alkyl further includes the butyl group in its various isomeric form. The term $C_1$ to $C_6$-alkyl further includes the pentyl and hexyl groups in their various isomeric forms. The term $C_3$ to $C_6$-(allylic) alkenyl is intended to include the $C_3$ to $C_6$-alkenyl groups which do not have a carbon to carbon double bond adjacent to the alkenyl group bond to nitrogen, and thus includes for example, allyl, 2- butenyl, 2-, pentenyl and 2-, 3-, 4- or 5-hexenyl groups. In the compounds containing the $C_2$ to $C_5$-hydroxyalkyl groups the hydroxy group cannot be on the carbon adjacent to the nitrogen. The cycloalkyl groups include the cyclopropyl, cyclobutyl, cyclopentyl and cyclohexyl radicals. The $C_1$ to $C_3$-alkyloxy groups include the methyloxy, ethyloxy, n-propyloxy and isopropyloxy groups. The $C_1$ to $C_3$-alkanoyloxy groups include formyloxy, acetyloxy and the propionoxy groups. Phenyl-$C_2$ to $C_3$-alkyl groups include 2-phenylethyl and 2- and 3-phenylpropyl groups. Examples of saturated, monocyclic nitrogen heterocyclic ring groups include azetidinyl, pyrrolidinyl, and piperidinyl ring groups.

In the above illustrated compound, (I) the wavy line (bond) at the 1-position of the cycloaliphatic ring will be recognized by those skilled in the chemical art as a symbol to denote the likelihood for cis- and trans-stereochemistry of the 1-position substituent with respect to the substituent in position 2 of the same cycloaliphatic ring. The preferred stereo-configuration of these compounds are those of the trans configuration. It will also be recognized that each of the points of attachment (at positions 1- and 2- in the cycloaliphatic ring) is chiral and thus independently possess a R- or S-configuration. Therefore, these compounds can exist as trans-d, trans-l-, cis-d- and cis-l-optical stereo-isomers of these compounds.

A preferred subgroup of these formula I compounds are those wherein n is 1 to 4; R is $C_1$ to $C_3$-alkyl; $R_1$ and $R_2$ are each $C_1$ to $C_3$-alkyl; and Q is

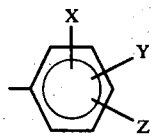

wherein each of X, Y and Z is hydrogen, a halogen having an atomic number of from 9 to 35, cyano, hydroxy, sulfo ($SO_3H$), methanesulfonyl ($-SO_2CH_3$), trifluoromethyl, $C_1$ to $C_3$-alkyl, $C_1$ to $C_3$-alkyloxy, $C_3$ to $C_6$-(allylic)alkenyloxy, azido, benzoyl or phenyl, and at least one of X, Y and Z is a substituent other than hydrogen, and when one of X, Y and Z is cyano, azido, phenyl, $C_3$ the remaining X, Y or Z are hydrogen, and when X is hydroxy, at least one of N and Z is a halogen having an atomic number of from 9 to 35, and the pharmaceutically acceptable salts thereof.

Another preferred sub-group of the above compounds are those where n is 2; R is $C_1$ to $C_3$-alkyl and Q is 2-naphthyl, and the pharmaceutically acceptable salts thereof.

Another preferred sub-group of such compounds are those when n is 2; R is $C_1$ to $C_3$-alkyl, $R_1$ is $C_1$ to $C_3$-alkyl; $R_2$ is $C_1$ to $C_6$-alkyl or $C_3$ to $C_4$-cycloalkylmethyl, and Q is

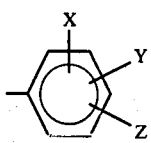

wherein X, Y and Z are as defined above, and their pharmaceutically acceptable salts.

Another preferred sub-group of compounds of formula I are those wherein n is 2; R is $C_1$ to $C_3$-alkyl; $R_1$ is $C_1$ to $C_3$-alkyl; $R_2$ to $C_5$-hydroxyalkyl or $C_3$ to $C_6$-(allylic)alkenyl; and Q is

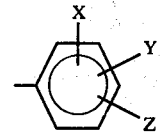

wherein X, Y and Z are as defined above, and their pharmaceutically acceptable salts.

Another preferred sub-group of compounds of formula I above are those wherein n is 2, R is $C_1$ to $C_3$-alkyl; $R_1$ and $R_2$ are $C_2$ to $C_3$-alkyl; and Q is

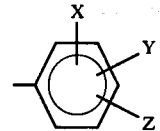

wherein X is hydroxy, Y is an halogen having an atomic number of from 9 to 35 and Z is hydrogen and the pharmaceutically acceptable salts thereof.

Another preferred sub-group of the formula I compounds are those wherein n is 2 to 4; R is $C_1$ to $C_3$-alkyl; $R_1$ and $R_2$ are taken together with the nitrogen to which they are bonded to complete a saturated, monocyclic nitrogen heterocyclic ring group containing only carbon and nitrogen ring atoms and containing from 3 to 5 carbon atoms, and not more than two nitrogen ring forming atoms, said saturated, monocyclic nitrogen heterocyclic rings having 3 to 4 ring carbon atoms permissively being substituted in the 3-position with hydroxy, $C_1$ to $C_3$-alkyl, $C_1$ to $C_3$-alkyloxy, $C_1$ to $C_3$-alkanoyloxy, and said saturated, monocyclic nitrogen heterocyclic rings having five ring carbon atoms permissively being substituted in the 3- or 4-position thereof with hydroxy, $C_1$ to $C_3$-alkyl, $C_1$ to $C_3$-alkyloxy, $C_1$ to $C_3$-alkanoyloxy; and Q is

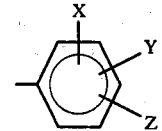

wherein X, Y and Z are defined above, and the pharmaceutically acceptable salts thereof.

Examples of the above preferred compounds include

N-methyl-N-[2-(N',N'-dimethylamino)cyclohexyl]-4-azidobenzamide,

N-methyl-N-[2-(N',N'-dimethylamino)cyclohexyl]-2-methyl-4-allyloxybenzamide,

N-methyl-N-[2-(N',N'-dimethylamino)cyclohexyl]-4-cyanobenzamide,

N-methyl-N-[2-(N',N'-dimethylamino)cyclopentyl]-3,4-dichlorobenzamide,

N-methyl-N-[2-(N',N'-dimethylamino)cyclohexyl]-4-methoxybenzamide,

N-methyl-N-[2-(N',N'-dimethylamino)cyclohexyl]-3-bromo-4-hydroxybenzamide,

N-methyl-N-[2-(N'-methyl-N'-cyclobutylmethylamino)cyclohexyl]-4-trifluoromethylbenzamide,
N-methyl-N-[2-(N',N'-dimethylamino)cyclohexyl]-3-bromo-4-methoxybenzamide,
N-methyl-N-{2-[N'-methyl-N'-(3-methyl-2-butenyl)amino]cyclohexyl}-4-trifluoromethylbenzamide,
N-methyl-N-[2-(N',N'-dimethylamino)cycloheptyl]-4-trifluoromethylbenzamide,
N-methyl-N-[2-(N'-methyl-N'-butylamino)cyclohexyl]-3,4-dichlorobenzamide,
N-methyl-N-[2-(N'-pyrrolidinyl)cyclohexyl]-4-trifluoromethylbenzamide,
N-methyl-N-{2-[N'-methyl-N'-(2-hydroxyethyl)amino]cyclohexyl}-4-trifluoromethylbenzamide,
N-methyl-N-[2-(N',N'-dimethylamino)cycloheptyl]-4-azidobenzamide,
N-methyl-N-[2-(N',N'-dimethylamino)cyclohexyl]-2-naphthamide, and the pharmaceutically acceptable salts thereof.

These formula I compounds can be prepared by reacting the appropriate 1,2-cycloaliphatic diamine of the formula

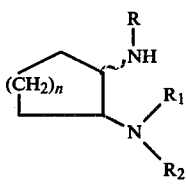
(II)

with an aracyl imidazole of the formula

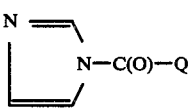
(III)

wherein n, R, $R_1$, $R_2$ and Q are as defined above, or with an acyl halide of the formula

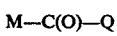

M—C(O)—Q       (IV)

wherein M is chloride or bromide and Q is as defined above, in an organic solvent for the reactants, preferably in a cyclic ether solvent such as tetrahydrofuran (THF) or dioxane, or the like, until the compound of formula I is produced. The reactants, (II) and (III) or (II) and (IV) can be mixed in substantially equimolar proportions to effect formation of the desired product (I), but if one of the reactants (II), (III) and (IV) is more expensive than the other, it is sometimes preferred to use a stoichiometric excess of the less expensive reactant to ensure that substantially all of the more expensive reactant is consumed in the reaction. The reaction will proceed at ambient temperature for most combinations of reactants, but for some combinations of reactants, variations from the initial to final reaction conditions may vary between about −25° C. and reflux temperature of the mixture depending on the reactivity of the reactants, the desired reaction time, the solvent being used, the molar proportions, and similar factors of concern to the chemist operating the process.

When the reaction has proceeded to substantial completion, the product (I) can be recovered from the reaction by known procedures. For example, the reaction mixture can be evaporated, under vacuum, if desired, to remove solvent and other volatiles, leaving the product, often as an oil, mixed with a small amount of solvent and any unreacted or unvolatilized starting materials. This residual mixture can be taken up in a solvent such as ethyl ether, washed with salt solution such as saturated sodium bicarbonate and dried over a water absorbent such as sodium sulfate or magnesium sulfate and then evaporated to leave the more pure product as an oil or crystalline material. Addition of hydrochloric acid (HCl gas) or other economical acid such as sulfuric, maleic, naphthalenesulfonic, p-toluenesulfonic, oxalic acids in ethyl ether converts the oily product to the corresponding salt form which crystallizes more readily than the free amine form of the product. The amine salt products can be recrystallized from solvent mixtures such as $C_1$ to $C_3$-alkanol/di-$C_1$ to $C_3$-alkyl ether, e.g., methanol/diethyl ether, to give more readily handled crystalline forms of the product as the amine salts. Examples of such procedures are described in the detailed examples.

The trans-1,2-diamines (IIa), which can be used as starting materials to prepare compounds of this invention can be prepared by procedures known in the art. For example, amines of the formula

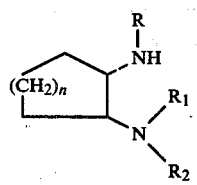
(IIa)

wherein R is $C_1$ to $C_3$-alkyl, and
$R_1$ and $R_2$, as defined above, except that when $R_1$ and $R_2$ are taken separately, $R_1$ and $R_2$ are not hydrogen, benzyl or any hydrocarbon group with carbon to carbon unsaturation, can be prepared by reacting the respective 1,2-cycloalkane epoxide with the amine $HNR_1R_2$ wherein $R_1$ and $R_2$ are as defined immediately above to form the 2-aminocycloalkanol of the formula

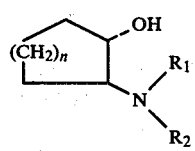
(V)

wherein n, $R_1$ and $R_2$ are defined immediately above, and then reacting this aminocycloalkanol intermediate (V) first with a $C_1$ to $C_3$-alkanesulfonyl halide, e.g., with methanesulfonyl chloride, and then with an α-benzylamine of the formula $C_6H_5CH_2NHR$ where R is as generally defined above, to form a compound of the formula

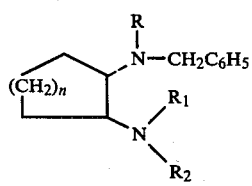
(VI)

wherein n, $R_1$ and $R_2$ are as defined hereinabove, and then hydrogenolyzing this diamine (VI) with hydrogen in the presence of a palladium on charcoal catalyst and acid to remove the benzyl group and to form the trans-diamine starting material (IIa).

Similarly, trans-1,2-cycloaliphatic amines IIa can be prepared by reacting a bicyclic aziridine of the formula

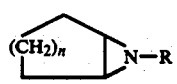

(VII)

wherein R is hydrogen or $C_1$ to $C_3$-alkyl with an amine of the formula $HNR_1R_2$ wherein $R_1$ and $R_2$, taken separately, are hydrogen, $C_1$ to $C_3$-alkyl, or when $R_1$ is hydrogen $R_2$ is $C_1$ to $C_6$-alkyl, $-CH_2CF_3$, $C_3$ to $C_6$-(allylic) alkenyl, $C_2$ to $C_5$-hydroxyalkyl, $C_3$ to $C_6$-cycloalkyl-, $C_3$ to $C_4$-cycloalkylmethyl or $R_1$ and $R_2$, taken together with the nitrogen to which they are bonded, complete a saturated monocyclic nitrogen heterocyclic ring containing only carbon and nitrogen ring atoms and from 3 to 5 ring carbon atoms, such saturated heterocyclic ring moieties having 3 to 4 ring carbon atoms permissively being substituted in the 2- or 3-position with hydroxy, $C_1$ to $C_3$-alkanoyloxy, $C_1$ to $C_3$-alkyloxy, or $C_1$ to $C_3$-alkyl, and said saturated heterocyclic rings having five ring carbon atoms, permissively being substituted in the 3- or 4-positions with hydroxy, $C_1$ to $C_3$-alkanoyloxy, $C_1$ to $C_3$-alkyloxy, or $C_1$ to $C_3$-alkyl, respectively, to form the diamine starting material (IIa). This amine—plus—aziridine diamine synthesis method is applicable whether the amino group in the 2-position of the saturated cycloaliphatic ring moiety is to be a tertiary, secondary or a primary amino group, and this method is imperative when this 2-amino ($-NR_1R_2$) group is to have attached thereto at least one $C_3$ to $C_6$-(allylic) alkenyl group.

The trans 1,2-cycloaliphatic diamine starting material (IIa) is then reacted with the aracyl imidazole (III) or with the acyl halide (IV) to form the trans products of this invention (Ia). For example, if it is desired to prepare a trans compound of formula I wherein $R_2$ is a $C_3$ to $C_6$-(allylic)alkenyl one process route which can be used would comprise (a) reacting an amine of the formula $HNR_1R_2$ where $R_1$ is as defined above when $R_2$ is $C_3$ to $C_6$-allylic alkenyl with a bicyclic aziridine of formula VII, above, to form the trans diamine of the formula

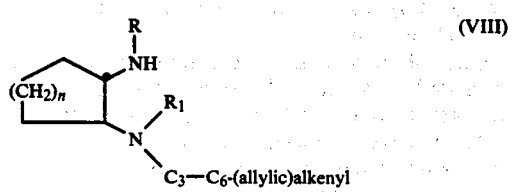

(VIII)

and then (b) react this trans-1,2-cycloaliphatic diamine (VIII) with the aracyl imdazole (III) or the acyl halide (IV) in an organic solvent for a time sufficient to form the trans compound of formula Ia wherein $R_2$ is the $C_3$ to $C_6$-(allylic)alkenyl group.

The cis-1,2-diamine starting materials (IIb) can be prepared by reacting an unsaturated cycloaliphatic amine of the formula

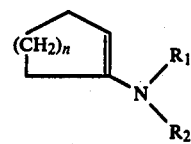

(IX)

where n, $R_1$ and $R_2$ are as generally defined above, with an alkyl (preferably $C_1$ to $C_3$-alkyl) or benzyl chloroformate and then with hydrogen in the presence of a catalyst such as platinum dioxide to form the alkyl or benzyl 2-amino-1-cycloaliphatic carboxylate of the formula

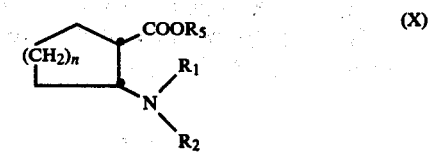

(X)

where $R_5$ is the alkyl or benzyl group from the chloroformate ester and n, $R_1$ and $R_2$ are as described above. This amino ester (X) can then be hydrolyzed with mineral acid or alkali metal base when $R_5$ is alkyl, or hydrogenolyzed in the presence of palladium on carbon catalyst when $R_5$ is benzyl, to form the amino-acid of the formula

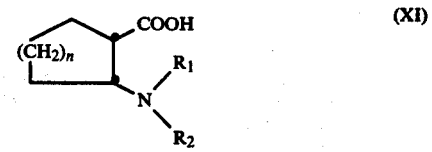

(XI)

wherein n, $R_1$ and $R_2$ are as defined above. In these structures the double heavy dots (•) at positions 1 and 2 of the cycloaliphatic ring denote cis-stereoconfiguration to each other of the substituents of the 1- and 2-positions to each other. One such dot denotes a trans configuration.

Electrophilic addition to enamines to give the 2-carboxy-substituted enamines is known in the art; see, e.g., A. G. Cook, ed., "Enamines: Synthesis, Structure and Reactions", M. Dekker, New York, 1969.

This amino acid (XI) can then be converted to the cis-diamine (IIb) by a known Curtius reaction (T. Curtius, J. Prakt. Chem., [2] 50, 274 (1894); See also Merck Index, Eighth Edition, (1968), p. 1156) and which can be used as a cis-starting material

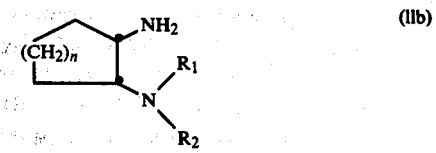

(IIb)

wherein n, $R_1$ and $R_2$ are as defined above.

The above unsaturated cycloaliphatic amine intermediates (IX) are prepared by reacting the corresponding cycloaliphatic ketone of the formula

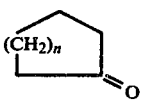
(XII)

with an amine of the formula $HNR_1R_2$ in the presence of an acid such as titanium tetrachloride. The use of titanium tetrachloride in the preparation of enamines has been described in *J. Organic Chemistry*, 32, p. 213 (1967).

When it is desired to prepare a cis-product containing an N-methyl group in the 1-position of the 1,2-cycloaliphatic diamine ($R=CH_3$) the cis-diamine starting material (IIb) is treated with an alkyl formate to form a compound of the formula

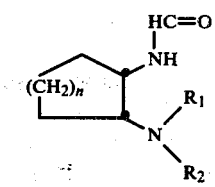
(XIII)

which compound XIII can then be reduced, e.g., with chemical reducing agents such as lithium aluminum hydride to form the N-methylated cis-1,2-diamine of the formula XIVa

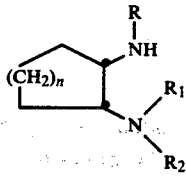

(XIVa) R = $CH_3$
(XIVb) R = $C_2$ to $C_3$-alkyl

The primary cis-1,2-diamine (IIb) and the secondary cis-1,2-diamine (XIVa) can then be treated according to the process of this invention with the aracyl imidazole (III) or with the acyl halide (IV) as described above to prepare cis-compounds (Ib) of this invention. When the cis compound (Ib) of this invention is to have an alkyl group other than methyl in the R position, the primary cis-1,2-diamine (IIb) can be reacted with an alkanoyl halide, e.g., with a $C_2$ to $C_3$-alkanoyl chloride or bromide, and then with a chemical reducing agent such as lithium aluminum hydride to form the secondary $N-C_2$ or $C_3$-alkyl cis-1,2-diamine starting material of the formula (XIVb) wherein the R group position would be a higher alkyl group, preferably an ethyl or propyl group. Then, this secondary N-alkyl cis-1,2-diamine (XIVb) would be reacted with the aracyl imidazole (III) or the acyl halide (IV) to form the cis product (Ib) of this invention. When it is desired that the cis-product of this invention have $C_3$ to $C_6$-allylic alkenyl group in the $R_2$ position, the primary cis-1,2-diamine (IIb) with $R_2$ as benzyl (XV) is prepared from the ketone XII as described above by reacting with an N-benzyl-N-$R_1$ amine.

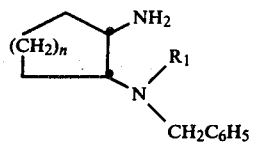
(XV)

This diamine (XV) is then hydrogenated in the presence of palladium on carbon catalyst to remove the benzyl group and form the cis-1,2-diamine of the formula

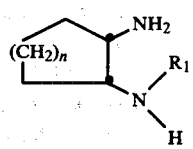
(XVI)

The cis-1,2-diamine (XVI) is then reacted with the selected aracyl imidazole (III) or acyl halide (IV) to form the cis-amide of the formula

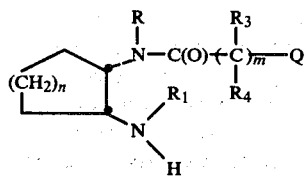
(Ib₁)

which amide (Ib₁) is also a useful analgesic in pharmaceutical product form, but which is primarily of interest for use as an intermediate to form the cis-products of this invention (Ib) wherein $R_2$ is an allylic $C_3$ to $C_6$-alkenyl group. For this purpose the intermediate product (Ib₁) is reacted with an allylic alkenyl halide, preferably the bromide or iodide to form the cis-products of this invention (Ib) wherein $R_2$ is $C_3$ to $C_6$-(allylic) alkenyl.

Procedures for preparing the aracyl imidazoles (III) and acyl halide (IV) reactants used to form compounds of this invention are known in the art. See, for example, R. B. Wagner and H. D. Zook, *Synthetic Organic Chemistry*, 1953, John Wiley and Sons, Chapter 17, pp. 546 et seq. The aracyl imidazole can be prepared in situ by reacting carbonyldiimidazole with the acid of the formula HO—C(O)—Q     (IIIa)

in an organic solvent. Other carbodiimides such as dicyclohexylcarbodiimide can be used in place of the carbonyldiimidazole.

Acid addition salts of these amino-amides (I) can be prepared by reacting a Formula I free base with a stoichiometric amount of an acid, such as hydrogen chloride, hydrogen bromide, hydrogen iodide, sulfuric acid, phosphoric acid, acetic acid, lactic acid, citric acid, succinic acid, benzoic acid, salicyclic acid, pamoic acid, cyclohexanesulfamic acid, methanesulfonic, naphthalenesulfonic, p-toluenesulfonic, maleic, fumaric, oxalic acids and the like. The reaction can be carried out in aqueous or organic liquid solvent non-aqueous media such as diethyl ether, ethyl acetate, and the like. Non-aqueous media are preferred.

On occasion the compounds (I) or their acid addition salts in their crystalline state are isolated as solvates, e.g., with a discrete quantity of solvent, e.g., water, methanol, and the like, associated physically, and thus removable without effective alteracation of the chemical entity per se.

Examples of additional useful compounds of formula I of this invention include the following compounds, preferably in the trans configuration:

N-[2-(N',N'-dimethylamino)cyclohexyl]-3,4-dichlorobenzamide,
N-[2-(N'-methyl-N'-allylamino)cyclohexyl]-3,4-dichlorobenzamide,
N-methyl-N-[2-(N',N'-dimethylamino)cyclohexyl]-4-bromobenzamide,
N-methyl-N-[2-(N'-methyl-N'-2-phenylethylamino)cyclohexyl]-4-trifluoromethylbenzamide,
N-methyl-N[2-(N'-methyl-N'-cyclopropylmethylamino)cyclohexyl]-4-trifluoromethylbenzamide,
N-methyl-N-[2-(1-pyrrolidinyl)cyclohexyl]-4-trifluoromethylbenzamide,
N-methyl-N-[2-(N'-methyl-N'-cyclopropylmethylamino)cyclohexyl]-4-bromobenzamide,
N-methyl-N-[2-(N',N'-dimethylamino)cyclohexyl]-3,4-dichlorobenzamide,
N-methyl-N-[2-(N-pyrrolidinyl)cyclohexyl]-4-sulfobenzamide,
N-methyl-N-[2-(N',N'-dimethylamino)cyclopentyl]-3,4-dichlorobenzamide,
N-methyl-N-[2-(N',N'-dimethylamino)cyclohexyl]-1-naphthamide,
N-methyl-N-[2-(N,N-dimethylamino)cycloheptyl]-4-azidobenzamide,
N-[2-[N'-methyl-N'-(2-phenylethyl)amino]cyclohexyl]-3,4-dichlorobenzamide,
N-[2-(N'-methyl-N'-ethylamino)cyclohexyl]-3,4-dichlorobenzamide,
N-methyl-N-[2-(N'-methyl-N'-allylamino)cyclohexyl]-3,4-dichlorobenzamide,
N-[2-(N',N'-dimethylamino)cyclohexyl]-4-chlorobenzamide,
N-methyl-N-[2-(N',N'-dimethylamino)cyclohexyl]-3,4-difluorobenzamide,
N-[2-(N',N'-dimethylamino)cyclohexyl]-4-bromobenzamide,
N-methyl-N-[2-(N',N'-dimethylamino)cyclohexyl]-4-bromobenzamide,
N-methyl-N-[2-(N'-allyl-N'-methylamino)cyclohexyl]-4-bromobenzamide,
N-[2-(N',N'-dimethylamino)cyclohexyl]-4-trifluoromethylbenzamide,
N-methyl-N-[2-(N',N'-dimethylamino)cyclohexyl]-4-trifluoromethylbenzamide,
N-ethyl-N-[2-(N',N'-dimethylamino)cyclohexyl]-4-trifluoromethylbenzamide,
N-methyl-N-[2-(N'-methyl-N'-propylamino)cyclohexyl]-4-trifluoromethylbenzamide,
N-[2-(N'-methyl-N'-allylamino)cyclohexyl]-4-trifluoromethylbenzamide,
N-methyl-N-[2-(N'-methyl-N'-allylamino)cyclohexyl]-4-trifluoromethylbenzamide,
N-methyl-N-{2-N'-(1-pyrrolidinyl)cyclohexyl}-4-trifluoromethylbenzamide,
N-[2-(N',N'-dimethylamino)cyclohexyl]-4-trifluoromethylbenzamide,
N-methyl-N-[2-(N',N'-dimethylamino)cyclopentyl]-4-trifluoromethylbenzamide,
N-[2-(N,N-dimethylamino)cyclohexyl]-4-nitrobenzamide,
N-methyl-N-[2-(N',N'-dimethylamino)cyclohexyl]-4-nitrobenzamide,
N-methyl-N-[2(N',N'-dimethylamino)cyclohexyl]-3-methoxy-4-nitrobenzamide,
N-methyl-N-[2-(N',N'-dimethylamino)cyclohexyl]-3-hydroxy-4-nitrobenzamide,
N-[2-(N,N'-dimethylamino)cyclohexyl]-3-trifluoromethylbenzamide,
N-methyl-N-[2-(N',N'-dimethylamino)cyclohexyl]-3-methoxybenzamide,
N-methyl-N-[2-(N',N'-dimethylamino)cyclohexyl]-4-methanesulfonylbenzamide,
N-methyl-N-[2-(N',N'-dimethylamino)cyclohexyl]-4-acetoxybenzamide,
N-[2-(N',N'-dimethylamino)cyclohexyl]-3-chlorobenzamide,
N-[2-(N',N'-dimethylamino)cyclohexyl]-2,4-dichlorobenzamide,
N-methyl-N-[2(N',N'-dimethylamino)cyclohexyl]-3,4,5-trimethoxybenzamide,
N-[2-(N',N'-dimethylamino)cycloheptyl]-4-trifluoromethylbenzamide,
N-methyl-N-[2-(N',N'-dimethylamino)cycloheptyl]-4-trifluoromethylbenzamide,
N-[2-(N',N'-dimethylamino)cyclooctyl]-4-trifluoromethylbenzamide,
N-methyl-N-[2-(N',N'-dimethylamino)cyclooctyl]-4-trifluoromethylbenzamide,
N-propyl-N-[2-(N-piperidinyl)cyclononyl]-3,4-dibromobenzamide,
N-ethyl-N-[2-(N',N'-diethylamino)cyclodecyl]-4-azidobenzamide,
N-methyl-N-[2-(N-methyl-N-allylamino)cyclododecyl]-3,4-dichlorobenzamide, and the like, and the pharmaceutically acceptable salts thereof.

This invention also relates to compositions containing a formula I compound as an active ingredient in a pharmaceutical carrier. The compositions are useful in pharmaceutical dosage unit forms of the formula I compounds for local (topical) and systemic administration (oral, rectal and parenteral administration form) for treating and alleviating pain in humans and valuable animals, including dogs, cats, horses and other commercially valuable and domestic animals. The term "dosage unit form" as used in this specification and in the claims refers to physically discrete units suitable as unitary dosages for mammalian subjects, each unit containing a predetermined quantity of the essential active ingredient compound of this invention calculated to produce the desired effect in combination with the required pharmaceutical means which adapt the said ingredient for topical or systemtic administration. The specifications for the novel dosage unit forms of this invention are dictated by and directly dependent on the physical characteristics of the essential active ingredient and the particular effect to be achieved in view of the limitations inherent in the art of compounding such an essential active material for beneficial effects in humans and animals as disclosed in detail in this specification under preferred embodiments, these being features of the present invention. Examples of suitable dosage unit forms is accordance with this invention are tablets, capsules, orally administered liquid preparations in suitable liquid vehicles, sterile preparations in suitable liquid vehicles for intramuscular and intravenous administration, suppositories, and sterile dry preparations for the extemporaneous preparation of sterile injectable preparations in a suitable liquid vehicle. Suitable solid diluents or carriers for the solid oral pharmaceutical dosage unit forms are selected from the group consisting of lipids, carbohydrates, proteins and mineral solids, for example, starch, sucrose, lactose, kaolin, dicalcium phosphate, gelatin, acacia, corn syrup, corn starch, talc and the like. Capsules both hard and soft are filled with composition of these amino amide ingredients in combination with suitable diluents and excipients, for example, edible oils, talc, calcium carbonate and the like and also calcium stearate. Liquid preparations for oral administration are prepared in water or aqueous vehicles which advantageously contain suspending agents, for example, methylcellulose, acacia, polyvinylpyrrolidone, polyvinyl alcohol and the like. In the case of injectable forms, the injectable formulation must be sterile and must be fluid to the extent that easy syringeability exists. Such preparations must be stable under the conditions of manufacture and storage, and ordinarily contain in addition to the basic solvent or suspending liquid, preservatives in the nature of bacteriostatic and fungistatic agents, for example, parabens, chlorobutanol, benzyl alcohol, phenol, thimerosal, and the like. In many cases it is preferable to include osmotically active agents, for example, sugars or sodium chloride in isotonic concentrations. Carriers and vehicles include vegetable oils ethanol, polyols, for example, glycerol, propylene glycol, liquid polyethylene glycol, and the like. Any solid preparations for subsequent extemporaneous preparation of sterile injectable preparations are sterilized, preferably by exposure to a sterilizing gas, for example, ethylene oxide. The aforesaid carriers, vehicles, diluents, excipients, preservatives, isotonic agents and the like constitute the pharmaceutical means which adapt the preparations for systemic administration.

The pharmaceutical dosage unit forms are prepared in accordance with the preceding general description to provide from about 0.5 to about 350 mg. of the essential active ingredient per dosage unit form, which as aforesaid may be in the form of a solid, semi-solid, topical, oral, or rectal preparation, a liquid oral preparation, an injectable preparation, including liquid preparations and solid dry preparations for extemporaneous reconstitution to a liquid injectable preparation. The amount of the essential active ingredient provided in the pharmaceutical dosage unit forms is that amount sufficient to obtain analgesic and/or narcotic antagonist effects within the aforesaid effective non-toxic range. Expressed otherwise an amount of the essential active ingredient is provided to a recepient within a range from about 0.01 mg. per kg. to about 5 mg. per kg. of body weight of the recipient. Preferred dosages for most applications are 0.05 to 2.0 mg. per kg. of body weight. In a topical semi-solid ointment formulation the concentration of the active ingredient may be 0.1 to 10 percent, preferably 0.5 to 5 percent in a carrier such as a pharmaceutical cream base.

The useful pharmaceutical dosage unit forms of these compounds in pharmaceutical formulations is preferably adapted for systemic administration to obtain analgesic and/or narcotic antagonist effects comprising an effective, nontoxic amount of a compound according to Formula I or as its pharmacologically acceptable salt. Further the invention relates to methods of obtaining analgesic effects in mammals, for example, humans and valuable warm-blooded animals such as dogs, cats, horses and other commercially valuable animals, by administering systemically to the mammals the aforesaid pharmaceutical dosage unit forms supplying an effective, nontoxic amount for analgesic and narcotic antagonist effects. These compounds have an advantage, to a greater or lesser extent, depending upon the particular compound, of having lower physical dependence liability than known analgesic compounds such as morphin and methadone, as shown by evaluation of representative compounds and those standard analgesic drug compounds in various pharmacological test procedures which measure relative degrees of analgesia and the physical dependence liability of the test compounds in standard laboratory test animals.

Representative examples of these formula I compounds, have $ED_{50}$ values ($\pm 95$ percent confidence limit) of less than about 75 mg./kg. s.c. (subcutaneous administration) in standard laboratory animal analgesic tests such as the tail flick, pinch and writhing tests, and the more potent of them have $ED_{50}$ values of less than 10 mg./kg. (s.c.) in these tests, while at the same time giving quite high values (greater than 100 mg./kg. s.c.) in the naloxone jumping tests and possessing only low to moderate apparent physical dependence liability as compared to commercial analgesics used as standards. The procedures used to determine these properties of these new compounds were essentially those of Way et al., (Way, E. L. et al., "Simultaneous Quantitative Assessment of Morphine Tolerance and Physical Dependence", *J. Pharmacol. Exp. Therm.* 167, pp 1–8 (1969)) and Sealens et al., (Sealens, J. K. et al., "The Mouse Jumping Test-A Simple Screening Method to estimate the Physical Dependence Capacity of Analgesics", *Arch. Int. Pharmacodyn.* 190, pp. 213–218 (1971). Statistical effective doses ($ED_{50}$ values) and 95 percent confidence limits were calculated by the method of Spearman and Karber (Finney, D. J., "Statistical Methods in Biological Assay", Hoofner Publ., (1952).

For example, representative preferred compounds of formula I give low analgesic $ED_{50}$ values (less than about 10 mg. of test compound/kg. of animal body weight, subcutaneous administration route in standard laboratory animal tests) while at the same time possessing quite high $ED_{50}$ values (greater than 250 mg./kg., s.c.) in the naloxone jumping test, evidencing substantial freedom from apparent physical dependence liability. In contrast, known analgesic drugs such as morphine and methadone exhibit analgesic $ED_{50}$ values or less than 2 mg./kg., s.c., respectively, in these standard analgesic tail flick, pinch and writhing tests, but are known to have high apparent physical dependence liability effects, and this is confirmed by their (morphin and methadone) having relatively low naloxon jumping $ED_{50}$ values ranging from 12 to 30 mg./kg. s.c.. Although other representative compounds of this invention have analgesic potencies somewhat less than the preferred compounds, having analgesic activity $ED_{50}$ values up to about 70 mg./kg. s.c. in these standard tests, the preferred compounds are characterized by having only low to moderate apparent physical dependence liability.

Of the preferred compounds we estimate that the N-alkyl-N-[2-di-lower alkylamino)cyclopentyl]-3,4-dihalo(Cl, Br, or F)benzamides have about one-third the analgesic potency of morphine but have very low apparent physical dependencies; the N-alkyl-N-[2-di-lower alkylamino-; alkyl aralkyl amino and the N-heterocyclic)cyclohexyl]azido, trifluoromethyl and sulfonyl substituted benzamides have up to about three times the potency of morphine and low apparent physical dependence liability; the N-alkyl-N-[2-(di lower alkylamino)cycloheptyl]azidobenzamides have about equivalent analgesic potency compared to morphine and low apparent physical dependence liability. On the other hand, of the above preferred formula I compounds many of the N-alkyl-N-[2-(di-loweralkylamino; alkyl, allylamino; and alkyl cycloalkylalkylamino)cyclohexyl]-trifluoromethyl-, dihalo- and halo, hydroxy benzamides show two to three times the potency of morphine but they also have relatively high apparent physical dependence liability potential.

If desired the formula I compounds of this invention can be resolved into their respective d- and l-optical isomers by methods known in the art. In this case, the optical resolution can be done by at least two different routes. The resulting agents by either route are any of the known resolving agents such as optically active camphorsulfonic acid, bis-o-toluyltartaric acid, tartaric acid, and diactyl tartaric acid which are commercially available and which are commonly used for resolution of amines (bases), as for example in *Organic Synthesis*, Coll. Vol. V., p. 932 (1973), resolution of R-(+) and S-(−)-α-phenylethylamine with (+)-tartaric acid.

By the first method for resolving the compounds of this invention, for example, one of the aminoamide compounds can be converted into its optically active disstereomeric salts by reaction with an optically active acid—examples mentioned above—in a manner standard in the isomer resolution art. These diastereomeric salts can then be separated by conventional means such as differential crystallization. Diastereomeric salts have different crystallization properties, which are taken advantage of in this separation. On neutralization of each diastereomeric salt with aqueous base the corresponding optically active enantiomers of the free amino amide can be obtained, each of which can subsequently and separately be converted as hereinafter described in the examples to the desired acid addition salt.

By the second method, which in the case of some of these compounds is preferred, the formula I compounds can be made into their respective d- and l-isomers, by first resolving each cis- or trans-1,2-cycloaliphatic unsymmetrically substituted diamine into its respective d- or l-isomers by treatment with the resolving agent, crystallization, separation and regeneration of the respective trans-d-diamine, trans-l-diamine, or the cis-d-diamine and cis-l-diamine, and then reacting the respective resolved diamine starting material with the desired aracyl imidazole (III) or the acyl halide (IV) to form the respective cis or trans, d- or l- compound of formula I, which can then be converted to any desired pharmaceutically acceptable acid addition salt by procedures exemplified hereinafter.

Examples of Preparations of trans-Cycloaliphatic Diamine Starting Materials

Procedure I

A. trans-2-Methylaminocyclohexanol

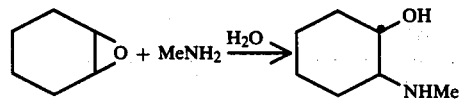

Cyclohexene oxide (196.28 g., 2 mole) was added during 30 minutes to 40% aqueous methylamine (466 ml., 6 moles) with stirring. The temperature was from 25° to 27° during this addition. During the following 45 minutes, the temperature rose to 55° and was kept at 50° to 58° by occasional cooling. It was stirred at room temperature for 18 hours, then heated on the steam bath for 2 hours, cooled and saturated with solid sodium hydroxide (NaOH). The mixture was extracted well with ether, the extract was dried over magnesium sulfate (MgSO4) and evaporated through a 9" Vigreux. Distillation at 13 mm gave 241.9 g. (97% yield) of the title aminocyclohexanol b.p. 100°-101°. IR: OH 3300; N-alkyl 2800, 2660; C—O 1070 cm$^{-1}$.

nmr in CDCl3 (100 MHz) was in accord. Mass spectrum M+ 129.

This titled compound was reported by Mousseron et al., Bull. Soc. Chim. Fr., 850 (1947) by the reaction of cyclohexene oxide with methylamine for 2 hours at 110°, b.p. 108°-109° (17 mm); HCl salt, m.p. 114°-115°.

B. N-Methyl-7-azabicyclo[3.1.0]heptane

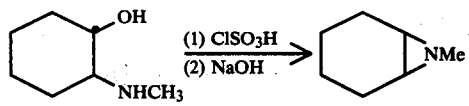

Chlorosulfonic acid (162.9 g., 1.4 mole) was added dropwise during 70 minutes to a solution of trans-2-methylaminocyclohexanol (179.7 g., 1.39 mole) keeping the temperature at 5° to 10°. The thick mixture was stirred for 1.5 hours at room temperature (raising the stirrer made agitation possible). Ether was decanted, and the product washed once with 300 ml. of ether by decantation. It was then cooled in ice, treated with a solution of 206 g. sodium hydroxide in 1 liter of H2O (cautiously at first). The mixture was then distilled, while adding H2O from a dropping funnel to keep the volume constant. About 600 ml. of distillate was collected during 4 hours. The distillate was saturated with solid sodium hydroxide, and extracted with ether (8×100 ml.). The extract was dried (magnesium sulfate) and ether was distilled through a 8" glass helices column. The titled product boiled at 70°-72° (97 mm); 73 g. (47% yield).

nmr (nuclear magnetic resonance) in CDCl3 (100 MHz) was in accord. Mass spectrum M+ 111. ir (infrared): CH 2960, 2940, 2860; N-alkyl 2760; C-N 1110; other 760 cm$^{-1}$.

This compound was prepared before by T. Taguchi and M. Eto, *JACS*, 80, 4075 (1958) in 37% yield by the procedure of Paris and Fanta for the synthesis of 7-azabicyclo[3.1.0]heptane; O. E. Paris and P. E. Fanta, *JACS*, 74, 3007 (1952) used carbon tetrachloride (CCl4) in the above mentioned procedure and steam distilled the product after refluxing with alkali for 2 hours.

C. trans-N,N-Dimethyl-1,2-cyclohexanediamine

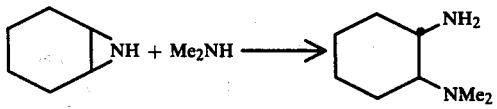

The starting 7-azabicyclo[4.1.0]heptane was best prepared according to the procedure of D. E. Paris and P. E. Fanta, *JACS*, 74, 3007 (1952) from trans-2-aminocyclohexanol with chlorosulfonic acid, followed by heating with aqueous sodium hydroxide. For the reaction with dimethylamine the procedure described in *Bull. Soc. Chim.*, France, 382 (1956) was followed.

A mixture of 7-azabicyclo[4.1.0]heptane (12 g.; 0.124 mole), 40 ml. of aqueous dimethylamine and 0.2 g. of ammonium chloride (NH4Cl) was stirred and heated on the steam bath for 18 hours and partly evaporated at room temperature in vacuo. Sodium hydroxide (NaOH) was added and the mixture extracted with ether. The extract was dried (MgSO4) and evaporated. Distillation at 16 mm gave 8.1 g. (46% yield) of the titled compound as a colorless oil. nmr in CDCl2 (100 MHz) was in accord. Mass spectrum (M-8705) M+142.

This compound was also prepared from trans-2-dimethylaminocyclohexanol by reaction with chlorosulfonic acid followed by ammonia, according to the procedure in Helv. Chim. Acta, 34, 1937 (1951).

Procedure II trans-N,N'-Dimethyl-N-allyl-1,2-cyclohexanediamine

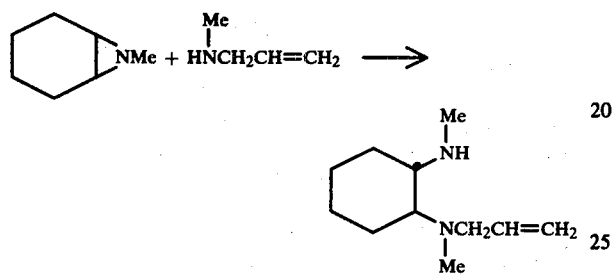

A mixture of N-methyl-azabicyclo[4.1.0] heptane (8.64 g.; 0.078 mole), N-allylmethylamine (11.05 g.; 0.156 mole) 16.6 ml. of water and 0.2 g. of ammonium chloride was stirred and heated in an oil bath maintained at 115°-117° for 16 hours. The mixture was cooled, saturated with solid sodium hydroxide, and extracted well with ether. The ether extract was dried (MgSO4), evaporated through a Vigreux column, and the titled product residue was distilled at 13 mm.; b.p. 104°-105°, 7.27 g. (51% yield).

nmr in CDCl3 (100 MHz) was in accord. Mass spectrum M+ 182 (v. small).

Procedure III

A. trans-N-[2-(Dimethylamino)cyclohexyl]formamide

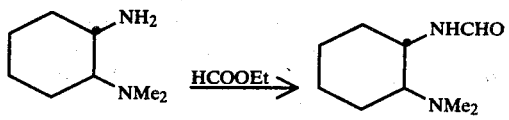

A solution of the diamine (5.12 g.; 0.036 mole) and 100 ml. of ethyl formate (distilled over potassium carbonate) was refluxed for 17 hours and evaporated. The product was distilled at 0.1 mm, b.p. 104°, 5.2 g. (85% yield). ir NH 3280, 3040; CH 2930, 2860; N-alkyl 2770; C=O 1670; amide II 1540; other 1450, 1385 cm$^{-1}$. NMR in CDCl3 (100 MHz) was in accord. Mass spectrum M+ 170.

B. N,N,N'-Trimethyl-1,2-cyclohexanediamine

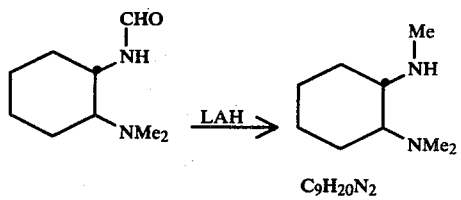

A solution of the N-formyl compound prepared in A (above) (4 g.; 0.0235 mole) in 50 ml. of ether was added during 5 minutes to a solution of lithium aluminum hydride (LAH) (4 g.) in 250 ml. of ethyl ether and refluxed 17 hours. It was cooled in ice, and decomposed by successive addition of 4 ml. of H2O, 4 ml. of 15% sodium hydroxide in water, 12 ml. of H2O, stirred 1 hour at room temperature and filtered. The cake was washed with ether, and the ether was distilled through a Vigreux column. The titled product residue was distilled at 14 mm, b.p. 86°-87°, 3 g. (82% yield). ir NH 3680 (very weak), 3320; CH 2940, 2820; N-alkyl 2780; CH 1475, 1450, C—N/other 1270, 1155, 1145, 1125, 1060, 1045, 1005, 870, 805, 775 cm$^{-1}$. NMR in CDCl3 (60 MHz) was in accord. Mass spectrum M+ 156.

TABLE I

Examples of Additional Cycloaliphatic Diamine Starting Materials Include the Following Compounds of the Formula

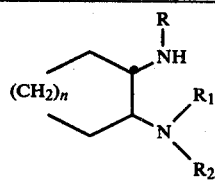

| No. | n. | N(R1)(R2) | R | Proc. | Molecular Formula | B.P.(°C.) |
|---|---|---|---|---|---|---|
| A | 2 | —N(CH3)—CH2—△ | CH3 | II | C12H24N2 | 127°-9° (13 mm) |
| B | 2 | —N(CH3)—CH2CH=CH2 | CH3 | II | C11H22N2 | 104°-5° (13 mm) |
| C | 2 | —N(CH3)2 | H | I | C8H18N2 | 78-79.5 (13 mm) |
| D | 2 | N(H)—CH3 | CH3 | II | C8H18N2 | 82°-3° (13 mm) |
| E | 2 | N(CH3)2 | CH3 | III | C9H20N2 | 86°-7° (14 mm) |

TABLE I-continued

Examples of Additional Cycloaliphatic Diamine Starting Materials Include the Following Compounds of the Formula

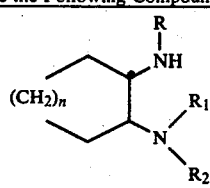

| No. | n. | NR₁R₂ | R | Proc. | Molecular Formula | B.P.(°C.) |
|---|---|---|---|---|---|---|
| F | 2 | N(CH₃)(CH₂-cyclobutyl) | $CH_3$ | II[a] | $C_{13}H_{26}N_2$ | 137°–8° (13 mm) |
| G | 2 | N(CH₃)(CH₂CH=C(CH₃)₂) | $CH_3$ | II[a] | $C_{13}H_{26}N_2$ | 138°–40° (13 mm) |
| H | 2 | pyrrolidinyl | $CH_3$ | II | $C_{11}H_{27}N_2$ | 118°–19° (13 mm) |
| I | 2 | 4-methylpiperazinyl | $CH_3$ | II | $C_{12}H_{25}N_3$ | 143°–5° (15 mm) |
| J | 2 | —N(CH₂CH₃)₂ | $CH_3$ | III | $C_{11}H_{24}N_2$ | 104°–5° (14 mm) |
| K | 2 | 3-hydroxypyrrolidinyl | $CH_3$ | II[a] | $C_{11}H_{22}N_2O$ | 128°–30° (0.1 mm) |
| L | 2 | —N(CH₂CH₃)₂ | H | I | $C_{10}H_{22}N_2$ | 100°–102° (14 mm) |
| M | 2 | —N(CH₃)((CH₂)₃CH₃) | $CH_3$ | II[a,b] | $C_{12}H_{26}N_2$ | 118°–20° (13 mm) |
| N | 2 | —N(CH₃)(CH₂CH₂OH) | $CH_3$ | II[a] | $C_{10}H_{22}N_2O$ | 158°–60° (13 mm) |
| P[c] | 1 | —N(CH₃)₂ | $CH_3$ | V | $C_8H_{20}N_2$ | 70° (13 mm) |
| Q | 3 | —N(CH₃)₂ | $CH_3$ | VI + III | $C_{10}H_{20}N_2$ | 108°–110° (17 mm) |
| R | 8 | —N(CH₃)₂ | $CH_3$ | VI + III | $C_{15}H_{32}N_2$ | 95°–100° (0.3 mm) |
| S | 2 | —N(CH₃)(CH₂CH₂-phenyl) | $CH_3$ | VIII | $C_{16}H_{26}N_2$ | 118°–9° (0.2 mm) |
| T | 2 | —N(CH₃)₂ | —CH(CH₃)₂ | IX | $C_{11}H_{24}N_2$ | 60°–62° (2 mm) |
| U | 2 | —N(CH₃)(CH₂-cyclopentenyl) | H | VIII | $C_{12}H_{20}N_2O$ | 85°–86° (0.25 mm) |
| V | 2 | 4-methylpiperazinyl | $CH_3$ | VIII | $C_{12}H_{25}N_3$ | 143°–5° (15 mm) |

Footnotes to Table 1
[a] only 2 eq. of amine
[b] reaction ran in a sealed bomb
[c] this diamine is 1,2-cis
Above structures supported by NMR, IR, UV and M.S.

The following preparations exemplify steps and procedures for preparing cis-1,2-diaminocycloalkanes which can be used to prepare compounds of this invention.

Procedure IV

Preparation of cis-N,N-dimethyl-1,2-cyclohexanediamine

A. 1-Dimethylaminocyclohex-1-ene

Titanium tetrachloride (237 g., 1.25 mole) was added in small portions over 4 hours to a solution of dimethylamine (307 g., 6.82 mole) and cyclohexanone (223 g., 2.27 mole) in 600 ml. ether. Temperature was maintained below 5° during the addition. The mixture was stirred overnight at room temperature. The precipitate was collected and washed with ether. The ether was removed by distillation and the residual oil distilled at reduced pressure. After a small forerun, 243 g. (86% yield) enamine 1-dimethylaminocyclohex-1-ene was obtained, b.p. 79°-80°/dd mm. The nmr (CDCl₃) was in accord.

The use of titanium tetrachloride in the preparation of enamines has been described in J. Org. Chem., 32, 213 (1967).

B. Ethyl ester of cis-2-(dimethylamino)-cyclohexanecarboxylic acid

A solution of ethyl chloroformate (105 g., 0197 mole) in 100 ml. benzene was added in 15 minutes to a solution of the enamine (243 g., 1.94 mole) in 1000 ml. benzene. The solution was refluxed overnight. The precipitate was collected and washed with benzene. The filtrate was concentrated to 1000 ml. and divided into four equal parts. Platinum oxide (5.0 g.) was added to each portion and hydrogenated at ~50 psi until uptake of hydrogen ceased (1.13 mole total). The catalyst was removed by filtration and the solution evaporated. The residual oil was distilled at reduced pressure to give 128 g. (66% yield) amino ester, b.p. 69°-71°/0.3 mm; ir CH 2940, 2860, 2820; N-alkyl 2760; C=O 1735; other 1655 w, 1620 w; CO 1175, 1155 cm⁻¹; nmr (CDCL₃) was in accord. Mass spectrum M+199.

Anal. Calcd. for $C_{11}H_{21}NO_2$: C, 66.29; H, 10.62; N, 7.03. Found: C, 66.31; H, 11.05; N, 6.78.

C. cis-2-(dimethylamino)cyclohexanecarboxylic acid hydrochloride

A solution of the amino ester prepared in (B) above (39.8 g., 0.30 mole) in 1500 ml. 10% HCl was refluxed for 19 hours. The water was removed first by distillation then at reduced pressure. The oily residue was treated with 500 ml. benzene and residual water removed by azeotropic distillation. The resulting solid was collected, washed with ether, and recrystallized from 350 ml. i-PrOH and 500 ml. ether. 50.9 g. (82% yield), m.p. 180°-181°; ir acid OH/NH⁺ 2660, 2620, 2480, 2460; C=O 1720; CO/CH 1250, 1180, 1155; other 1000, 875, 715 cm⁻¹; nmr (D₂O) was in accord. Mass spectrum M+ 171.

Anal. Calcd. for $C_9H_{17}NO_2 \cdot HCl$: C, 52.04; H, 8.73; N, 6.75; Cl, 17.07. Found: C, 51.95; H, 8.77; N, 6.67; Cl, 16.92.

D. Curtius Reaction with cis-2-(dimethylamino)cyclohexanecarboxylic acid

A mixture of the amino acid prepared in Part C (31.2 g., 0.15 mole), diphenyl phosphoryl azide (41.3 g.; 0.15 mole), and triethylamine (30.4 g., 0.30 mole) in 750 ml. benzene was refluxed with stirring for 1 hour. Benzyl alcohol (48.7 g., 0.45 mole) was added and the mixture refluxed overnight. The mixture was extracted with 10% HCl. The extract was washed with ether, made basic with 40% KOH, and extracted with ether. The organic layer was washed with water and saturated NaCl solution, dried, and evaporated. The residual oil was distilled to give 8.5 g. (20% yield) mixture of carbamate and benzyl ester, b.p. 130°-50°/0.1 mm. The nmr (CDCl₃) was consistent with a mixture of benzyl N-(2-dimethylaminocyclohexyl)carbamate and benzyl 2-dimethylaminocyclohexanecarboxylate.

E. cis-N,N-Dimethyl-1,2-cyclohexanediamine

The mixture obtained in Part D (above) (8.5 g.) was dissolved in 200 ml. ether, treated with 2.0 g. 10% Pd on carbon, and hydrogenated at 50 psi for 66 hours. The mixture was filtered and the ether removed by distillation. The supernatant was removed by pipette from the precipitate which formed on standing, and was distilled at reduced pressure to give 1.65 g. diamine, b.p. 70°/12 mm; ir NH 3350; CH 2910, 2850; N-alkyl 2750; NH def 1590; CH 1465, CN/other 1215, 1160, 1045 cm⁻¹ nmr (CDCl₃) was in accord. Mass spectrum M+142. The diamine was thus separated from the precipitate which on workup was found to be the amino acid, cis-2-(N-dimethylamino)cyclohexanecarboxylic acid.

The following preparations exemplify steps and procedures for preparing a cis-1,2-diaminocycloalkanes of the formula

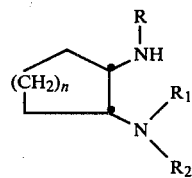

in which R is a $C_1$ to $C_3$-alkyl.

Procedure V

A. cis-N-[2-(Dimethylamino)-cyclohexyl]formamide

A solution of the diamine prepared above in Procedure IV, Part E (1.65 g., 11.6 mmole) in 50 ml. of ethylformate was refluxed overnight. The solution was evaporated to produce 2.07 g. (100% yield) of title formamide as a colorless oil. The material was used without purification. ir NH 3300; CH 2910, 2850; N-alkyl 2760; C=0 1670; amide ll 1535; other 1450, 1380, 1245, 1185, 1130, 1040, 980 cm⁻¹. nmr was in accord. Mass spectrum M+170.

B. cis-N,N,N'-Trimethyl-1,2-cyclohexanediamine

A solution of the N-formamide obtained in step (A) (2.0 g., 11.3 mmole) in 20 ml. ether was added in 15 minutes to a suspension of lithium aluminum hydride (LAH) (2.0 g.) in 100 ml. ether. The mixture was refluxed overnight. The excess LAH was decomposed by addition of 2 ml. water, 2 ml. 15% NaOH, and 6 ml. water. The precipitate was collected and washed with ether. The filtrate was dried (MgSO₄) and the ether removed by distillation. The residual oil was distilled at reduced pressure to give 1.40 g. (77% yield) of title diamine, b.p. 70°/13 mm; ir NH 3300; CH 2910, 2850; N-alkyl 2760; CH 1465, 1440; NH def/other 1365, 1335, 1240, 1165, 1140, 1110, 1090, 1040, 970, 890 cm⁻¹; nmr (CDCl₃) was in accord. Mass spectrum M+156.

This invention is further exemplified by the following detailed examples of procedures which can be used to prepare compounds of this invention, but they are not intended to limit the scope of the invention. All temperatures are in degrees Centigrade unless otherwise noted. For brevity, in the following examples, NaH means sodium hydride, DMF means N,N-dimethylformamide, THF means tetrahydrofuran, LAH means lithium aluminum hydride, MeI means methyl iodide, MeOH means methyl alcohol (methanol), CHCl₃ means chloroform, ether means diethyl ether, CH₂Cl₂ means methylene chloride, CdCl₃ means deuteriochloroform and HPLC means high pressure liquid chromatography, nmr means nuclear magnetic resonance spectral analyses, ir means infrared spectral analyses, tlc means thin layer chromatography, ptsa means p-toluenesulfonic acid, D₂O means deuterated water or deuterium oxide; DMSO means dimethyl sulfoxide, VPC means vapor phase chromatography.

General Procedure A for the preparation of amides using carbonyl diimidazole

EXAMPLE 1

(a) trans-N-[2-(Dimethylamino)cyclohexyl]-N-methyl-p-(methanesulfonyl)benzamide p-toluenesulfonate.

Carbonyldiimidazole (0.811 g.; 5 mmoles) was added to a solution of p-methanesulfonyl-benzoic acid (1 g.; 5 mmoles) in 40 ml. of THF, and the solution was stirred for 1 hour. A solution of N,N,N'-trimethylcyclohexane-1,2-diamine (0.781 g.; 5 mmoles) in 5 ml. of THF was added during 20 minutes, and the solution stirred for 23 hours. It was evaporated, the residue was taken up in 25 ml. of CHCl₃ and 10 ml. of saturated NaHCO₃, and the aqueous layer was extracted twice with CHCl₃. The combined CHCl₃ extract was washed with H₂O, saturated salt solution, dried (MgSO₄) and evaporated. The resulting amine base solid was crystallized from MeOH-ether; 1.02 g. of small rods, m.p. 195°–196°. uv λmax 217 nm (ε11,600); sh 235 (7,150); sh 265 (2,750); sh 272 (2,200). ir =CH 3000; N-alkyl 2760; C=O 1620; C=C 1580, 1570, 1500; SO₂/aromatic/other 1330, 1310, 1305, 1150, 1070, 965, 850, 780, 750. NMR in CDCl₃ and 100 MHz was in accord. Mass spectrum M+338. vpc 100% at 8.1 minutes.

Anal. Calcd. for $C_{17}H_{26}N_2O_3S$: C, 60.32; H, 7.74; N, 8.28; S, 9.47. Found: C, 60.41; H, 7.80; N, 8.30; S, 9.44.

The free base was converted to the titled salt with 1 mole of p-toluene sulfonic acid in MeOH- ether to give colorless prisms, m.p. 238°–239° unchanged on recrystallization from MeOH- ether. uv λmax 220 nm (ε24,100); sh 245 (5,650); sh 250 (4,800); sh 255 (4,000); sh 259 (5,350); sh 266 (2,600); sh 271 (2,100). ir N³⁰H 2720; C=O 1645; C=C 1600, 1495; SO₂/SO₃-/aromatic/other 1315, 1305, 1235, 1170, 1150, 1120, 1035, 1010, 955, 820, 755, 680. NMR in d₆DMSO and 100 MHz was in accord. Mass spectrum M+338.

Anal. Calcd. for $C_{17}H_{26}N_2O_3S \cdot C_7H_7SO_3H$: C, 56.44; H, 6.71; N, 5.49; S, 12.56. Found: C, 56.41; H, 6.79; N, 5.45; S, 12.32.

General Procedure B for the preparation of amides via the acid chloride

EXAMPLE 1

(b) trans-p-Chloro-N-[2-(dimethylamino)-cyclohexyl]N-methyl-benzamide maleate (1:1).

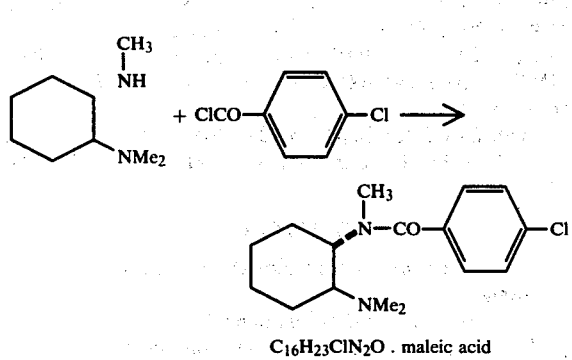

$C_{16}H_{23}ClN_2O$ . maleic acid

A solution of p-chlorobenzoyl chloride (0.875 g.; 5 mmoles) in 10 ml. of ether was added dropwise during 10 minutes to a solution of N,N,N'-trimethylcyclohexane-1,2-diamine (0.78 g.; 5 mmoles) in 50 ml. of ether containing triethylamine (0.505 g.; 5 mmoles) keeping the temperature at 20°–26°. The resulting suspension was stirred at room temperature for 17 hours. Saturated NaHCO₃ solution (25 ml.) was added, the ether layer was separated and the aqueous extracted once with ether. The combined ether extract was washed with H₂O, saturated salt solution, dried (MgSO₄) and evaporated. A solution of the crude solid in 10 ml. of 2%-MeOH—CHCl₃ was chromatographed on 130 g. of silica gel using the same solvent as eluent. The first fraction (500 ml.) and fractions 2–18 (25 ml. each) gave no material. Fractions 19–46 (25 ml. each) gave 1.1 g. which was crystallized from ether to give 1 g., of the amine base, m.p. 121°–122°. uv λmax 220 nm (ε12,550); sh 271; sh 277 (542). ir N-alkyl 2780; C=O 1625; C=C 1600, 1570, 1515, 1490. Aromatic 850. NMR in CDCl₃ and 100 MHz was in accord. Mass spectrum M+294 (small). Vpc 100% at 10.6 minutes.

Anal. Calcd. for $C_{16}H_{23}ClN_2O$: C, 65.18; H, 7.86; Cl, 12.02; N, 9.50. Found: C, 65.15; H, 7.66; Cl, 12.02; N, 9.23.

The free base was converted to the titled salt with equimolar amount of maleic acid in ether. Crystallization from methanol-ether gave colorless prisms, m.p. 172°–173°. uv sh 215 nm (ε25,350); sh 271 (1,550); sh 277 (670).ir N+H OHε3000 broad, 2780; C=O 1705, 1640; C=C/CO₂-1620, 1600, 1575, 1355; C—N 1090, 1070, 1010; aromatic 865. NMR in D₂O and 60 MHz was in accord, mass spectrum M+294 (v. small).

Anal. Calcd. for $C_{16}H_{23}ClN_2O \cdot C_4H_4O_4$: C, 58.46; H, 6.62; Cl, 8.63; N, 6.82. Found: C, 58.22; H, 6.55; Cl, 8.72; N, 6.83.

General Procedure C for reduction of amides with LAH

EXAMPLE 1

(c) N,N-Dimethyl-N'-ethyl-1,2-cyclohexanediamine

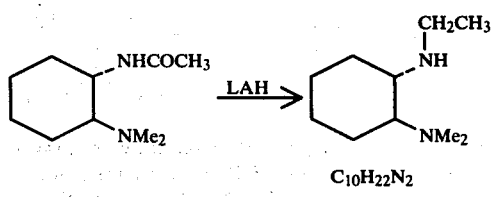

$C_{10}H_{22}N_2$

A solution of the trans-N-[2-(N,N-dimethylamino)cyclohexyl]acetamide (acetyl compound) (5.03 g.; 0.027 mole) in 100 ml. of ether was added during 10 minutes to a solution of LAH (5.03 g.) in 300 ml. of ether and the mixture was refluxed 24 hours. It was cooled, decomposed in succession with 5 ml. of H₂O, 5 ml. of 15% NaOH, and 15 ml. of H₂O. The suspension was stirred 1 hour at room temperature, filtered and the cake washed with ether. The solvent was evaporated through a 9" Vigreux and the product distilled at 91° (13 mm), 3.5 g. (76% yield). ir NH3680w, 3.300; CH 2960, 2920, 2850, 2820, N-alkyl 2780, CH/CN 1455, 1265, 1140, 1060, 1045, 1025, 1025. NMR in CDCl₃ (100 MHz) was in accord. Mass spectrum M+ 170.

Procedures for preparing starting Amines:

Procedure VI Via Aminocycloalkanol

A. trans-2-Dimethylaminocyclohexanol

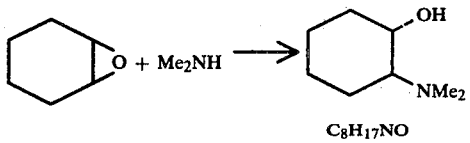

C₈H₁₇NO

A mixture of cyclohexene oxide (196.28 g.; 2 mole) and 40% aqueous dimethylamine (452 g.; 4 mole) was stirred for two hours. An exothermic reaction occurred and the mixture was kept at 50°–55° by occasional cooling. It was then stirred at room temperature for 20 hours, heated at 95° for 1 hour, and then for additional 1 hour with the condenser in the horizontal position. The mixture was cooled, extracted twice with ether (800 ml., 300 ml.), the ether extract was washed with saturated salt solution, dried (MgSO₄) and evaporated. Distillation at 15 mm gave 265.1 g. (93% yield), b.p. 82°–83°, uv end absorption. ir OH 3460; N-alkyl 2780; CH 1450; C—O/C—N 1300, 1280, 1270, 1185, 1120, 1085, 1060, 1035, 950, 875. NMR in CDCl₃ at 100 MHz confirmed trans stereo-chemistry. Vpc 5.7 minutes 98.97%.

This compound was previously prepared from cyclohexene oxide and dimethylamine in benzene at room temperature for 14 days in 95% yield, b.p. 90° (20 mm): J. Chem. Soc., 4835 (1965); or in autoclave: C. A. 67, 63899 d. Rocz. Chem. 41, 541 (1967) b.p. 88° (14 mm); also Bull. Soc. Chim. France, 850 (1947): hydrochloride and resolution reported.

B. trans-N,N-methyl-1,2-cyclohexanediamine

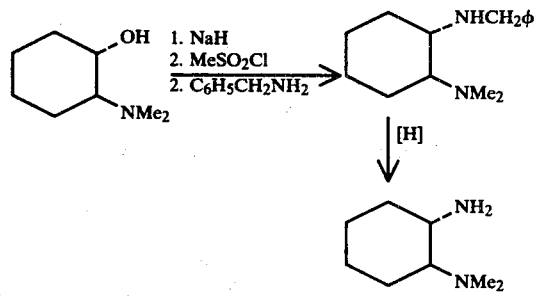

A solution of trans-2-dimethylaminocyclohexanol (58 g.; 0.405 mole) in 80 ml. of THF was added during 10 minutes to a suspension of NaH (17.05 g.; 0.405 mole of 57% dispersion in mineral oil) in 240 ml. of THF and the mixture was refluxed for 3 hours. It was cooled to 10°, and methanesulfonyl chloride (46.39 g.; 0.405 mole) was added dropwise during 30 minutes keeping the temperature below 15°. Benzylamine (86.79 g.; 0.81 mole) was then added during 5 minutes, the solvent was evaporated and heating continued at 95° for 16 hours. NaOH (500 ml. of 20% solution) was added and the mixture heated at 95° for 1 hour, cooled and extracted with ether (5×100 ml.). The ether solution was extracted with 10% HCl (6×100 ml.) and backwashed once with ether (discard). The acid extract was cooled, basified with 20% NaOH and extracted well with ether. The ether solution was washed with H₂O, saturated salt solution, dried (MgSO₄) and evaporated. Distillation at 0.4 mm gave 61 g. (65% yield) of N,N-dimethyl-N′-benzyl-1,2-cyclohexanediamine, b.p. 112°. It was identical by tlc to the sample prepared by the reaction of benzylamine with trans-2-chloro-dimethylaminocyclohexane.

A solution of the benzylamino compound was hydrogenated in two batches each containing 30.5 g. (0.131 mole), 175 ml. EtOH, 3.4 g Pd-C and 56.5 g. (0.394 mole) of 70% HClO₄, at initial pressure of 51.5 p.s.i. for 19 hours. The two batches were combined, filtered through Celite and evaporated in vacuo at 45°. The residue was cooled in ice, basified with 40% KOH to pH 11. The resulting thick suspension was extracted with ether (5×200 ml), the ether extract was dried (MgSO₄) and evaporated through a 9″ Vigreux. The residue was distilled at 13 mm to give 32.5 g. (87% yield), b.p. 77°–87.5°. Vpc 100% at 3.8 mm. ir and nmr was identical to those of the sample prepared by the reaction of 7-azabicyclo[3.1.0]heptane was dimethylamine.

Procedure VII Via Halocycloaliphatic Amine

A trans-N′-Benzyl-1,2-cyclohexanediamine, p-toluenesulfonate

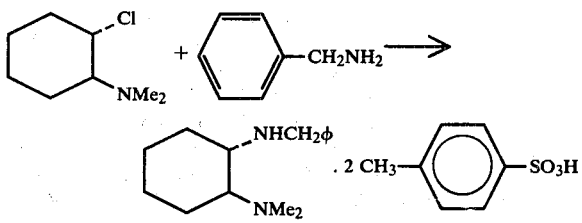

A mixture of trans 1-chloro-2-dimethylaminocyclohexane (56 g.; 0.346 mole) and benzylamine (74.15 g.; 0.692 mole) was heated at 95° for 17 hours. While still hot, it was poured into a solution of 85 ml. of conc. HCl and 425 ml. of H₂O, cooled and extracted with ether (discard ether). The acidic solution was cooled in ice, basified with 40% NaOH, and extracted with ether. The ether extract was cooled with H₂O, saturated salt solution, dried (MgSO₄) and evaporated. Distillation at 0.3 mm gave 35.17 g. (44% yield), b.p. 114°–116°. uv sh 209 nm (ε 11,100); λ max 247 (430); 252 (418); 258 (386); 264 (263); sh 267 (165); sh 278 (49); sh 288 (33). ir NH 3290; =CH 3020; CH 2920, 2850, 2820; N-alkyl 2780; C=C/NH def. 1600, 1585, 1495, 1455; C—N 1030; aromatic 745, 735, 700. nmr in CDCl₃ and 100 MHz was in accord. Mass spectrum M+ 282 (small).

The salt was prepared with 2 moles of p-TSA in ether, and crystallized from MeOH-ether, m.p. 158°–159.5°. uv λ max 211 nm (ε 22,750); 219 (24,050); sh 222 (23,900); sh 252 (502; 256 (640); 261 (686); 267 (496); sh 271 (248). ir N+H 3110-2600; N+H₂/C=C 1590, 1520, 1495, SO₃—/C—N/other 2235, 1220, 1170, 1150, 1120, 1030, 1005, 685; aromatic 820, 750, 700. NMR in D₂O and 100 MHz was in accord. Mass spectrum M+232.

Anal. Calcd. for C₁₅H₂₄N₂.2 pTSA: C, 60.39; H, 6.99; N, 4.86; S, 11.12. Found: C, 60.39; H, 7.13; N, 4.79; S, 11.28.

EXAMPLE 2 trans-3,4-Dichloro-N-[2-dimethylaminocyclohexyl]-benzamide

A solution of 3,4-dichlorobenzyl chloride (23.46 g.; 0.112 mole) in 100 ml. of ether was added dropwise during 20 minutes to a solution of N,N-dimethylcyclohexane-1,2-diamine (16 g.; 0.112 mole) in 400 ml. of ether containing 11.22 g. (0.112 mole) of triethylamine, keeping the temperature at 21°–25° with occasional cooling. The resulting suspension was stirred at room temperature for 20 hours. The suspension was diluted with 100 ml. of $H_2O$, stirred for 10 minutes, filtered and the solid washed with $H_2O$, then ether (Solid A). The filtrate was washed with $H_2O$, saturated $NaHCO_3$ and dried ($MgSO_4$). Solid A was dissolved in this ether solution and concentrated until crystallization began; 13.2 g. of colorless needles, m.p. 145°–146°. Second crop: 11.3 g., m.p. 144.5°–145.5°. Third crop: 4.4 g., m.p. 137°–139°. Yield 82%.

The analytical sample of the titled compound melted at 147°–148° (from ether). uv λmax 238 nm (ε13,277); sh (1,750); sh 287 (1,050). ir NH 3340, 3300; =CH 3080; N-alkyl 2760; C=O 1635; C=C 1605, 1590; amide ll 1540; C—N 1325, 1030; aromatic/C—Cl 895, 835, 760. NMR in $CDCl_3$ and 100 MHz was in accord. Mass spectrum M+ 315 (v. small).

Anal. Calcd. for $C_{15}H_{20}Cl_2N_2O$: C, 57.15; H, 6.40; Cl, 22.49; N, 8.89. Found: C, 57.51; H, 6.51; Cl, 22.75; N, 8.92.

EXAMPLE 3 trans-N-[2-(Dimethylamino)cyclohexyl]α,α,α-trifluoro-p-toluamide

The titled amide was prepared according to general procedure B using p-trifluoromethyl-benzoyl chloride (4.17 g.; 0.02 mole), N,N-dimethylcyclohexane-1,2-diamine (2.84 g.; 0.02 mole) and triethylamine (2.02 g., 0.02 mole). The crude solid was crystallized from ether to give 4.766 g. (77% yield) of colorless needles, m.p. 141°–142°, raised to 141.5°–142.5° on recrystallization. uv λmax 222 nm (ε11,450); sh 245 (5,550); sh 260 (3,400); sh 276 (1.750). ir NH 3310; =CH 3030; N-alkyl 2770, 2740; C=O 1635; C=C 1575, 1510; amide ll 1550; $CF_3$/ether 1330, 1190, 1165, 1130, 1105, 1065, 1020; aromatic 860; nmr in $CDCl_3$ at 100 MHz was in accord. Mass spectrum M+ 314.

Anal. Calcd. for $C_{16}H_{21}F_3N_2O$: C, 61.13; H, 6.73; F, 18.13; N, 8.91. Found: C, 60.86; H, 6.70; F, 18.41; N, 8.57.

EXAMPLE 4 trans-p-Chloro-N-[2-(dimethylamino)-cyclohexyl]-benzamide

This titled amide was prepared according to general procedure B using p-chlorobenzoylchloride (4.92 g.; 0.0281 mole), the trans-2-(N,N-dimethylamino)cyclohexylamine diamine (4 g.; 0.0281 mole) and triethylamine (2.84 g.; 0.0281 mole). The crude solid was crystallized from ether to give 3.42 g. of colorless needles, m.p. 130°–131°. Second crop: 2.5 g., m.p. 122°–125°. Yield: 75%. The analytical sample of the titled amide melted at 130.5°–131.5°. uv λmax 236 nm (ε15,000). ir NH 3310; N-alkyl 2760; C=O 1630; C=C 1595, 1570, 1490; amide ll 1545; C—N/other 1335, 1325, 1195, 1095, 1015; aromatic 845. NMR in $CDCl_3$ and 100 MHz was in accord. Mass spectrum M+ 280 (v. small).

Anal. Calcd. for $C_{15}H_{21}ClN_2O$: C, 64.16; H, 7.54; Cl, 12.63; N, 9.98. Found: C, 64.26; H, 7.69; Cl, 12.82; N, 9.73.

EXAMPLE 5 trans-N-[2-(Dimethylamino)cyclohexyl]-p-fluorobenzamide

This titled amine was prepared according to general procedure B using p-fluorobenzoylchloride (4.46 g.; 0.0281 mole), the trans-2-(N,N-dimethylamino)cyclohexylamine diamine (4 g.; 0.0281 mole) and triethylamine (2.84 g.; 0.0281 mole). The crude solid was crystallized from ether to give 3.06 g. of colorless needles, m.p. 124°–125°. Second crop: 1.78 g., m.p. 122°–123.5°. Yield of the titled amide: 65%. uv 227 nm (ε10,850); sh 263; sh 268; sh 272. ir NH 3320; N-alkyl 2760; C=O 1630; C=C 1605, 1590, 1505; amide ll 1545, C—N/C—F/other 1335, 1325, 1235, 1155, 1095; aromatic 865, 845, 760. nmr in $CDCl_3$ and 100 MHz in accord. Mass spectrum M+ 264 (v. small).

Anal. Calcd. for $C_{15}H_{21}FN_2O$: C, 68.15; H, 8.01; F, 7.19; N, 10.60. Found: C, 67.93; H, 8.01; F, 7.20; N, 10.50.

EXAMPLE 6 trans-p-Acetyl-N-[2-(dimethylamino)cyclohexyl]-benzamide p-toluenesulfonate

This titled amide was prepared by general procedure A from trans-2-(N,N-dimethylamino)cyclohexylamine, carbonyldiimidazole and 4-acetylbenzoic acid. The crude product was crystallized from MeOH- ether; colorless needles, 59% yield of the aminoamide, m.p. 158°–159°. uv λmax 251 nm (ε17,700). ir NH 3300; N-alkyl 2760; C=O 1685 ($COCH_3$), 1630 (NHCO); C=C 1610, 1505; amide ll 1545; C—N 1360, 1270, 1190; aromatic 850. nmr in $CDCl_3$ and 100 MHz was in accord. Mass spectrum M+ 288. Vpc 100% at 10.1 minutes.

Anal. Calcd. for $C_{17}H_{24}N_2O_2$. C, 70.80; H, 8.39; N, 9.72. Found: C, 70.96; H, 8.34; N, 9.65.

The titled salt of the amide was prepared with p-toluenesulfonic acid in MeOH-ether, and recrystallized from MeOH-ether, colorless plates, m.p. 211°–212°. uv λmax 222 nm (ε14,800); 227 (13,050); 251 (18,600); sh 288, sh 290, sh 293. ir NH 3320; N+H~3000 broad; C=O 1680 ($COCH_3$), 1660 (NHCO); amide ll 1550; C=C 1610, 1595, 1570, 1500; $SO_3^-$/other 1205, 1185, 1125, 1035, 1010, 680. nmr in $D_2O$ (100 MHz) was in accord. Mass spectrum M+ 288.

Anal. Calcd. for $C_{17}H_{24}N_2O_2 \cdot C_7H_7SO_3H$: C, 62.58; H, 7.00; N, 6.08; S, 6.96. Found: C, 62.32; H, 7.05; N, 5.99; S, 7.08.

EXAMPLE 7 trans-N-[2-(dimethylamino)cyclohexyl]-p-methanesulfonyl)-benzamide 2-naphthalene sulfonate This titled amide was prepared by general procedure A, as in Example 6, using 4-methylsulfonylbenzoic acid in place of the 4-acetylbenzoic acid.

The crude product was crystallized from ethylacetate, m.p. 185°–186.5°, 77% yield. The analytical sample melted at 187°–188°. uv λmax 228 nm (ε14,850); sh 263, sh 267, sh 272, sh 276. ir NH 3380, 3360; N-alkyl 2760; C=O 1640; C=C 1600, 1570; amide ll 1545; $SO_2$/C-N/other 1325, 1315, 1290, 1165, 1150, 1095, 970; aromatic/other 860, 785, 750. nmr in $CDCl_3$ (100 MHz) was in accord. Mass spectrum M+ 324. Vpc 100% at 8.1 minutes.

Anal. Calcd. for $C_{16}H_{24}N_2O_3S$: C, 59.23; H, 7.46; N, 8.64; S, 9.88. Found: C, 59.14; H, 7.38; N, 8.63; S, 9.92.

The titled salt was prepared with 1 mole of 2-naphthalene sulfonic acid in MeOH-ether; prisms, m.p. 231°–232°. uv sh 223 (102,550); λmax 227 (97,750); sh 245 (10,550); sh 254 (9,100); 263 (8,450); 273 (7,700); 285 (4,750); sh 298 (565); 305 (517); 312 (410); 318 (495). ir NH 3320; N+H~3000b, 2780 sh; C=O 1660; C=C 1605; 1595, 1570, 1505; amide ll 1550; $SO_2$ 1310, 1160, 1145; $SO_2^-$ 1205, 1180, 1090, 1030, 675; aromatic/other 865, 820, 750. NMR in $d_6DMSO$ (100 MHz) was in accord. Mass spectrum M+ 324.

Anal. Calcd. for $C_{16}H_{24}N_2O_3S \cdot C_{10}H_7SO_3H$: C, 58.62; H, 6.06; N, 5.26; S, 12.04. Found: C, 58.55; H, 6.10; N, 5.31; S, 12.10.

EXAMPLE 8 trans-2,4-Dichloro-N-[2-(dimethylamino)cyclohexyl]-benzamide

The titled amide was prepared from the transdiamine (Procedure VIII) and 2,4-dichlorobenzoylchloride according to general procedure B, but $CH_2Cl_2$ was used for extraction. The crude product was crystallized from ether, colorless needles, 64% yield, m.p. 128°–129°. uv sh 226 nm ($\epsilon$10,900); sh 270 (725); sh 278 (470). ir NH 3240, 3080; CH 2770; C=O 1635; C=C/amide ll 1590, 1565; aromatic 870, 845, 835. NMR in $CDCl_3$ and 100 MHz was in accord. Mass spectrum M+ 314.

Anal. Calcd. for $C_{15}H_{20}Cl_2N_2O$: C, 57.15; H, 6.40; Cl, 22.49; N, 8.89. Found: C, 56.81; H, 6.33; Cl, 22.45; N, 8.87.

EXAMPLE 9 trans-N-[2-(Dimethylamino)cyclohexyl]-p-nitro-benzamide

This titled amide was prepared from the trans-diamine and 4-nitrobenzoylchloride according to general procedure B using p-nitrobenzoylchloride (1.86 g.; 0.01 mole), the diamine (1.42 g.; 0.01 mole) and triethylamine (1.01 g.; 0.01 mole). The crude oil was crystallized from ether-petroleum ether (30°–60°); 2.232 g. (77% yield) of yellow needles, m.p. 103°–104°. The analytical sample melted at 102°–103°. uv sh 215 nm ($\epsilon$2,000); $\lambda$max 266 (11,800). ir NH 3380, 3320; N-alkyl 2780; C=O 1645; C=C 1605, 1595; amide ll/$NO_2$/C=C 1535, 1525, 1485, 1350; aromatic 870, 845, 720, nmr in $CDCl_3$ and 100 MHz was in accord. Mass spectrum M+ 291.

Anal. Calcd. for $C_{15}H_{21}N_3O_3$: C, 61.83; N, 7.27: N, 14.42. Found: C, 61.82; H, 7.45; N, 14.36.

EXAMPLE 10 trans-p-Bromo-N-[2(-dimethylamino)cyclohexyl]-benzamide

This title amide was prepared according to general procedure B, using 4-bromobenzoyl chloride (2.24 g.; 0.01 mole), the trans 2-(N,N-dimethylamino)cyclohexylamine diamine (1.42 g.; 0.01 mole) and triethylamine (1.01 g.; 0.01 mole). The crude product was crystallized from ether, colorless needles, 2.32 g. (71% yield), m.p. 157°–158° unchanged on recrystallization. uv $\lambda$max 241 nm ($\epsilon$16,200) ir NH/=CH 3300, 3070; N-alkyl 2760; C=O 1630; C=C 1590, 1565, 1485; amide ll 1545; aromatic 840. nmr in $CDCl_3$ and 100 MHz was in accord. Mass spectrum M+ 324 (v. small).

Anal. Calcd. for $C_{15}H_{21}BrN_2O$: C, 55.39; H, 6.51; Br, 24.57; N, 8.61. Found: C, 55.26; H, 6.66; Br, 24.43; N, 8.48.

EXAMPLE 11 trans N-[2-(Dimethylamino)cyclohexyl]-p-anisamide, also named trans-N-[2-(dimethylamino)cyclohexyl]-4-methoxybenzamide This titled amide was prepared according to general procedure B using p-anisoylchloride (1.71 g.; 0.01 mole), the trans-2-(N,N-dimethylamino)cyclohexylamine diamine (1.42 g.; 0.01 mole) and triethylamine. The crude product was crystallized from ether in two crops; colorless needles; 1.664 g. (60% yield), m.p. 138°–139°. uv $\lambda$max 252 nm ($\epsilon$ 16,450); sh 276 (4,150); 282 (2,100). ir NH 3300; N-alkyl 2770; C=O 1625; C=C 1610, 1580, 1510; amide II 1540; C—O/C—N 1335, 1310, 1205, 1185, 1025; aromatic 845. NMR in $CDCl_3$ (100 MHz) was in accord. Mass spectrum M+ 276.

Anal. Calcd. for $C_{16}H_{24}N_2O_2$: C, 69.52; H, 8.75; N, 10.13. Found: C, 69.24; N, 8.96; N, 10.14.

EXAMPLE 12 trans-N-[2-(Dimethylamino)cyclohexyl]-4-nitro-m-anisamide

3-Methoxy-4-nitrobenzoyl chloride was prepared from the acid and $PCl_5$ according to J. Amer. Chem. Soc. 74 4969 (1952).

The titled amide was prepared according to general procedure B using this acid chloride (2.16 g.; 0.01 mole), the trans diamine (1.42 g.; 0.01 mole) and triethylamine (1.01 g.; 0.01 mole). The crude oil was crystallized from ether to give two crops; 2.6 g. (80% yield), m.p. 116°–117° unchanged on recrystallization. uv sh 235 nm ($\epsilon$ 8,600); $\lambda$max 258 (6,950); 327 (3,300). ir NH 3300; =CH 3080, 3040; N-alkyl 2770; C=O 1630; C=C/$NO_2$/amide II/C—N/C—O 1610, 1585, 1555, 1525, 1490, 1365, 1325, 1255, 1025; aromatic 840. NMR in $CDCl_3$ (100 MHz) was in accord. Mass spectrum M+ 321 (small).

Anal. Calcd. for $C_{16}H_{23}N_3O_4$: C, 59.80; H, 7.21; N, 13.07. Found: C, 59.77; H, 7.20; N, 12.96.

EXAMPLE 13 trans-N-[2-(Dimethylamino)cyclohexyl]-3-hydroxy-4-nitro-benzamide

A solution of boron tribromide (7.52 g.; 0.03 mole) in 20 ml. of $CH_2Cl_2$ was added to a solution of trans-N-[2-(dimethylamino)cyclohexyl]-3-methoxy-4-nitrobenzamide (1.93 g.; 0.006 mole) in 50 ml. of $CH_2Cl_3$ keeping the temperature at −50° to −70°. It was allowed to warm to room temperature and stirred overnight. The mixture was concentrated in vacuo at 30° to a small volume, ice-water was added followed by solid $NaHCO_3$ to pH 8, then solid NaCl and extracted with ethyl acetate (5×100 ml). The extract was dried ($MgSO_4$) and evaporated to give 0.657 g. of solid. The aqueous was extracted again with $CHCl_3$ (4×100 ml.) to give 0.561 g. of solid. The last extraction was repeated to give 0.3 g. of solid. The three crops were crystallized from benzene to give 0.548 g. of orange prisms, m.p. 139°–140°. The analytical sample melted at 138°–140° (efferv.). NMR analysis showed this product to contain ca. 30% of benzene. This impure titled product was heated at 120°–125° for 17 hours in a sublimation tube (the m.p. changed to 198°–199.5°) and was then sublimed at 170°–175° for 18 hours. The sublimate, orange prisms, melted at 202°–203.5°. uv $\lambda$max 238 nm nm ($\epsilon$ 11,600); 278 (7,900); 358 (2,350); 422 (2,850). ir NH/=CH/N+H/OH 3220, 3180, 3020, ∼2900 broad, C=O 1655; C=C 1600; amide II/$NO_2$/C=C 1580, 1485, 1335; C—N/C—O 1260, 1240, 1220, 1155, 995. NMR in $CDCl_3$+$d_6$DMSO (100 MHz) showed absence of benzene. Mass spectrum M+ 307.

Anal. Calcd. for $C_{15}H_{21}N_3O_4$: C, 58.61; H, 6.89; N, 13.67. Found: C, 58.42; H, 6.87; N, 13.82.

EXAMPLE 14 trans-p-Cyano-N-[2-(dimethylamino)cyclohexyl]-benzamide

The titled amide was prepared according to general procedure B using p-cyanobenzoyl chloride (1.65 g.; 0.01 mole), the trans-2-(dimethylamino)cyclohexylamine (1.42 g.; 0.01 mole) and triethylamine (1.01 g.; 0.01 mole) but using $CH_2Cl_2$ for extraction. The crude solid was crystallized from ether to give colorless needles, 1.71 g. (63% yield), m.p. 160°–161°. uv λmax 236 nm (ε 17,900); sh 285 (2,550). ir NH 3320; N-alkyl 2780; C≡N 2220; C=O 1635; C=C 1610, 1500; amide II 1550; aromatic 860. NMR in $CDCl_3$ (60 MHz) was in accord. Mass spectrum M+ 271.

Anal. Calcd. for $C_{16}H_{21}N_3O$: C, 70.82; H, 7.80; N, 15.49. Found: C, 70.76; H, 8.13; N, 15.75.

EXAMPLE 15 trans-N-[2-(Dimethylamino)cyclohexyl]-p-toluamide

This titled amide was prepared by the general procedure B using p-toluyl chloride (1.54 g.; 0.01 mole), the trans-2-(dimethylamino)cyclohexylamine (1.42 g.; 0.01 mole) and triethyl amine (1.01 g.; 0.01 mole). The crude solid was crystallized from ether to give 1.624 g. (63% yield) of colorless rods, m.p. 160°–161°. uv λmax 235 nm (ε 14,050). ir NH 3300; N-alkyl 2770; C=O 1625; C=C 1615, 1575, 1505; amide II 1535; C—N 1335, 1325; aromatic 835. NMR in $CDCl_3$ (100 MHz) was in accord. Mass spectrum M+ 260.

Anal. Calcd. for $C_{16}H_{24}N_2O$: C, 73.80; H, 9.29; N, 10.76. Found: C, 73.53; H, 9.44; N, 10.77.

EXAMPLE 16 trans-m-Chloro-N-[2-(dimethylamino)cyclohexyl]-benzamide

This titled amide was prepared by general procedure B from 2-(dimethylamino)cyclohexylamine and 3-chlorobenzoyl chloride. The crude product was crystallized from ether-petroleum ether (30°–60°); yield 62%, m.p. 112°–113°. The analytical sample melted at 112.5°–113.5°. uv sh 217 nm (ε 11,850); sh 226 (9,550); sh 277 (1,200); sh 287 (623). ir NH/=CH 3320, 3070; N-alkyl 2760; C=O 1635; C=C 1595, 1570; amide II 1545. NMR in $CDCl_3$ (100 MHz) was in accord. Mass spectrum M+ 280.

Anal. Calcd. for $C_{15}H_{21}ClN_2O$: C, 64.16; H, 7.54; Cl, 12.63. Found: C, 64.02; H, 7.43; Cl, 12.78; N, 9.98.

EXAMPLE 17 trans-N-[2-(dimethylamino)cyclohexyl]-m-trifluoromethylbenzamide p-toluenesulfonate This titled amide was prepared by general procedure B from trans-2-(dimethylamino)cyclohexylamine and 3-trifluoromethylbenzoyl chloride. The crude oil was converted to the salt with 1 mole of p-toluenesulfonic acid in ether, and was crystallized from MeOH-ether, 47% yield, colorless plates, m.p. 208°–209°. uv λmax 222 nm (ε 22,150); sh 227 (17,900); sh 259 (1,550); sh 266 (1,100); sh 274 (566). ir NH/N+H 3280, 3040; C=O 1660; C=C/amide II 1615, 1595, 1550, 1495; $CF_3/SO_3^-/CN$ 1335, 1320, 1275, 1200, 1180, 1160, 1120, 1075, 1035, 1010; aromatic/$SO_3^-$ 705, 690, 680. NMR in $CDCl_3$ (100 MHz) was in accord. Mass spectrum M+ 314.

Anal. Calcd. for $C_{16}H_{21}F_3N_2O \cdot C_7H_8O_3S$: C, 56.77; H, 6.01; F, 11.72; N, 5.76; S, 6.59. Found: C, 56.78; H, 6.14; F, 11.68; N, 5.32; S, 6.84.

Procedure VIII

Trans-p-Bromo-N-[(2-dimethylamino)cyclohexyl]-N-methylbenzamide hydrochloride
First Method of Preparing Starting trans-diamine (with a secondary amino group in the 1-position).

A. trans-N,N'-Trimethyl-1,2-cyclohexanediamine

A solution of trans-2-dimethylaminocyclohexanol (61.1 g.; 0.427 mole) in 85 ml. of THF was added during 5 minutes to a suspension of NaH (17.97 g.; 0.427 mole of 57% dispersion in mineral oil) in 250 ml. of THF, and the mixture was heated at 95° for 2 hours. It was cooled to 10°, and treated dropwise with methanesulfonyl chloride (48.91 g.; 0.427 mole) during 40 minutes keeping the temperature at 15°. N-Methylbenzylamine (103.48 g.; 0.854 mole distilled) was then added. THF was evaporated and heating continued at 95° for 18 hours. The mixture was treated with 500 ml. of 20% NaOH, heated at 95°, cooled and extracted with ether (6×100 ml.). The ether solution was extracted with 10% HCl (6×100 ml.), backwashed with ether (discard ether), cooled, basified with 20% NaOH and extracted with ether. The ether extract was washed with $H_2O$, saturated salt solution, dried ($MgSO_4$) and evaporated to give 48.6 g. of crude N,N,N'-trimethyl-N'-benzyl-1,2-cyclohexanediamine as an oil. A solution of this oil (46.6 g.) was hydrogenated in two portions each in 130 ml. of EtOH, with 2.6 g. of 10% Pd-C and 28.6 g. of 70% $HClO_4$ at initial pressure of 51 p.s.i. for 22 hours. The mixture was filtered through Celite, the filtrate was evaporated, cooled in ice and basified with 40% KOH. The resulting thick suspension was extracted with ether (4×200 ml.), the ether extract was dried ($MgSO_4$) and evaporated. The product boiled at 87°–88° (15 mm. Hg.). Vpc-mass spectrum showed that the first peak was 3.4 minutes, was N,N-dimethyl-1,2-cyclohexanediamine and the second peak (4.1 minute) was the desired N,N,N'-trimethyl-1,2-cyclohexanediamine.

A solution of the distillate (23.8 g.) in 50 ml. of ether was chromatographed on a column of Woelm neutral alumina (1200 g.) and eluted with 5% MeOH-ether. Fractions 1–9 (900 ml.) gave no material. Fractions 10–27 (50 ml. each) gave 18.68 g. (the impurity was retained on the column). Distillation at 13 mm gave 17 g., b.p. 81°–82°. Vpc 100% at 5.1 minutes nmr in $CDCl_3$ and 60 MHz was identical to that prepared by Procedure IX B and C (below).

Procedure IX Second method for preparing trans-diamine

A. trans-N-Benzyl-N-[2-(dimethylamino)-cyclohexyl]formamide p-toluenensulfonate (1:1)

A solution of trans-N-benzyl-N,N'-dimethyl-1,2-cyclohexanediamine (9.29 g.; 0.04 mole) in 40 ml. of formic acid was refluxed 20 hours, added and poured into 200 g. of ice. It was basified with 15% NaOH and extracted well with ether. The extract was washed with $H_2O$, saturated salt solution, dried ($MgSO_4$) and evaporated. The residue (9.7 g.) was converted to the salt with 2 mole of p-TSA in ether. The resulting gum was crystallized from MeOH-ether to give 13.64 g.; of the titled compound, m.p. 201°–202.5°. The analytical sample melted at 202°–203°. uv sh 210 nm (ε 27,850); sh 222 (25,600); sh 227 (12,350); sh 243 (302); sh 248 (375); λ max 254 (472); 258 (556); 261 (562); 268 (399); sh 272 (175). ir N+H 2720, 2560; C=O 1670, 1650; C=C 1600, 1495; $SO_3$/ether 1225, 1170, 1120, 1030, 1010, 815, 705, 685. nmr in $D_2O$ (100 MHz) was in accord. Mass spectrum M+ 260.

Anal. Calcd. for $C_{16}H_{24}N_2O \cdot C_7H_7 \cdot SO_3H$: C, 63.86; H, 7.46; N, 6.48; S, 7.41. Found: C, 64.04; H, 7.49; N, 6.34; S, 7.86.

The free base was prepared by basification of the ether-$H_2O$ suspension of the above salt and extraction with ether, and was a colorless oil.

B. trans-N-Benzyl-N,N',N'-trimethyl-1,2-cyclohexanediamine p-toluene sulfonate (1:1)

A solution of the free base from part A above (5.7 g.; 0.0219 mole) in 100 ml. of ether was added to a solution of LAH (5.7 g.) in 300 ml. of ether during 10 minutes, and the mixture was refluxed overnight. It was cooled in ice, and decomposed in succession with 5.7 ml. $H_2O$, 5.7 ml. of 15% MaOH and 17.1 ml. of $H_2O$. The suspension was stirred at room temperature for 1 hour, filtered and the cake washed with ether. The filtrate was dried (MgSO$_4$), and evaporated to give 5.6 g. of oil. The salt was prepared from 4.19 g. of the titled amine base and 1 mole of p-toluenesulfonic acid monohydrate in ether. The resulting gum was crystallized from MeOH-ether; colorless needles of amine salt, 4.64 g., m.p. 143.5°–145°. uv λ max 206 nm (ε 16,400); sh 221 (13,350); sh 226.5 (8,600); sh 247 (359); sh 252 (407); 257 (463); 261 (446); 267 (298); sh 271.5 (138) ir N+H~broad; =CH 3060, 3040, 3020; N-alkyl 2810; C=C 1605, 1495; $SO_3^-$/other 1215, 1175, 1145, 1050, 1030, 1010, 815, 740, 695, 680. nmr in $D_2O$ (100 MHz) was in accord. Mass spectrum M+ 246.

Anal. Calcd. for $C_{16}H_{26}N_2 \cdot CH_3C_6H_4SO_3H$: C, 65.99; H, 8.19; N, 6.69; S, 7.66. Found: C, 66.12; H, 8.04; N, 6.45; S, 7.69.

C. trans-N,N',N'-trimethylcyclohexane-1,2-diamine

The p-toluenesulfonate salt from part B above was basified with aqueous sodium hydroxide to give the free diamine base as an oil. A solution of this oil was hydrogenated over 10 percent palladium on carbon and 70 percent perchloric acid (HClO$_4$) and further treated as in Procedure VIII to give the titled diamine.

Procedure X

Third Method for preparing starting transdiamine with secondary amine at the 1-position A. trans-N-[2-(Dimethylamino)-cyclohexyl]-formamide A solution of the trans-2-(dimethylamino)cyclohexylamine prepared as in Procedure VIII (5.12 g.; 0.036 mole) and 100 ml. of ethyl formate (distilled over $K_2CO_3$) was refluxed for 17 hours and evaporated. The titled product (A) was distilled at 0.1 mm, b.p. 104°, 5.2 g. (85% yield). ir NH 3280, 3040; CH2930, 2860; N-alkyl 2770; C=O 1670; amide II 1540; other 1450, 1385. nmr in CDCl$_3$ (100 MHz) was in accord. Mass spectrum M+ 170.

B. N,N,N'-Trimethyl-1,2-cyclohexanediamine

A solution of the N-formyl-N-[2-(dimethylamino)cyclohexanediamine (4 g.; 0.0235 mole) in 50 ml. of ether was added during 5 minutes to a solution of LAH (4 g.) in 250 ml. of ether and refluxed 17 hours. It was cooled in ice, and decomposed in succession with 4 ml. of $H_2O$, 4 ml. of 15% NaOH, 12 ml. of $H_2O$, stirred 1 hour at room temperature and filtered. The cake was washed with ether, and the ether was distilled. The titled amine (B) residue was distilled at 14 mm, b.p. 86°–87°, 3 g. (82% yield). ir NH 3680 v.w., 3320; CH 2940, 2820; N-alkyl 2780; CH 1475, 1450; C—N/other 1270, 1155, 1145, 1125, 1060, 1045, 1005, 870, 804, 775. nmr in CDCl$_3$ (60 MHz) was in accord. Mass spectrum M+ 156.

EXAMPLE 18 trans-N-[(2-dimethylamino)cyclohexyl]-N-methyl-p-bromo-benzamide hydrochloride

This titled amide was prepared by general procedure B using 4-bromobenzoyl chloride (1.10 g.; 5 mmole), N,N,N'-trimethyl-1,2-cyclohexane diamine (0.78 g.; 5 mmole) and triethylamine (0.505 g.; 5 mmole). The crude solid was chromatographed on 155 g. of silica gel using 1% MeOH—CHCl$_3$. Fractions 1-12 (750 ml. total) gave no material. Fractions 13-47 (25 ml. each) gave 1.2 g. Crystallization from ether gave 0.877 g. of the titled aminoamide as prisms, m.p. 124°–125°. uv λ max 226 nm (ε 12,450); sh 272; sh 278 (560). ir N-alkyl 2780; C=O 1625; C=C 1590, 1565; other 1070; aromatic 845. nmr in CDCl$_3$ (60 MHz) was in accord. Mass spectrum M+ 338 (v. small).

Anal. Calcd. for $C_{16}H_{23}BrN_2O$: C, 56.64; H, 6.83; Br, 23.56; N, 8.26. Found: C, 56.66; H, 7.05; Br, 23.25; N, 8.17.

The amino-amide salt was prepared with ethereal HCl, and was crystallized from MeOH-ether, colorless prisms, m.p. 212°–213°. uv λ max 227 nm (ε 12,250); sh 272 (902); sh 278 (485). ir NH 3320, 3240; N+H 2720, 2660; C=O 1630; C=C/other 1590, 1565, 1485, 1395, 1335, 1325, 1050, 1010, 755; aromatic 840. nmr in $D_2O$ and 60 MHz was in accord. Mass spectrum M+ 338 (v. small).

Anal. Calcd. for $C_{16}H_{23}BrN_2O \cdot HCl$: C, 51.14; H, 6.44; Cl, 9.43; Br, 21.27; N, 7.46. Found: C, 51.00, H, 6.49; Cl, 8.33; Br, 21.55; N, 7.43.

EXAMPLE 19 trans-N-[2-(dimethylamino)cyclohexyl]-N-methyl-p-acetyl-benzamide p-toluenesulfonate The amide was prepared by general procedure A using the amine from Procedure X, carbonyl-diimidazole and 4-acetylbenzoic acid.

The titled salt was prepared with 1 mole of p-toluenesulfonic acid in MeOH-ether in 47% yield; colorless plates, m.p. 195°–196°. uv sh 221 nm (ε 17,800); sh 227 (15,100); λ max 252 (13,750). ir NH~3000, 2740; C=O 1695, 1640; C=C 1610, 1570, 1510, 1485; $SO_3^-$/C-N/other 1330, 1265, 1220, 1170, 1150, 1120, 1030, 1010, 680; aromatic 840, 815. nmr in $D_2O$ (100 MHz) was in accord. Mass spectrum M+ 302.

Anal. Calcd. for $C_{18}H_{26}N_2O_2 \cdot C_7H_7 \cdot SO_3H$: C, 63.26; H, 7.22; N, 5.90; S, 6.76. Found: C, 63.09; H, 7.28; N, 5.96; S, 6.80.

EXAMPLE 20 trans-N-[2-dimethylamino)cyclohexyl]-N-methyl-m-anisamide p-toluenesulfonate

The titled amide base was prepared by general procedure B, from amine of Procedure X and 3-methoxybenzoyl chloride. The crude product was crystallized from petroleum-ether (30°–60°); 83% yield, m.p. 79°–80°. uv sh 219 nm (ε 13,650); sh 274 (2,250); λ max 256 (2,350); 279 (2,450). ir =CH 3060; N-alkyl 2780; C=O 1626; C=C 1600, 1585; C—O/C—N 1325, 1260, 1245, 1030; aromatic/other 875, 795, 755, 740. nmr in CDCl$_3$ (100 MHz) was in accord. Mass spectrum 289 (M+ −1).

Anal. Calcd. for $C_{17}H_{26}N_2O_2$: C, 70.31; H, 9.02; N, 9.65. Found: C, 70.32; H, 8.99; N, 9.67.

The titled amide salt was prepared with 1 mole of p-toluenesulfonic acid in MeOH-ether, and recrystallized from MeOH-ether; colorless plates, m.p. 181°–182°. uv λ max 219 nm (ε 23,800); sh 227 (16,750); 261 (1,450); sh 269 (1,700); sh 275 (2,100); 281 (2,300). ir N+H 2720; C=O 1635; C=C 1610, 1580, 1495, 1480; C—O/C—N/$SO_3^-$ 1220, 1170, 1120, 1045, 1030, 1010, 680; aromatic 815, 780. nmr in $D_2O$ and 100 MHz was in accord. Mass spectrum 289 (M+ −1).

Anal. Calcd. for $C_{17}H_{26}N_2O_2 \cdot C_7H_7 \cdot SO_3H$: C, 62.31; H, 7.41; N, 6.06; S, 6.93. Found: C, 62.24; H, 7.61; N, 6.03; S, 6.84.

EXAMPLE 21 trans-N-[2-(Dimethylamino)cyclohexyl]-N-methyl-4-nitro-m-anisamide

This amide was prepared according to general procedure B using the amine in Procedure X and 3-methoxy-4-nitrobenzoyl chloride.

The crude oil was crystallized from ether; colorless needles, 81% yield, m.p. 114°–115°. uv sh 215 nm ($\epsilon$ 20,050); $\lambda$ max 263 (5,400); 323 (3,200). ir N-alkyl 2780; C=O 1630; C=C/NO$_2$/C—O/C—N 1405, 1355, 1325, 1275, 1260, 1070, 1065, 1020; aromatic 885, 875, 835, 715 cm$^{-1}$. nmr in CDCl$_3$ (60 MHz) was in accord. Mass spectrum M+ 335.

Anal. Calcd. for $C_{17}H_{25}N_2O_4$: C, 60.88; C, 7.51; N, 12.53. Found: C, 60.82; H, 7.69; N, 12.48.

EXAMPLE 22 trans-N-[2-(Dimethylamino)-cyclohexyl]-3-hydroxy-N-methyl-4-nitrobenzimide

A solution of boron tribromide (7.76 g,; 31 mmole) in 20 ml. of CH$_2$Cl$_2$ was added during 40 minutes to a solution of the Example 21 titled product (2.09 g.; 6.2 mmole) in 50 ml. of CH$_2$Cl$_2$ keeping the temperature at $-70°$. The mixture was then allowed to warm to room temperature and was stirred overnight. It was concentrated to a small volume in vacuo at 30°, ice and H$_2$O were added, followed by solid NaHCO$_3$ to pH 8. The mixture was extracted with CHCl$_3$ (4×100 ml.), the extract was dried (MgSO$_4$) and evaporated. A solution of the brown amorphous solid (1.4 g.) in 10 ml. of 2% MeOH—CHCl$_3$ was chromatographed on 140 g. of silica gel in the same solvent system. Fractions 1 (500 ml.) and fractions 2–45 (25 ml. each) gave no material. Fractions 49–90 (25 ml. each) gave 0.76 g. of a yellow solid (m.p. 120°–123°). Crystallization from benzene-petroleum ether (30°–60°) gave 0.264 g. of small yellow crystals, m.p. 126°–127.5°. Second crop: 83 mg., m.p. 125°–128.5°. uv sh 235 nm ($\epsilon$ 7,650); $\lambda$ max 277 (6,950); 343 (3,850); sh 415 (585). ir OH 2380; C=O 1660, 1630; C=C 1605, 1480; NO$_2$ 1550, 1330; C—N/C—O 1255 cm$^{-1}$. nmr in CDCl$_3$ (60 MHz) was in accord. Mass spectrum M+ 321.

Anal. Calcd. for $C_{16}H_{23}N_2O_4$: C, 59.80; H, 7.21; N, 13.07. Found: C, 59.93; H, 6.89; N, 12.96.

EXAMPLE 23A trans-N-methyl-N-[2-(Dimethylamino)cyclohexyl]-α,α,α-trifluoro-p-toluamide By methylation of trans-N-[2-(dimethylamino)cyclohexyl]-α,α,α-trifluoromethyl-p-toluamide A mixture of the Example 3 titled product (0.944 g., 3 mmoles), NaH (0.126 g., 3 mmoles of 57% dispersion in mineral oil) and 20 ml. of DMF was heated at 95° for 30 minutes. It was cooled to room temperature, treated during 1 hour with a solution of Me: (0.44 g.; 3.1 mmole) in 10 ml. of DMF and stirred over the weekend. It was evaporated, the residue taken up in CH$_2$Cl$_2$—H$_2$O, the organic layer was washed with H$_2$O, saturated salt solution, dried (MgSO$_4$) and evaporated. The residue was chromatographed on 140 g. of silica gel using 2% MeOH—CHCl$_3$. Fraction 1 (250 ml.) gave no material. Fractions 2–44 gave 0.202 g. Crystallization from petroleum-ether (30°–60°) gave colorless needles of the titled product, 0.161 g. (16% yield), m.p. 83°–84°. uv sh 230 nm ($\epsilon$ 5,550); sh 265 (1,800). ir N-alkyl 2790; 1685 v.w.; C=O 1630, 1620; C=C 1580, 1520, 1490; CF$_3$/C—N/other 1325, 1165, 1125, 1105, 1075, 1015; aromatic 865, 840. nmr in CDCl$_3$ and 100 MHz was in accord. Mass spectrum M+ 328. Vpc 97.84% at 8.5 minutes.

Anal. Calcd. for $C_{17}H_{23}F_3N_2O$: C, 62.17; H, 7.06; F, 17.36; N, 8.53. Found: C, 62.09; H, 7.27; F, 17.66; N, 8.36.

EXAMPLE 23B

By acylation of N,N,N'-trimethyl-1,2-cyclohexanediamine

This titled amide was prepared by general procedure B from amine from Procedure X and 4-trifluoromethylbenzoylchloride. The titled product was crystallized from petroleum-ether (30°–60°), colorless needles, 86% yield, m.p. 85°–86°. It was identical to the sample prepared in Example 23A as shown by tlc, uv and nmr.

EXAMPLE 24

Trans-N-[2-(N-allyl-N-methylamino)cyclohexyl]-α,α,α-trifluoro-p-toluamide hydrochloride A. trans-N-Allyl-N-methyl-1,2-cyclohexanediamine, 2-naphthalenesulfonate (1:2)

A mixture of 7-azabicyclo[3.1.0]heptane (19.43 g.; 0.2 mole), N-allyl-methylamine (28.44 g.; 0.4 mole) and 42.8 ml. of H$_2$O was heated in an oil bath at 96°–98° for 22 hours. It was cooled, solid NaOH was added followed by salt, and extracted with ether (4×100 ml.). The ether extract was dried (MgSO$_4$), evaporated through a 9" Vigreux, and the amine residue was distilled through a 24" Spinning band column at 13 mm to give 11.3 g. (34% yield), b.p. 98°–98°. ir NH 3360, 3300; =CH 3080; CH 2980, 2920, 2860; N-alkyl 2780; C=C 1640; NH def. 1580; CH 1450, 1425, 1415, 1340; C—N/CH=CH$_2$ 1050, 1035, 995, 915, 870. nmr in CDCl$_3$ (100 MHz) was in accord. Mass spectrum M+ 168 (v. small).

The titled amine salt was prepared with 2 moles of 2-naphthalenesulfonic acid in MeOH-ether; m.p. 188°–189° unchanged on recrystallization from MeOH-ether. uv sh 224 nm ($\epsilon$ 122,650); $\lambda$ max 227 (149,900); sh 256 (7,050); 266 (9,600); 275 (10,250); sh 284 (6,950); sh 299 (877); 306 (947); 312 (778); 319 (947). ir N+H 2720; C=C/N+H 1675, 1605, 1595, 1565, 1505; SO$_3^-$/C—N 1250, 1210, 1185, 1135, 1090, 1025, 1015; CH=CH$_2$ 940; aromatic 820, 750; SO$_3$ 675. nmr in d$_6$DMSO was in accord. Mass spectrum M+ 168 (small).

Anal. Calcd. for $C_{10}H_{20}N_2 \cdot C_{10}H_7SO_3H$: C, 61.62; H, 6.21; N, 4.79; S, 10.97. Found: C, 61.48; H, 6.44; N, 4.75; S, 11.30.

B. trans-N-[2-(Allylmethylamino)cyclohexyl]-α,α,α-trifluoro-p-toluamide monohydrochloride This titled amide was prepared by general procedure B from the amine from part A and 4-trifluoromethylbenzoyl chloride. The crude product was crystallized twice from petroleum ether (30°–60°) at $-18°$; colorless prisms, 45% yield, m.p. 86.5°–88°. uv $\lambda$ max 221 nm ($\epsilon$12,100); sh 245 (5,600); sh 261 (3,250). ir NH/=CH 3280, 3080, 3060; N-alkyl 2780, 2760; C=O 1630; amide II 1560; C=C 1510; CF$_3$ 1325, 1125; CH=CH$_2$ 930; aromatic 860. nmr in CDCl$_3$ (100 MHz) was in accord. Mass spectrum M+ 340.

Anal. Calcd. for $C_{18}H_{23}F_3N_2O$: C, 63.15; H, 6.81; F, 16.75; N, 8.23. Found: C, 63.32; H, 6.41; F, 16.44; N, 8.48.

The salt was prepared with ethereal HCl and was crystallized from MeOH-ether, m.p. 200.5°–201.5°. uv $\lambda$ max 223 nm (ε 12,400); sh 268 (1,450). ir NH 3220; NH/=CH 3080, 3040; N+H 2620, 2500; C=O 1655; C=C 1620, 1580, 1515; amide II 1555; CF$_3$ 1335, 1315, 1120; CH=CH$_2$ 990, 930, 925; aromatic 860. nmr in D$_2$O (60 MHz) was in accord. Mass spectrum M+ 340.

Anal. Calcd. for $C_{18}H_{23}F_3N_2O\cdot HCl$: C, 57.37; H, 6.42; Cl, 9.41; F, 13.13; N, 7.44. Found: C, 56.95; H, 6.48; Cl, 9.35; F, 15.06; N, 7.34.

EXAMPLE 25 trans-N-[2-(N-Allyl-N-methylamino)cyclohexyl]-3,4-dichloro-benzamide fumarate

The titled amide was prepared by general procedure B from the Example 24(A) amine and 3,4-dichlorobenzoylchloride on a 0.0261 mole scale. CH$_2$Cl$_2$ was used for extraction and the crude product was chromatographed on 600 g. of silica gel using 1% meOH—CHCl$_3$. Fraction 1 (700 ml.) and fractions 2–56 (25 ml. each) gave a mobile oil (discarded). Fractions 57–98 (25 ml. each) gave a solid which was crystallized from ether to give colorless needles of the amide, m.p. 118.5°–119.5°, 4.27 g. (48% yield). uv λ max 205.5 nm (41,050); 237 (13,400); sh 279 (1,650); sh 288 (1,050). ir NH 3340; N-alkyl 2790, 2780; C=O 1635; C=C 1590, 1470; amide II 1555; C—N 1345; CH=CH$_2$ 920. nmr in CDCl$_3$ (100 MHz) was in accord. Mass spectrum M+ 340.

Anal. Calcd. for $C_{17}H_{22}Cl_2N_2O$: C, 59.82; H, 6.50; Cl, 20.78; N, 8.30. Found: C, 59.85; H, 6.68; Cl, 20.92; N, 8.30.

The amide salt was prepared with 1 mole of fumaric acid in MeOH-ether; colorless prisms, m.p. 185°–187° unchanged on recrystallization from MeOH-ether. uv λ max 205 nm (ε 56,000); 235 (15,950); sh 275 (2,000); sh 287 (1,050). ir NH 3280; N+H/acid OH 2440 broad; C=O/C=C/amide II/CO$_2$⁻ 1590, 1560, 1540 sh; C—N/other 1325, 1275, 1250, 1215, 1195; CH=CH$_2$ 975. nm in D$_6$DMSO and (60 MHz) was in accord. Mass spectrum M+ 340.

Anal. Calcd. for $C_{17}H_{22}Cl_2N_2O\cdot C_4H_4O_4$: C, 55.15; H, 5.73; Cl, 15.50; N, 6.13. Found: C, 55.38; H, 5.95; Cl, 15.83; N, 6.03.

EXAMPLE 26

Trans-N-[2-(N-allyl-N-methylamino)cyclohexyl]-α,α,α-trifluoro-N-methyl-p-toluamide A. trans-N-[N-methyl-N-allylamino)-cyclohexyl]formamide A solution of the Example 24 (A) diamine (10.46 g.; 0.062 mole) and 170 ml. of ethyl formate was refluxed 24 hours and evaporated. Distillation at 0.3 mm. gave 9.8 g. of the sub-titled formamide (80% yield), b.p. 116°–118°. ir NH 3280, 3060; CH 2920, 2860; N-alkyl 2780; C=O 1665; amide II 1540; other 1450, 1385, 1030; CH=CH$_2$ 915. nmr in CDCl$_3$ and 100 MHz was in accord. Mass spectrum M+ 196 (v. small).

Anal. Calcd. for $C_{11}H_{20}N_2O$: N, 14.27. Found: N, 14.04.

B. Reduction of N-[2-(N-methyl-N-allylamino)cyclohexyl]-formamide with LAH

The formamide from (A) above (9.7 g.; 0.0495 mole) was reduced with LAH according to general procedure C. The product was distilled at 13 mm; b.p. 104°–105°, 7.1 g. (79% yield). nmr in CDCl$_3$ and 100 MHz showed a mixture of trans-N,N′-dimethyl-N′-allylcyclohexanediamine and trans-N,N′-dimethyl-N′-propylcyclohexanediamine in a ratio of about 62:38. Mass spectrum M+ 184, 182.

C. trans-N-[2-(Allylmethylamino)cyclohexyl]-α,α,α-trifluoro-N-methyl-p-toluamide formrate (1:1) and trans-α,α,α-trifluoro-N-methyl-N-[2-(methylpropylamino)cyclohexyl]p-toluamide The reaction was run according to general procedure B using the diamine allyl-propyl mixture from step B above on a 5 mmole scale. The crude product (1.7 g.) was chromatographed on 170 g. of silica gel using 1% MeOH—CHCl$_3$ and collecting 25 ml. fractions. Fractions 1–35 gave no material. Fractions 36–41 gave 0.430 g. (pure by tlc) of the titled allyl compound. The salt was prepared with 1 mole of fumaric acid in MeOH-petroleum ether (30°–60°); 0.406 g., m.p. 133°–134° unchanged on recrystallization from MeOH-ether-petroleum ether. uv sh 206 nm (ε 28,200); sh 265 (2,250). ir N+H 2420; C=O/CO$_2$⁻/C=C 1695w, 1680w, 1640, 1620, 1550, 1525, 1490; CF$_3$/other 1330, 1175, 1125, 1075; aromatic 850. nmr in d$_6$DMSO (100 MHz) (heated at 100°) was in accord. Mass spectrum M+ 354.

Anal. Calcd. for $C_{19}H_{25}F_3N_2O\cdot C_4H_4O_4$: C, 58.71; H, 6.21; F, 12.12; N, 5.96. Found: C, 58.75; H, 6.22; F, 12.36; N, 5,97.

Fractions 42–57 gave 1.1 g. of a mixture. It was subjected to HPLC on a Merck prepacked silica gel size-C column using CHCl$_3$ and collecting 25 ml. fractions. Fractions 1–23 gave no material. Fractions 24–38 gave 0.225 g. of the allyl compound as an oil (pure by tlc). uv sh 235 nm (ε 5,300); sh 265 (2,100). ir =CH 3080; CH 2920, 2860; N-alkyl 2780; C=O 1635; C=C 1580, 1520; CH/CF$_3$ CN/other 1450, 1405, 1325, 1165, 1130, 1105, 1070; aromatic 855. nm in CDCl$_3$ showed absence of propyl absorption. Mass spectrum M+ 354 (no 356 present).

Anal. Calcd. for $C_{19}H_{25}F_3N_2O$: C, 64.39; H, 7.11; F, 16.08; N, 7.91. Found: C, 64.02; H, 6.80; F, 16.22; N, 7.85.

Fractions 39–65 gave 0.12 g. of a mixture of the two components (by tlc). Fractions 66–90 gave 0.538 g. of a mixture rich in the titled propyl compound (by tlc). Crystallization from petroleum ether (30°–60°) gave colorless prisms; 0.164 g. m.p. 85°–86.5° unchanged on recrystallization. uv sh 240 nm (ε 4,500); sh 264 (2,000). ir =CH 3060; N-alkyl 2760; C=O 1629; C=C 1580, 1520, 1500; other/CF$_3$ 1405, 1400, 1320, 1150, 1130, 1110, 1075, 1065, 1020; aromatic 860. nmr in CDCl$_3$ (100 MHz) showed propyl to allyl ratio of 81:19.

EXAMPLE 27 trans-N-[2-(allylmethylamino)cyclohexyl]-3,4-dichloro-N-methyl-benzamide methanesulfonate This titled amide base was prepared according to general procedure B from the amine prepared in Procedure IV and 3,4-dichlorobenzoylchloride. The product was crystallized from petroleum ether at −18°, colorless prisms, 77% yield, m.p. 92°–93°. uv sh 220 nm (ε 14,100); sh 230 (10,400); sh 273 (1,100); sh 281 (775). ir was in accord. nmr in CDCl$_3$ was in accord. Mass spectrum M+ 354.

Anal. Calcd. for $C_{18}H_{24}Cl_2N_2O$: C, 60.88; H, 6.81; Cl, 19.96; N, 7.89. Found: C, 60.88; H, 6.84; Cl, 19.66; N, 7.93.

The titled amide salt was prepared with 1 mole of methanesulfonic acid in MeOH-ether, and was recrystallized from MeOH-ether; m.p. 164°–165°. uv sh 220 nm (ε 13,350); sh 230 (10,500); sh 275 (903); sh 282 (664). ir was in accord. nmr in D$_2$O was in accord with the proposed structure. Mass spectrum M+ 354.

Anal. Calcd. for $C_{18}H_{24}Cl_2N_2O \cdot CH_3SO_3H$: C, 50.55; H, 6.25; Cl, 15.71; N, 6.21; S, 7.10. Found: C, 50.50; H, 6.03; Cl, 15.70; N, 6.09; S, 7.22.

EXAMPLE 28

Trans-3,4-dichloro-N-[2-(N'-ethyl-N'-methyl amino)-cyclohexyl]benzamide

A. trans-N-Ethyl N-methyl-1,2-cyclohexanediamine maleate

A mixture of 7-azabicyclo[4.1.0]heptane (9.71 g.; 0.1 mole), N-ethylmethylamine (11.82 g.; 0.2 mole), $NH_4Cl$ (0.18 g.) and 17.8 ml. of $H_2O$ was stirred at 95° for 22 hours. It was basified with solid NaOH, extracted with ether and the extract dried ($MgSO_4$) and evaporated. The desired amine product boiled at 50°-52° (0.5 mm); 4.6 g. (30% yield). ir NH 3360, 3270 sh; CH 2930, 2860, 2800; NH def. 1575; other 1450, 1055, 1040, 865. nmr in $CDCl_3$ (100 MHz) was in accord.

The titled salt was prepared with 2 moles of maleic acid in ether and crystallized from MeOH-ether; colorless prisms, m.p. 129°-130°. uv λ max 209 nm (ε 32,250). ir $N^+H$/acid OH~3000 broad, 2720; C=O 1705; $CO_2^-$/NH def.—/C=C/CN/other 1620, 1585, 1540, 1510, 1465, 1380, 1355, 1200, 1125, 995, 880, 860. nmr in $D_2O$ and 100 MHz was in accord. Mass spectrum M+ 156.

Anal. Calcd. for $C_8H_{20}N_2 \cdot 2C_4H_4O_4$: C, 52.57; H, 7.27; N, 7.21. Found: C, 52.41; H, 7.22; N, 7.18.

B. trans-N-[2-(ethylmethylamino)cyclohexyl]-3,4-dichloro-benzamide

This titled amide was prepared according to general procedure B from the above amine (A) and 3,4-dichlorobenzoyl chloride. The amide product was crystallized from ether, colorless needles, 52% yield, m.p. 111°-112° raised to 111.5°-112.5° on recrystallization. uv λ max 205 nm (ε 41,400); 237 (13,150); sh 276 (1,750); sh 286 (1,050). ir NH 3320 N-alkyl 2780; C=O 1636; C=C 1590; amide II 1540; C-N 1325, 1030; aromatic 835, 760. nmr in $CDCl_3$ (100 MHz) was in accord. Mass spectrum M+ 328.

Anal. Calcd. for $C_{16}H_{22}Cl_2N_2O$: C, 58.36; H, 6.74; Cl, 21.54; N, 8.51. Found: C, 58.22; H, 6.56; Cl, 21.50; N, 8.80.

EXAMPLE 29

Trans-3,4-dichloro-N-{2-[N-methyl-N-(2-phenylethylamino)cyclohexyl]}benzamide

A. trans-N-Methyl-N-phenylethyl-1,2-cyclohexanediamine, 2-naphthalene sulfonate (1:2)

A mixture of the aziridine 7-azabicyclo[4.1.0]heptane (9.7 g.; 0.1 mole), N-methylphenylethylamine (13.5 g.; 0.1 mole), $NH_4Cl$ (0.15 g.) and 4 ml. of $H_2O$ was stirred and heated at 95° for 18 hours. Solid NaOH was added and the mixture was extracted with ether. The extract was dried ($MgSO_4$) and evaporated. Two distillations gave 2.63 g., b.p. 114°-116° at 0.15 mm. When the reaction was repeated using 2 equivalents of N-methylphenylethylamine 3.26 g. of amine product was obtained. uv λ max 204 nm (ε 9,000); sh 247 (286); 252 (239); sh 254 (221); 258 (230); 261 (218); 263 (177); 267 (158). ir NH 3360, 3300; =CH 3020; CH 2920, 2850; N-alkyl 2790; C=C/NH def. 1605, 1585, 1495, 1450; C-N 1045; aromatic 745, 700. nmr in $CDCl_3$ (100 MHz) was in accord.

The salt of the amine was prepared with 2 moles of 2-naphthalene sulfonic acid in MeOH-ether. Crystallization from MeOH-ether gave tan rods, m.p. 224°-225°. uv sh 224 nm (ε 181,200); λ max 227 (218,450); 258 (7,800); 266 (9,750); 274 (10,300); sh 284 (7,000); sh 298 (1,000); 306 (967); 312 (805); 319.5 (967). ir $N^+H$~2950 broad, 2720, 2580; $N^+H_3$/C=C 1615, 1595, 1560, 1505; $SO_3^-$/other 1250, 1220, 1160, 1150, 1140, 1090, 1030; aromatic 820, 755; $SO_3^-$ 675. nmr in $d_6DMSO$ (100 MHz) was in accord.

Anal. Calcd. for $C_{15}H_{24}N_2 \cdot 2C_{10}H_8O_3S$: C, 64.79; H, 6.21; N, 4.32; S, 9.88. Found: C, 64.59; H, 6.30; N, 4.37; S, 10.12.

B. trans-3,4-Dichloro-N-[2-(methylphenylethylamino)-cyclohexyl]-benzamide

This titled amide was prepared by general procedure B using 3,4-dichlorobenzoyl chloride (2.2 g.; 0.0105 mole), the amine from part A above (2.43 g.; 0.0105 mole) and triethylamine (1.06 g.; 0.0105 mole). The crude solid was crystallized from MeOH, 2.43 g. (57% yield) of colorless needles; m.p. 119°-120° raised to 119.5°-121° on recrystallization. uv λ max 206 nm (ε 48,100); 236 (13,300); sh 276 (1,850); 286 (1,200). ir NH/=CH 3280, 3060; C=O 1625; C=C 1605, 1590, 1495; amide II 1540; aromatic 855, 725, 695. nmr in $CDCl_3$ (100 MHz) was in accord.

Anal. Calcd. for $C_{22}H_{26}ClN_2O$: C, 65.18; H, 6.47; Cl, 17.49; N, 6.91. Found: C, 64.81; H, 6.44; Cl, 17.96; N, 6.99.

EXAMPLE 30

Trans-N-[2-(dimethylamino)cyclohexyl]-N-ethyl-α,α,α-trifluoro-p-toluamide

A. trans-N-[2-(Dimethylamino)-cyclohexyl]-acetamide

This amide was prepared by general procedure A from trans-2-(dimethylamino)cyclohexylamine and acetyl chloride. In the work up the aqueous layer was salted out with solid $K_2CO_3$, and extracted well with ether. The resulting oil was crystallized from ether-petroleum ether (30°-60°) to give colorless rods of the sub-titled amide, 79% yield, m.p. 86°-87.5° raised to 88°-89° on recrystallization. ir NH 3280, 3080; N-alkyl 2770; C=O 1660, 1640; amide II 1565. nmr in $CDCl_3$ and 100 MHz was in accord. Mass spectrum M+ 184.

Anal. Calcd. for $C_{10}H_{20}N_2O$: C, 65.17; H, 10.94; N, 15.21. Found: C, 65.17; H, 10.82; N, 15.19.

B. The LAH reduction of this compound to N-ethyl-N-[2-(dimethylamino)cyclohexyl]amine proceeds as described under General Procedure C.

C. trans-N-[2-(Dimethylamino)cyclohexyl]-N-ethyl-α,α,α-trifluoro-p-toluamide

This titled amide was prepared by general procedure B from the above diamine and 4-trifluoromethylbenzoyl chloride. The titled amide was crystallized from petroleum ether (30°-60°) at −20°; 77% yield, m.p. 58.5°-60°. uv sh 214 nm (ε 10,350); sh 233 (4,900); sh 257 (2,400); sh 263 (1,850); sh 268.5 (1,500). ir N-alkyl 2780; C=O 1620, 1610; C=C 1575, 1515; $CF_3$/CN/other 1425, 1320, 1160, 1120, 1105, 1060, 1050; aromatic 860, 850, 840. nmr in $CDCl_3$ (100 MHz) was in accord. Mass spectrum M+ 342.

Anal. Calcd. for $C_{18}H_{25}F_3N_2O$: C, 63.14; H, 7.36; F, 16.65; N, 8.18. Found: C, 63.00; H, 7.28; F, 16.59; N, 7.89.

EXAMPLE 31 cis-N-[2-(dimethylamino)cyclohexyl]-α,α,α-trifluoro-o-toluamide hydrochloride

The amide base was prepared according to general procedure B from cis-2-N,N-dimethylaminocyclohexanediamine and 4-trifluoromethylbenzoyl chloride and was obtained as a yellow oil. uv (EtOH) λ max 221 nm (ε 11,300); ir NH 3340; =CH 3060; CH 2920, 2820; N-alkyl 2760; C=O 1640; C=C 1620, 1580, 1500; amid II 1535; CF$_3$/other 1330, 1165, 1130, 1070, 1020, 775; aromatic 860; nmr (CDCl$_3$) was in accord. Mass spectrum M+ 314.

Anal. Calcd. for C$_{16}$H$_{21}$N$_2$F$_3$O: C, 61.13; H, 6.73; N, 8.91. Found: C, 60.87; H, 6.90; N, 8.93.

The amide hydrochloride was prepared from excess ethereal HCl and recrystallized from MeOH-ether, m.p. 183°–184°; uv (EtOH) λ mass 223 nm (ε 11,750); 266 (sh 1350); ir NH 3220; =CH 3040, 3020; NH+ 2540, 2500, 2480, 2440; C=O 1655; C=C 1620, 1585, 1510, 1495; amide II 1535; CF$_3$/other 1330, 1165, 1110; aromatic 855; nmr (D$_2$O) was in accord. Mass spectrum M+ 314 (free base).

Anal. Calcd. for C$_{16}$H$_{21}$N$_2$F$_3$O.HCl: C, 54.77; H, 6.32; N, 7.99; Cl, 10.11; F, 16.25. Found: C, 54.57; H, 6.43; N, 7.94; Cl, 10.08; F, 16.37.

EXAMPLE 32 cis-N-[2-(dimethylamino)cyclohexyl]-α,α,α-tri-fluoro-N-methyl-p-toluamide

The titled amide was prepared according to procedure B from cis-N,N′,N′-trimethylcyclohexane diamine (prepared in procedure V-B) and 4-trifluoromethylbenzoyl chloride. The crude yellow oil was crystallized from pet. ether (b.p. 30°–60°) at −78°, m.p. 78°–79°; ur (EtOH) end absorption, λ max 215 nm (ε 10,250); 264 (sh 1850), 268 (sh 1550); ir N-alkyl 2760; C=O 1635; C=C 1580, 1525, 1495; CF$_3$/other 1325, 1320, 1200, 1165, 1135, 1110, 1075; aromatic 860; nmr (CDCl$_3$) was in accord. Mass spectrum M+ 328.

Anal. Calcd. for C$_{17}$H$_{23}$N$_2$F$_3$O: C, 62.18; H, 7.06; N, 8.53; F, 17.36. Found: C, 62.14; H, 7.15; N, 8.53; F, 17.38.

EXAMPLE 33 cis-3,4-Dichloro-N-[2-(dimethylamino)cyclopentyl]-N-methylbenzamide
Compounds With Cyclopentane Ring System A. 1-Dimethylamino-cyclopent-1-ene A solution of titanium tetrachloride (284 g., 1.50 mole) in 200 ml. petroleum ether (b.p. 30°–60°) was added in portions over 2.5 hours while cooling (<4°) to a solution of dimethylamine (406 g., 9.00 mole) and cyclopentanone (254 g., 3.00 mole) in 1000 ml. ether. The mixture was kept at room temperature overnight. The precipitate was collected and washed with ether. The ether was removed by distillation. The residual oil was distilled at reduced pressure to give, 285 g. (85% yield) of the titled enamine, b.p. 57°–58°. The nmr (CDCl$_3$) was in accord.

B. cis-2-(dimethylamino)-cyclopentane carboxylic acid

A solution of benzyl chloroformate (194 g., 1.14 mole) in 300 ml. benzene was added in 15 minutes to a solution of the part A enamine (254 g., 2.28 mole) in 1000 ml. benzene. The mixture was stirred 1 hour, then refluxed overnight. The precipitate was collected and washed with benzene. The combined filtrate was concentrated to 1000 ml., treated with 10 g. PtO$_2$, and hydrogenated at ∼1.7 mole). The mixture was filtered to remove insoluble material and evaporated to a brown oil (176 g.). The oil was dissolved in 1000 ml. ether, treated with 10 g. 10% Pd on carbon and hydrogenated until hydrogen uptake ceased (∼0.5 mole). The precipitate was collected and washed with ether. The precipitate was dissolved in chloroform and filtered to remove catalyst. The solution was evaporated. The residual oil was triturated with ether to induce crystallization of 52.5 g. of the titled acid, (29% yield), m.p. 82°–84° (very hygroscopic). An analytical sample obtained by recrystallization from chloroform-ether had m.p. 85°–87°. uv (EtOH) end absorption. ir OH/NH 3400; NH+ 2460, 2320; CO$_2$−/H$_2$O 1620; CH/CO$_2$− 1395. nmr (D$_2$O) was in accord. Mass spectrum M+ 157.

Anal. Calcd. for C$_8$H$_{15}$NO$_2$.¼H$_2$O: C, 59.41; H, 9.65; N, 8.66. Found: C, 59.40; H, 9.70; N, 8.59.

C. Curtius Reaction with cis-2-(dimethylamino)cyclopentone carboxylic acid

A solution of diphenyl phosphoryl azide (44.3 g., 0.16 mole) in 50 ml. benzene was added in 15 minutes to a solution of the part B amino acid (25.3 g., 0.16 mole) in 750 ml. benzene. After 15 minutes, triethyl amine (16.2 g., 0.16 mole) was added over 5 minutes. The solution was stirred for 30 minutes, then refluxed for 30 minutes. Benzyl alcohol (51.8 g., 0.48 mole) was added and the mixture refluxed overnight. The solution was extracted with 10% HCl. The aqueous layer was washed with ether, made basic with 40% NaOH, and extracted with ether. The ether layer was washed with water and saturated salt solution, dried (MgSO$_4$), and evaporated to a brown oil (7.9 g.). The nmr (CDCl$_3$) of the crude product was reasonable for a benzyl carbamate. The benzyl N-[2-(dimethylamino)cyclopentyl]carbamate material was used without purification.

D. cis-N,N-dimethyl-1,2-cyclopentanediamine

The benzyl carbamate obtained in the previous step C (7.9 g.,) was dissolved in 200 ml. ether, treated with 10% Pd on carbon (2.0 g.) and hydrogenated at ca 50 psi for 72 hours. The solution was filtered and the ether removed by distillation. The residue was distilled at reduced pressure to give 1.5 g., (7% overall yield) of the titled diamine, b.p. 90°–100°/30 mm. ir NH 3300; CH 2940, 2850; N-alkyl 2750; NH def 1590; CH 1460, 1440; CN/other 1350, 1265, 1200, 1140, 1105, 1070, 1040, 900; nmr (CDCl$_3$) was in accord. Mass spectrum M+ 128.

E. cis-N-[2-(Dimethylamino)-cyclopentyl]-formamide

A solution of the part D diamine (1.4 g., 10.9 mmole) in 100 ml. ethyl formate was refluxed overnight. The solution was evaporated to give 1.7 g. (100% yield) of the titled amide. The material was used in the next step without purification. ir NH 3300, CH 2940, 2850; N-alkyl 2750; C=O 1676; CH/other 1465, 1380, 1350, 1200, 1040, 915. nmr (CDCl$_3$) was in accord. Mass spectrum M+ 156.

F. cis-N,N,N′-Trimethyl-1,2-cyclopentanediamine

A solution of the formamide obtained in the previous step E (1.7 g., 10.9 mmole) in 50 ml. ether was added to a suspension of LAH (2.0 g.) in 100 ml. ether in 15 minutes. The mixture was refluxed overnight. The excess LAH was decomposed by addition of 2 ml. water, 2 ml. 15% NaOH, and 6 ml. water. The precipitate was collected and washed with ether. The combined filtrate was dried (MgSO$_4$) and the ether removed by distillation. The residual oil was distilled at reduced pressure to give 1.20 g. (77% yield) of the titled diamine, b.p. 82°–84°/27 nm. ir NH 3300; CH 2910, 2850; N-alkyl 2860; CH 1660, 1640; CN/other 1350, 1260, 1240, 1150, 1105, 1060, 1040, 910. nmr (CDCl$_3$) was in accord. Mass spectrum M+ 142.

G. cis-3,4-Dichloro-N-[2-(dimethylamino)-cyclopentyl]-N-methyl-benzamide

The titled amide base was prepared according to procedure B using the part F diamine (1.1 g., 7.7 mmole), triethylamine (0.77 g., 7.7 mmole), and 3,4-dichlorobenzoyl chloride (1.6 g., 7.7 mole) and was obtained as a yellow oil. The hydrochloride was obtained by treatment with excess ethereal HCl and recrystallized from MeOH-ether, 1.9 g. (79% yield), m.p. 227°–228°. uv (EtOH) λ max 203 nm (38,600), 230 (sh 9950), 275 (sh 848), 280 (668). nmr (D$_2$O) was in accord. Mass spectrum M+ 350.

Anal. Calcd. for C$_{15}$H$_{20}$Cl$_2$N$_2$O.HCl: C, 51.22; H, 6.02; Cl, 30.24; N, 7.97. Found: C, 51.22; H, 6.15; Cl, 30.36; N, 7.94.

EXAMPLE 34

Trans-3,4-dichloro-N-[2-(dimethylamino)-cyclopentyl]benzamide

A. trans-2-(Dimethylamino)-cyclopentanol fumarate (2:1)

A mixture of cyclopentene oxide (188 g., 2.24 moles) aqueous dimethylamine (40%, 750 ml., 6.67 moles) was stirred overnight (temperature rose to 45° after 1 hour then subsided). The solution was diluted with saturated NaCl solution (750 ml.) and extracted with ether. The extract was dried (MgSO$_4$) and the ether removed by distillation. The residual oil was vacuum distilled to give 276 g. (90%) of the titled amino alcohol, b.p. 98°–100°/14 mm; ur (EtOH) end absorption. ir OH 3370, 3200; N-alkyl 2780; CO 1045. nmr (CDCl$_3$) was in accord. Mass spectrum M+ 129.

This titled amino alcohol is reported in J. Amer. Chem. Soc., 78, 2482 (1956).

The fumaric acid salt was prepared in MeOH-ether and recrystallized from MeOH-ether, m.p. 149°–150°. uv (EtOH) λ max 208 nm (ε 10,850), 257 (sh, 876), 278 (sh, 383), ir OH/NH 2670, 2560, 2520, 2480; C=O 1720; CO$_2$−/C=C 1610, 1415; CO 1065, 1005; other 810, 680. nmr (D$_2$O) was in accord. Mass spectrum M+ (free base) 129.

Anal. Calcd. for C$_7$H$_{15}$NO.½C$_4$H$_4$O$_4$: C, 57.73; H, 9.15; N, 7.48. Found: C, 57.35; H, 9.03; N, 7.11.

B.  trans-N'-Benzyl-N,N-dimethyl-1,2-cyclopentanediamine maleate (1:2)

A solution of trans-2-(dimethylamino)cyclopentanol (19.4 g., 0.15 mole) in 25 ml. THF was added in 30 minutes to a stirred suspension of sodium hydride (6.3 g., 57% dispersion in mineral oil, 0.15 mole) in 75 ml. THF. The mixture was heated on a steam bath for 30 minutes, cooled in ice, and methane sulfonyl chloride (17.2 g., 0.15 mole) in 25 ml. THF added in 30 minutes. Benzylamine (32.2 g., 0.30 mole) was added in one portion. The solvent was removed by distillation, and the mixture heated on a steam bath overnight. The mixture was treated with 200 ml. 20% NaOH and heated 1 hour. The mixture was extracted with ether, and the organic layer was washed with water and extracted with 10% HCl. The aqueous layer was washed with ether, basified with 40% NaOH, and extracted with ether. The ether layer was washed with saturated salt solution, dried (MgSO$_4$) and evaporated. The residual oil was distilled at 0.1 mm. After a forerun of benzylamine, there was obtained 20.3 g. (62% yield) of the titled amine. The maleic acid salt of the amine was prepared in MeOH-ether and recrystallized from MeOH-ether, m.p. 127°–128°. uv (EtOH) λ max 208 nm (ε 38,750), 259 (sh, qual), 261 (1100), 266 (802). ir NH/OH 3020, 2690, 2650, 2570, 2380; C=O 1705; CO$_2$−/NH def/C=C 1620, 1545, 1520, 1475; CO$_2$−/other 1355, 1345, 1000, 980, 875, 860, 700. nmr was in accord. Mass spectrum M+ 218 (free base).

Anal. Calcd. for C$_{14}$H$_{22}$N$_2$.2C$_4$H$_4$O$_4$: C, 58.65; H, 6.71, N, 6.22. Found: C, 58.85; H, 6.75; N, 6.11.

C. trans-N,N-Dimethyl-1,2-cyclopentanediamine maleate (1:2)

The free part B amine (10.8 g., 0.05 mole) (obtained by basification of the maleic acid salt) was dissolved in 200 ml. EtOH, treated with 0.5 g. 10% Pd-C, and hydrogenated overnight. The mixture was filtered. Acetic acid (6.0 g., 0.10 mole) and 0.5 g. 10% Pd-C were added and the mixture hydrogenated overnight. The mixture was filtered and evaporated, treated with 25 ml. 40% KOH, and extracted with ether. The extract was dried (MgSO$_4$) and evaporated. The residue was dissolved in 100 ml. EtOH and 22.5 g., 70% HClO$_4$, treated with 0.9 g. 10% Pd-C and hydrogenated overnight. The mixture was filtered and evaporated. The residue was treated with 50 ml. 40% NaOH, filtered to remove precipitated KClO$_4$ and the precipitate washed with ether. The aqueous layer was extracted with the washing and with fresh ether. The extract was dried (MgSO$_4$) and evaporated. The residue was distilled at 42 mm Hg to give 3.8 g. (59% yield) of colorless oil diamine. The nmr (CDCl$_3$) was in accord. The titled maleic acid salt was prepared in MeOH-ether and recrystallized from MeOH-ether, m.p. 151°–152°. uv (EtOH) λ max (ε 32,150). ir OH/NH 3500, 3600; NH+/acid; OH 2950 broad, 2720; C=O 1700; CO$_2$−/C=C 1595, 1550, 1465, 1360; other 1015, 1000, 865, 720. nmr (D$_2$O) was in accord. Mass spectrum M+ 128 (free base).

Anal. Calcd. for C$_7$H$_{16}$N$_2$.2C$_4$H$_4$O$_4$: C, 49.99; H, 6.71; N, 7.78. Found: C, 50.08; H, 7.06; N, 7.74.

D.  trans-3,4-Dichloro-N-[2-(dimethylamino)-cyclopentyl]-benzamide

The amide was prepared according to general procedure B from the part C amine and 3,4-dichlorobenzoyl chloride. The crude product was crystallized from ether-petroleum ether (b.p. 30°–60°) to give the titled product D, (48% yield), m.p. 98°–99°. An analytical sample obtained by recrystallization from ether-petroleum ether had m.p. 99°–100°. uv (EtOH) λ max 207 nm (ε 36,500), 238 (12,800), 276 (sh, 1700), 286 (sh, 964). ir NH 3350; NH/=CH 3090; N-alkyl 2770; C=O 1635; C=C 1605, 1585, 1560; amide II 1535; other 1465, 1350, 1245, 1030, 905; arom CH/C—Cl 835, 830, 760. nmr (CDCl$_3$) was in accord. Mass spectrum M+ 300, M+ +2 302.

Anal. Calcd. for C$_{14}$H$_{18}$Cl$_2$N$_2$O: C, 55.82; H, 6.02; Cl, 23.54; N, 9.30. Found: C, 55.56; H, 5.89; Cl, 23.57; N, 9.14.

EXAMPLE 35

Trans-N-methyl-3,4-dichloro-N-[2-(dimethylamino)-cyclopentyl]benzamide

A. trans-N-Benzyl-N,N,N'-trimethyl-1,2-diaminocyclopentane

The amino alcohol cis-2-(dimethylamino)cyclopentanol (38.8 g., 0.30 mole) in 50 ml. THF was added in one portion to a stirred suspension of sodium hydride (12.6 g., 0.30 mole, 57% oil dispersion) in 150 ml. THF, and the mixture was heated on a steam bath for 1 hour. The solution was cooled in ice, and methanesulfonyl chloride (34.4 g., 0.30 mole) in 50 ml. THF was added in 30 minutes. N-methylbenzylamine (72.8 g., 0.60 mole,) was added in one portion. The solvent was removed by distillation and the residue heated overnight on a steam bath. The mixture was treated with 400 ml. 20% NaOH and heated 1 hour. The mixture was extracted with ether. The organic phase was extracted with 10% HCl. The aqueous phase was washed with ether, made basic with 40% NaOH, and extracted with ether. The ether extract was washed with saturated salt solution, dried (MgSO₄) and evaporated. The residual oil was distilled at 0.2 mm. After a forerum of N-methylbenzylamine, there was obtained 35.5 g. (51% yield) of a mixture of the titled N-methyl and N-H amines (~10:1 ratio of N-methyl to N-H amine by vpc), b.p. 115°–120°/0.2 mm.

B. trans-N,N,N'-Trimethyl-1,2-cyclopentanediamine

The mixture of amines obtained in the previous step A (32.0 g., 0.14 mole) was dissolved in 70% HClO₄ (63.0 g., 0.42 mole) and diluted to 200 ml. with EtOH. 10% Pd-C (4.0 g.) was added and the mixture hydrogenated overnight. The solution was filtered and evaporated. The residue was basified with 150 ml. 40% NaOH and the precipitated KClO₄ removed by filtration and washed with ether. The aqueous phase was extracted with the washings and with fresh ether. The combined ether extract was dried (MgSO₄) and the ether removed by distillation. Distillation at 30 mm gave 10.7 g. (54% yield) mixture of the titled trimethyl and dimethyl amines (~10:1 ratio by vpc). The p-toluenesulfonic acid salt of the trimethyl amine mixture was prepared in MeOH-ether and recrystallized from MeOH-ether. m.p. 144°–145°. uv (EtOH) λ max 222 nm (ε 22,850), 227 (sh, 15, 250), 244 (sh 238), 249 (sh, 326, 251 (sh, 370), 266 (491), 261 (579), 266 (423), 271 (sh, 243). ir OH (H₂O) 3460-3380; =CH 3040, 3020; NH⁺ 3030 br, 2800 br, 2800 br; NH def/C=C 1629, 1600, 1585, 1540, 1495; SO₃⁻/other 1230, 1215, 1180, 1125, 1035, 1015; para CH/SO₃⁻ $^{675}$; nmr (D₂O) was in accord. Mass spectrum M⁺ 142 (free base).

Anal. Calcd. for $C_8H_{18}N_2.2\ C_7H_8SO_3.\frac{1}{2}\ H_2O$: C, 53.30; H, 7.12; N, 5.65; S, 12.94. Found: C, 52.90; H, 7.45; N, 5.92; S, 12.95.

C. trans-N-methyl-3,4-dichloro-N-[2-(dimethylamino)-cyclopentyl]-benzamide hydrochloride The titled amide was prepared according to procedure B using the mixture of amines obtained in the previous step B (3.56 g., 0.025 mole), triethylamine (2.53 g., 0.025 mole) and 3,4-dichlorobenzoyl chloride (5.24 g., 0.025 mole). The crude product amide was treated with excess ethereal HCl and the salt recrystallized from MeOH-ether to give 5.1 g. (65% yield) of the titled amide (tlc of the free base showed the absence of the N-H amide), m.p. 234°–235°. uv (EtOH) end absorption, λ max 275 nm (sh, ε 1050). ir =CH 3100, 3060, 3020; NH⁺ 2560, 2960; C=O 1625; C=C 1585, 1555, 1490; CH/CN/other 1410, 1315, 1030, 895, 860, 760, 695. mmr (D₂O) was in accord. Mass spectrum M⁺ 313, M⁺ 2 315 (free base).

Anal. Calcd. for $C_{15}H_{20}Cl_2N_2O.HCl$: C, 51.22; H, 6.02; Cl, 30.24; N, 7.97. Found: C, 51.27; H, 5.97; Cl, 30.10; N, 8.04.

EXAMPLE 36

Trans-N-[2-(dimethylamino)cycloheptyl]-α,α,α-trifluoro-p-toluamide

A. trans-2-(Dimethylamino)-cycloheptanol fumarate hydrate

A mixture of cycloheptene oxide (89.0 g., 0.80 mole) and dimethylamine (275 ml., 40% aqueous, 2.4 mole) was heated in a rocking pressure bomb at 125° for 24 hours. The solution was saturated with 50 g. K₂CO₃ and 1 ml. 40% KOH and extracted with ether. The extract was dried (MgSO₄) and evaporated. The residual oil was distilled at 10 mm to give 114.6 g. (91% yield) of the titled amino alcohol base, b.p. 98°–100°. uv (EtOH) end absorption. ir OH 3420; CH 2930; N-alkyl 2780; CH 1460; CO 1085, 1045, 1020. nmr (CDCl₃) was in accord. Mass spectrum M⁺ 157.

Anal. Calcd. for $C_9H_{19}NO$: C, 68.74; H, 12.18; N, 8.91 Found: C, 68.48; H, 12.39; N, 8.53.

The fumaric acid salt was prepared in MeOH-ether and recrystallized from MeOH-ether, m.p. 136°–137°. uv (EtOH) λ max 207 nm (ε 8700). ir OH 3260; OH(-H₂O)/NH⁺/acid OH 2680, 2520, 2460; CO₂⁻/C=C 1575; CO₂⁻/CO/CN 1410, 1365, 1355; CO/other 1185, 1090, 1055, 1005, 995, 980, 810, 660. nmr (D₂O) was in accord. Mass spectrum M⁺ 157 (Free base).

Anal. Calcd. for $C_9H_{19}NO.\frac{1}{2}\ C_4H_4.\frac{1}{4}\ H_2O$: C, 60.10; H, 9.86; N, 6.37. Found: C, 60.29; H, 9.81; N, 6.11.

B. trans-N'-Benzyl-N,N-dimethyl-1,2-cycloheptanediamine dihydrochloride

A solution of the part A amino alcohol (39.3 g., 0.25 mole) in 50 ml. THF was added in one portion to a stirred suspension of sodium hydride (10.5 g., 57% dispersion in mineral oil, 0.25 mole) and the mixture heated on a steam bath for 1 hour. The solution was cooled in ice and methanesulfonyl chloride (28.6 g., 0.25 mole) added in 30 minutes. Benzylamine (53.6 g., 0.50 mole) was added in one portion. The solvent was removed by distillation and the residue was heated on a steam bath overnight. 300 ml. 20% NaOH was added and the heating continued for 1 hour. The mixture was extracted with ether. The extract was washed with water and extracted with 10% HCl. The aqueous phase was washed with ether, made basic with 20% NaOH, and extracted with ether. The organic phase was washed with water and saturated salt solution, dried (MgSO₄), and evaporated. The residual oil was distilled at 0.3 mm. After a forerun of benzylamine, 44.0 g. (71% yield) of the titled diamine base was obtained, b.p. 130°–136°/0.3 mm. uv (EtOH) end absorption, λ max 246 (ε 298) 252 (288), 257 (283), 263 (199), 266 (126), 272 (sh, 49), 78 (27). ir NH 3280; =CH 3080, 3060, 3020; CH 2920, 2850, 2820; N-alkyl 2770; C=C 1605, 1585, 1495; CH 1455; CN 1025; mono CH 735, 700. nmr (CDCl₃) was in accord. Mass spectrum M⁺ 246.

Anal. Calcd. for $C_{16}H_{26}N_2$: C, 77.99; H, 10.64; N, 11.37. Found: C, 77.78; H, 11.09; N, 11.08.

The dihydrochloride salt of the diamine was prepared from excess ethereal HCl and recrystallized from MeOH-ether, m.p. 225°–226°. uv (EtOH) λ max 205 nm (ε 9050), 242 (sh, 969), 248 (sh, 152), 252 (166), 257 (217), 261 (185), 263 (185), 267 (131). NMR (D₂C) was in accord. Mass spectrum M⁺ 246 (free base).

Anal. Calcd. for $C_{16}H_{26}N_2.2\ HCl$: C, 60.18; H, 8.84; Cl, 22.2; N, 8.76. Found: C, 60.09; H, 8.95; Cl, 22.55; H, 8.50.

C. trans-N,N-Dimethyl-1,2-cycloheptanediamine maleate (1:2)

A solution of the part B benzylamine (36.9 g., 0.15 mole) and 70% HClO₄ (67.5 g., 0.45 mole) in 200 ml. ethanol was hydrogenated overnight. The solution was evaporated and made basic with 150 ml. 40% KOH. The mixture was filtered to remove precipitated KClO₄. The precipitate was washed with ether. The filtrate was extracted with the washing and with fresh ether. The combined extract was dried (MgSO₄) and the ether removed by distillation. The residual oil was distilled at 14 mm to give 19.5 g. (83% yield) of the titled diamine, b.p. 94°–96°/14 mm. uv (EtOH) end absorption. ir NH 3360, 3300; CH 2920, 2860, 2820; N-alkyl 2770; NH def 1580; CH 1460; CN/other 1215, 1150, 1045, 1025, 885, 820. nmr (CDCl$_3$). Mass spectrum M+ 156.

Anal. Calcd. for $C_9H_{20}N_2$: C, 69.17; H, 12.90; N, 17.93. Found: C, 68.55; H, 12.92; N, 17.35.

The maleic acid salt of the titled diamine was prepared in MeOH-ether and recrystallized from MeOH-ether, m.p. 119°–120°. uv (EtOH) λmax 208 nm (32,7002). ir NH+/OH 3000 br, 2720, 2630; C═O/CO$_2$− NH$_3$+ 1685, 1610, 1590, 1530, 1505; other 1345, 1010, 975, 860, 720, 660. nmr (D$_2$O) was in accord. Mass spectrum M+ 156 (free base).

Anal. Calcd. for $C_9H_{20}N_2.2C_4H_4O_4$: C, 52.57; H, 7.27; N, 7.21. Found: C, 52.45; H, 7.40; N, 6.91.

D. trans-N-[2-(Dimethylamino)cycloheptyl]-α,α,α-trifluoro-p-toluamide

The titled amide was prepared according to general procedure B from the part C diamine and 4-trifluoromethylbenzoyl chloride. The amide product was recrystallized from ether-petroleum ether (b.p. 30°–60°); m.p. 91°–92°. uv (EtOH) λ max 221 nm (ε 11,600), 245 (sh, 5250), 255 (sh, 3750), 265 (sh, 2550). ir NH 3320; N-alkyl 2760; C═O 1635; C═C 1575, 1510; amide II 1545; aromatic/CN/other 1330, 1165, 1130, 855. nmr (CDCl$_3$) was in accord. Mass spectrum M+ 328.

Anal. Calcd. for $C_{17}H_{23}N_2F_3O$: C, 62.18; H, 7.06; F, 17.36; N, 8.53. Found: C, 62.37; H, 7.07; F, 17.60; N, 8.56.

EXAMPLE 37 trans-α,α,α-Trifluoro-N-[2-(dimethylamino)cycloheptyl]-N-methyl-p-toluamide oxalate (1:1)

A mixture of the trans-α,α,α-trifluoro-N-[2-(dimethylamino)cycloheptyl]-p-toluamide (3.28 g., 0.01 mole) and sodium hydride (0.42 g., 57% dispersion in mineral oil, 0.01 mole) in 50 ml. DMF was heated on a steam bath for 1 hour. The mixture was cooled to room temperature and methyl iodide (1.42 g., 0.01 mole) in 10 ml. DMF was added in 30 minutes. The mixture was stirred overnight at room temperature and the solvent was removed at reduced pressure. The residue was treated with 100 ml. water and 100 ml. methylene chloride. The organic phase was washed with water and saturated salt solution, dried (MgSO$_4$) and evaporated to 3.1 g. yellow oil. The oil was chromatographed on 300 g. silica gel eluting with 1% MeOH—CHCl$_3$ in 25 ml. fractions (1000 ml. forecut taken). Fractions 1–26 contained the bicyclic by-product amide α,α,α-trifluoro-N-(8-azabicyclo[5.1.0]octyl)p-toluamide. The solid was recrystallized twice from petroleum ether (b.p. 30°–60°) at −78°; 0.155 g. (6% yield), m.p. 64°–66°. uv (EtOH) λ max 229 nm (12,300), 237 (sh, 11,350), 245 (sh, 9.025). ir C═O 1665; C═C 1620, 1580, 1515; CF$_3$/other 1325, 1310, 1165, 1065; aromatic 865. nmr (CDCl$_3$) was in accord. Mass spectrum M+ 283.

Anal. Calcd. for $C_{15}H_{16}F_3NO$: C, 63.59; H, 5.65; F, 20.12; N, 4.95. Found: C, 63.99; H, 5.73; F, 19.95; N, 4.69.

Fractions 27–72 contained 1.1 g. yellow oil. The nmr (CDCl$_3$) was in accord with the titled amide base. The oxalic acid salt was prepared from an equimolar amount of oxalic acid (0.29 g., 3.2 mmole) in MeOH-ether and recrystallized from MeOH-ether to give 1.0 g. (25% yield) of the titled amide salt, m.p. 155°–156°. uv (EtOH) λ max 214 nm (ε 10.650), 235 (sh, 4650), 257 (sh, 2250), 264 (1650). ir NH+ 2720; C═O 1725 br, 1635; C═C 1610, 1570, 1515, 1495; CF$_3$/CN/other 1315, 1160, 1120, 1110, 1070, 1015; aromatic 855. nmr (D$_2$O) was in accord. Mass spectrum M+ 342 (free base).

Anal. Calcd. for $C_{18}H_{25}F_3N_2O.C_2H_2O_4$: C, 55.55; H, 6.29; F, 13.18; N, 6.48. Found: C, 55.68; H, 6.44; F, 13.41; N, 6.71.

EXAMPLE 38

Trans-N-[2-(dimethylamino)cyclooctyl]-α,α,α-trifluoro-p-toluamide

A. trans-2-(Dimethylamino)-cyclooctanol p-toluenesulfonate

A mixture of cyclooctene oxide (100 g., 0.80 mole) and dimethylamine (275 ml. 45% aqueous, 2.4 mole) in a rocking pressure bomb at 215° for 24 hours. The mixture was extracted with ether. The organic layer was extracted with 10% HCl. The aqueous phase was washed with ether, made basic with 40% KOH, and extracted with ether. The ether extract was dried (MgSO$_4$) and evaporated. The residual oil was distilled to give 68.6 g. (50% yield) of the sub-titled amino alcohol, b.p. 115°–118°/15 mm. uv (EtOH) end absorption. ir OH 3380; CH 2920, 2860; N-alkyl 2780; CH 1455; CO/CN 1070, 1035. nmr (CDCl$_3$) was in accord. Mass spectrum M+ 171.

Anal. Calcd. for $C_{10}H_{21}NO$: C, 70.12; H, 12.36; N, 8.18. Found: C, 70.45; H, 13.07; N, 8.26.

The titled p-toluenesulfonic acid salt of the amino alcohol base was prepared in MeOH-ether and recrystallized from MeOH-ether, m.p. 125°–126°. uv (EtOH) λ max 219 nm (sh, ε, 11.700), 227 (sh, 7950), 244 (sh, 124), 248 (158), 251 (sh, qual), 255 (237), 261 (275), 268 (206), 271 (sh, 120). ir OH 3300, NH+ 3100; C═C 1600, 1480; SO$_3$−/other 1230, 1195, 1185, 1115, 1035, 1010; Aromatic 815; SO$_3$− 675. nmr (D$_2$O) was in accord. Mass spectrum M+ 171 (free base).

Anal. Calcd. for $C_{10}H_{21}NO.C_7H_8SO_3$: C, 59.44; H, 8.51; N, 4.08; S, 9.34. Found: C, 59.09; H, 8.33; N, 4.17; S, 9.19.

B. trans-N′-Benzyl-N,N-dimethyl-1,2-cyclooctanediamine maleate (1:2)

The part A amino alcohol (63.6 g., C.37 mole) in 50 ml. THF was added in one portion to a stirred suspension of sodium hydride (15.6 g., 0.37 mole, 57% mineral oil dispersion) in 150 ml. THF and the mixture heated on a steam bath for 1 hour. The mixture was cooled in ice and methane sulfonyl chloride (42.4 g., 0.37 mole) in 50 ml. THF was added in 30 minutes. Benzyl amine (79.3 g., 0.74 mole) was added in one portion. The solvent was removed by distillation, and the residue was heated overnight on a steam bath. 300 ml. 40% NaOH was added and heating continued 1 hour. The mixture was extracted with 10% HCl. The aqueous phase was washed with ether, basified with 40% NaOH, and extracted with ether. The extract was washed with saturted salt solution, dried (MgSO$_4$) and evaporated. Vacuum distillation of the residual oil gave, after a forerun of benzylamine, 60.5 g. (63% yield) of the sub-titled damine base, b.p. 130°–135°/0.2 mm. uv (EtOH) λ max 247 nm (ε 292), 252 (274), 258 (273), 264 (196), 267 (125). ir NH 3280; ═CH 3080, 3060, 3020; CH 2920, 2860, 2820; N-alkyl 2780; C═C 1605, 1585, 1495; CH 1470, 1455; CN 1035; aromatic 730, 697. nmr (CDCl$_3$). Mass spectrum M+ 260.

Anal. Calcd. for $C_{17}H_{28}N_2$: C, 8.40; H, 10.84; N, 10.76. Found: C, 78.85; H, 11.31; N, 10.93.

The sub-titled maleic acid salt was prepared in MeOH-ether and recrystallized from MeOH-ether, m.p.

116°–118°. uv (EtOH) λ max 207 nm (47,050). ir =CH 3140; NH+/acid OH 2580, 2460; C=O 1700; CO₂⁻/C=C/NH def 1615, 1580, 1535; CO₂⁻ 1355; other/aromatic 875, 870, 750, 700. nmr (D₂O) was in accord. Mass spectrum M+ 260 (free base).

Anal. Calcd. for C₁₇H₂₅N₂.2 C₄H₄O₄: C, 60.96; H, 7.37; N, 5.69. Found: C, 61.66; H, 7.32; N, 5.74.

C. trans-N,N-Dimethyl-1,2-cyclooctanediamine p-toluenesulfonate (1:2)

The part B benzylamine (55.0 g., 0.21 mole) was treated with 70% HClO₄ (aqueous, 94.6 g., 0.63 mole) and diluted to 300 ml. with ethanol. 5 g. of 10% palladium on carbon was added and the mixture hydrogenated overnight (initial pressure 51.5 psi, final pressure 34.0 psi, 0.1 mole=8.4 psi). The mixture was filtered, evaporated to remove the ethanol and made basic with 200 ml. 40% KOH. The precipitated KClO₄ was filtered and washed with ether. The filtrate was extracted with the washings and with fresh ether. The combined extract was dried (MgSO₄) and the ether removed by distillation. Distillation at 13 mm gave 21.0 g. (59% yield) of the sub-titled diamine base, b.p. 113°–115°/13 mm. uv (EtOH) end absorption. ir NH 3360, 3300; CH 2920, 2860, 2820; N-alkyl 2780; NH def 1645, 1580; CH 1470, 1455, 1445; CN 1035. nmr (CDCl₃) was in accord with the expected structures. Mass spectrum M+ 170.

Anal. Calcd. for C₁₀H₂₂N₂: C, 70.52; H, 13.02; N, 16.45. Found: C, 70.67; H, 13.65; N, 16.55.

The sub-titled diamine di p-toluenesulfonic acid salt was prepared in MeOH-ether and recrystallized from MeOH-ether, m.p. 210°–211°. uv (EtOH) λ max 221 nm (ε 23,650), 227 (sh, 15,850), 251 (sh, 345), 256 (468), 262 (551), 268 (412), 271 (242). Ir NH+ 3000, 2660, 2600; NH₃+ 1635, 1545, C=C 1600; SO₃⁻/other 1230, 1165, 1125; aromatic 815; SO₃⁻ 685. nmr (D₂O) was in accord. Mass spectrum M+ 170 (free base).

Anal. Calcd. for C₁₀H₂₂N₂.2 C₇H₈SO₃: C, 56.00; H, 7.44; N, 5.44; S, 12.46. Found: C, 56.19; H, 7.64; N, 5.47; S, 12.35.

D. trans-N-[2-(Dimethylaminp)cyclooctyl]-α,α,α-trifluoro-p-tolueamide hydrochloride The titled amide base was prepared according to general procedure B from the part C diamine and 4-trifluoromethylbenzoyl chloride. The crude solid was recrystallized from petroleum-ether (b.p. 30°–60°) at −78°, m.p. 100°–101°. uv (EtOH) λ max 221 nm (ε 11,500), 245 (sh, 5350). ir NH 3240; =CH 3060; N-alkyl 2760; C=O 1635; amide 11/C=C 1565; CF₃ 1325, 1165, 1120; aromatic 855; nmr (CDCl₃) was in accord. Mass spectrum M+ 342.

Anal. Calcd. for C₁₈H₂₅N₂F₃O: C, 63.14; H, 7.36; F, 16.65; N, 8.18. Found: C, 63.12; H, 7.47; F, 16.83; N, 8.18.

The titled hydrochloride salt was prepared from the amide base by treatment with excess ethereal HCl and recrystallized from MeOH-ether, m.p. 215°–216°. uv (EtOH) λ max 224 nm (ε 12,600), 268 (sh, 1550), 280 (sh, 865). ir NH 3280; NH+ 2620, 2480; C=O 1660, 1635; C=C 1585, 1515; amide II 1560; CF₃/CN/other 1340, 1325, 1130; aromatic 860. nmr (D₂O) was in accord. Mass spectrum M+ 342 (free base).

Anal. Calcd. for C₁₈H₂₅N₂F₃O.HCl: C, 57.06; H, 6.92; Cl, 9.42; F, 15.04; N, 7.30. Found: C, 56.78; H, 6.97; Cl, 9.42; F, 15.24; N, 7.30.

EXAMPLE 39

Trans-N-[2-(dimethylamino)cyclooctyl]-α,α,α-trifluoro-N-methyltoluamide, and its oxalate salt A. trans-N-[2-(Dimethylamino)-cyclooctyl]-formamide A solution of the trans-2-(dimethylamino)cyclooctyl amine (10.0 g., 0.059 mole) in 100 ml. ethyl furmate was refluxed overnight, then evaporated. Distillation of the residual oil gave 10.3 g. (80% yield) of the subtitled amide, b.p. 125°–130°/0.25 mm. uv (EtOH) end absorption. ir NH 3280, 3040; CH 2920, 2860; N-alkyl 2780; C=O 1660; amide II 1540; CH 1470, 1445, 1385; CN 1270, 1255, 1050, 1030. nmr (CDCl₃) was in accord. Mass spectrum M+ 198.

Anal. Calcd. for C₁₁H₂₂N₂P: C, 66.62; H, 11.18; N, 14.13. Found: C, 65.42; H, 11.30; N, 13.82.

B. trans-N,N,N'-Trimethyl-1,2-cyclooctanediamine oxalate

A solution of the part A amide (10.0 g., 0.05 mole) in 50 ml. ether was added dropwise in 30 minutes to a suspension of lithium hydride (LAH) (10.0 g.) in 300 ml. ether. The mixture was refluxed overnight, cooled in ice, and the excess LAH decomposed by addition of 10 ml. water, 10 ml. 15% NaOH and 30 ml. water. The precipitate was collected and washed with ether. The combined filtrate was dried and the ether removed by distillation. The residual oil was distilled at reduced pressure to give 8.9 g. (96% yield) of the sub-titled diamine base, b.p. 113°–115°/13 mm. uv (EtOH) end absorption. ir NH 3320; CH 2920, 2860, 2820, 1470, 1450; N-alkyl 2780; CN/other 1145, 1040, 835, 790. nmr (CDCl₃) was in accord. Mass spectrum M+ 184.

Anal. Calcd. for C₁₁H₂₄N₂: C, 71.67; H, 13.12; N, 15.20. Found: C, 72.03; H, 13.48; N, 14.88.

The sub-titled oxalic salt of the diamine was prepared in MeOH-ether and recrystallized from MeOH-ether, m.p. 156°–157°. uv (EtOH) end absorption; ir NH+/acid OH 2660, 2460; CO₂⁻/C=O/NH def 1710, 1696, 1635, 1605, 1535, CO 1250, 1230, 1170; other 770, 720. nmr (D₂O) was in accord. Mass spectrum M+ 184 (free base).

Anal. Calcd. for C₁₁H₂₄N₂1-1/2 C₂H₂O₄: Found: C, 52.26; H, 8.45; N, 8.45.

C. trans-N-[2-(dimethylamino)cyclooctyl]-α,α,α-trifluoro-N-methyl-p-toluamide oxalate (1:1)

The amide was prepared according to general procedure B from the diamine (Part B, above) and 4-trifluoromethylbenzoyl chloride. The crude oil was crystallized from petroleum ether (b.p. 30°–60°) at −78°, m.p. 59°–61°. uv (EtOH) end absorption, λ max 245 mm (sh, ε 3700), 257 (sh, 2350), 262 (sh, 2000), 265 (sh, 1800), 270 (sh, 1500); ir N-alkyl 2780, 2760; C=O 1610; C=C 1580, 1525, 1495, 1330, 1170, 1125, 1080; aromatic 860, 845; nmr (CDCl₃) was in accord. Mass spectrum M+ 356.

Anal. Calcd. for C₁₉H₂₇N₂F₃O: C, 64.02; H, 7.64; F, 15.99; N, 7.86. Found: C, 63.60; H, 7.34; F, 16.82; N, 7.59.

The titled oxalic acid salt was prepared in MeOH-ether and recrystallized from MeOH-ether, m.p. 177°–178°. uv (EtOH) λ max 213 nm (sh, 11,300), 237 (sh, 4500), 255 (sh, 2300), 262 (sh, 1800), 268 (sh, 1450). ir NH+/acid OH 2660; C=O 1800, 1775; C=O/C=C-/CO₂⁻ 1695, 1630, 1620, 1580, 1555, 1520, 1490; CF₃/other 1325, 1110, 1070; other 705. nmr (D₂O) was in accord. Mass spectrum M+ 356 (free base).

Anal. Calcd. for C₁₉H₂₇N₂F₃O.C₂H₂O₄: C, 56.49; H, 6.55; F, 12.77; N, 6.28. Found: C, 56.28; H, 6.48; F, 12.83; N, 6.48.

EXAMPLE 40

Following the procedure of Example 1b, using trans-2-(N-pyrrolidinyl)cyclohexylamine and 4-azidobenzoyl chloride there is obtained as product trans-N-[2-(N-pyrrolidinyl)cyclohexyl]-4-azidobenzamide.

EXAMPLE 41

Following the procedure of Example 1b, using trans-N-methyl-N-[2-(N'-piperidinyl)]cyclopentylamine and 4-phenylbenzoyl chloride there is obtained as product trans-N-methyl-N-[2-(N'-piperidinyl)cyclopentyl]-4-phenylbenzamide.

EXAMPLE 42

Following the procedure of Example 1b, using trans-N-methyl-N-[2-N-methyl-N'-(2-trifluoroethyl)-amino]-cyclohexylamine and 4-sulfobenzoyl chloride there is obtained as product trans-N-methyl-N-[2-N'-methyl-N'-(2-trifluoroethyl)aminocyclohexyl]-4-sulfobenzamide.

EXAMPLE 43

Following the procedure of Example 1b, using cis-N-methyl-N-[2-(N-pyrrolidinyl)]cycloheptylamine and 3,4-dibromobenzoyl chloride there is obtained as product cis-N-methyl-N-[2-(N-pyrrolidinyl)cycloheptyl]-3,4-dibromobenzamide.

EXAMPLE 44

Following the procedure of Example 1b, using trans-N-methyl-N-[2-N-methyl-N-(2-hydroxyethyl)amino]-cyclohexylamine and 2-naphthoyl chloride there is obtained as product trans-N-methyl-N-[2-N'-methyl-N'-(2-hydroxyethyl)amino]cyclohexyl-2-naphthamide.

EXAMPLE 45

Following the procedure of Example 1b, using cis-N-methyl-N-[2-(3-hydroxy-1-pyrrolidinyl)]cyclohexylamine and 3,4-difluorobenzoyl chloride there is obtained as product cis-N-methyl-N-[2-(3-hydroxy-1-pyrrolidinyl)cyclohexyl]-3,4-difluorobenzamide.

EXAMPLE 46

Following the procedure of Example 1b, using trans-N-[2-(4-methoxy-1-piperidinyl)cyclopentyl]amine and 3-methoxy-4-chlorobenzoyl chloride there is obtained as product trans-N-[2-(4-methoxy-1-piperidinyl)cyclopentyl]-3-methoxy-4-chlorobenzamide.

EXAMPLE 47

Following the procedure of Example 1b, using cis-N-[2-(3-acetyloxy-1-pyrrolidinyl)cyclohexyl]amine and 3,5-dimethylbenzoyl chloride there is obtained as product cis-N-[2-(3-acetyloxy-1-pyrrolidinyl)cyclohexyl]-3,5-dimethylbenzamide.

EXAMPLE 48

Following the procedure of Example 1b, using trans-N-methyl-N-[2-(N'-methyl-N'-cyclobutylmethylamino)]cyclohexylamine and 1-naphthoyl chloride there is obtained as product trans-N-methyl-N-[2-(N'-methyl-N'-cyclobutylmethylamino)cyclohexyl]-1-naphthamide.

EXAMPLE 49

Following the procedure of Example 1a, using trans-N-methyl-N-[2-(3-hydroxy-1-pyrrolidinyl)cyclohexyl]amine, carbonyldiimidazole and 3,4-dichlorobenzoic acid there is obtained N-methyl-N-[2-(3-hydroxy-1-pyrrolidinyl)cyclohexyl]-3,4-dichlorobenzamide.

EXAMPLE 50

Following the procedure of Example 1b, using trans-N-methyl-N-[2-(N-dimethylamino)cyclododecyl]amine and 4-trifluoromethylbenzoyl chloride there is obtained N-methyl-N-[2-(dimethylamino)cyclododecyl]-4-trifluoromethylbenzamide, m.p. 69°–70°.

Anal. Calcd. for $C_{23}H_{35}F_3N_2O$: C, 66.96; H, 8.55; N, 6.79; F, 13.82. Found: C, 66.87; H, 8.64; N, 6.91; F, 14.26.

EXAMPLE 51

Following the procedure of Example 1b, using trans-N-methyl-N-[2-(N'-pyrrolidinyl)]cyclohexylamine and 3,4-dichlorobenzoyl chloride there is obtained trans N-methyl-N-[2-(N'-pyrrolidinyl)cyclohexyl]-3,4-dichlorobenzamide.

In addition, by procedures described above, the following additional compounds were prepared:

(a) N-methyl-N-[2-(N'-methylamino)cyclohexyl]-4-trifluoromethylbenzamide, (m.p. 83°–84°);

(b) N-methyl-N-[2-(N',N'-dimethylamino)cyclohexyl]-3-bromo-4-methoxybenzamide (m.p. 147°–48°);

(c) N-methyl-N-[2-(N'-methyl-N'-cyclobutylmethylamino)cyclohexyl]-4-trifluoromethyl benzamide (m.p. 208°–9°);

(d) N-isopropyl-N-[2-(N',N'-dimethylamino(cyclohexyl]-4-trifluoromethylbenzamide, (m.p. 259°–60°) as the HCl;

(f) N-methyl-N-[2-(N'-pyrrolidinyl)cyclohexyl]-4-azidobenzamide (m.p. 91°–92°);

(g) N-methyl-N-[2-(N',N'-dimethylamino)cyclohexyl]-4-methoxybenzamide (m.p. 196°–98°, as the ptsa salt);

(h) N-methyl-N-[2-(N',N'-dimethylamino)-cyclohexyl]-3-bromo-4-hydroxybenzamide (m.p. 184°–85°);

(i) N-methyl-N-[2-(N'-methylamino)cyclohexyl]-3,4-dichlorobenzamide (m.p. 80°–81°);

(j) N-[2-(N',N'-diethylamino)cyclohexyl]-3,4-dichlorobenzamide (m.p. 103°–04°);

(k) N-methyl-N-[2-(N',N'-dimethylamino)cyclohexyl]-2-methyl-4-allyloxybenzamide (m.p. 50°–51°);

(l) N-methyl-N-[2-(N',N'-diethylamino);cyclohexyl]-3,4-dichlorobenzamide (m.p. 89°–90.5°);

(m) N-methyl-N-[2-(3-hydroxy-N'-pyrrolidinyl)cyclohexyl]-3,4-dichlorobenzamide (m.p. 116°–17°);

(n) N-methyl-N-[2-(N',N,-dimethylamino)cyclohexyl]-4-phenylbenzamide;

(o) N-methyl-N-[2-(N'-butyl-N'-methylamino)cyclohexyl]-3,4-dichlorobenzamide;

(p) N-methyl-N-[2-(N',N'-dimethylamino)cyclohexyl]-4-cyanobenzamide (m.p. 130°–31°);

(q) N-methyl-N-[2-(N'-2-hydroxyethyl-N'-methylamino)cyclohexyl]-4-trifluorobenzamide (m.p. 88°–89°);

(r) N-methyl-N-[2-(N',N'-dimethylamino)cyclohexyl]-2,6-dimethyl-4-methoxybenzamide (m.p. 105°–06°);

(s) N-methyl-N-[2-(N',N,-dimethylamino)cyclohexyl]-2-naphthamide (m.p. 125°–26°);

(t) N-methyl-N-[2-(N',N,-dimethylamino)cyclohexyl]-2,6-dimethyl-4-allyloxybenzamide;

(u) N-methyl-N-[2-(N',N-dimethylamino)cyclohexyl]-3,4-dichlorobenzamide;

(v) N-methyl-N-[2-(N',N'-dimethylamino)cyclohexyl]-4-chlorobenzamide;

(w) N-methyl-N-[2-(N'-methyl-N-2-phenylethylamino)-cyclohexyl]-4-bromo-benzamide;

(x) N-methyl-N-[2-(N',N,-dimethylamino)cyclohexyl]-4-azidobenzamide;

EXAMPLE 52

One thousand tablets for oral use, each containing 40 mg. of trans-N-methyl-N-[2-(N'-pyrrolidinyl)cyclohexyl]-4-trifluoromethylbenzamide as the essential active ingredient are prepared from the following ingredients:
Essential active ingredient: 40 gm.
Dicalcium phosphate: 150 gm.
Methylcellulose, U.S.P. (15 cps): 6.5 gm.
Talc: 20 gm.
Calcium stearate: 2.0 gm.

The essential active ingredient and dicalcium phosphate are mixed well, granulated with 7.5% aqueous solution of methylcellulose, passed through a No. 8 screen and dried carefully. The dried granules are passed through No. 12 screen, mixed with the talc and stearate and compressed into tablets. These tablets are useful in the treatment of pain in adult humans at a dose of 1 tablet 1 to 4 times a day as needed.

EXAMPLE 53

One thousand two-piece hard gelatin capsules for oral use, each capsule containing 20 mg. of trans-N-methyl-N-[2-(N',N,-dimethylamino-cyclohexyl]-4-azidobenzamide hydrochloride as the essential active ingredient are prepared from the following ingredients:
Essential active ingredient: 20 gm.
Lactose, U.S.P.: 100 gm.
Starch, U.S.P.: 10 gm.
Talc, U.S.P.: 5 gm.
Calcium stearate: 1 gm.

The finely powdered materials are mixed thoroughly, then filled into hard gelatin capsules of appropriate size.

One capsule 4 times a day is useful for the treatment of pain in adult humans.

EXAMPLE 54

One-piece soft elastic capsules for oral use, each containing 100 mg. of trans-N-methyl-N-[2-(N',N'-dimethylamino)cyclohexyl]-2,6-dimethyl-4-methoxybenzamide as the essential active ingredient are prepared in the usual manner by first dispersing the powdered active material in sufficient corn oil to render the material capsulatable.

One capsule 2 times a day is useful in the treatment of pain in adult humans.

EXAMPLE 55

An aqueous oral preparation containing in each teaspoonful (5 ml.) 80 mg. of trans-N-methyl-N-[2-N',N'-dimethylamino-cyclohexyl]-2-(3,4-dichlorobenzamide)-hydrochloride as the essential active ingredient is prepared from the following ingredients:
Essential active ingredient: 160 gm.
Methylparaben, U.S.P.: 7.5 gm.
Propylparaben, U.S.P.: 2.5 gm.
Saccharin Sodium: 12.5 gm.
Glycerin: 3,000 ml.
Tragacanth powder: 10 gm.
Orange oil flavor: 10 gm.
Orange II dye: 7.5 gm.
Deionized water, q.s. to: 10,000 ml.

The foregoing aqueous preparation is useful in the treatment of adult pain at a dose of 1 teaspoonful 4 times a day.

EXAMPLE 56

One thousand tablets for oral administration, each containing 10 mg. of trans-N-methyl-N-[2-(N',N,-dimethylamino)cycloheptyl]-4-azidobenzamide hydrochloride as the essential active ingredient and 16.2 mg. of phenobarbital are prepared from the following ingredients:
Essential active ingredient, micronized: 10 gm.
Phenobarbital: 16.2 gm.
Lactose: 150 gm.
Starch: 15 gm.
Magnesium stearate: 1.5 gm.

The ingredients are thoroughly mixed and slugged. The slugs are broken down by forcing through a screen and the resulting granules are then compressed into tablets.

These tablets are useful in reducing post-surgical pain in dogs at a dose of 1 to 3 tablets depending on the weight of the animal and its condition.

EXAMPLE 57

A sterile aqueous suspension suitable for intramuscular injection and containing in each milliliter 50 mg. of the Example 54 essential active ingredient is prepared from the following ingredients:
Essential active ingredient: 5 gm.
Polyethylene glycol 4000, U.S.P.: 3 gm.
Sodium chloride: 0.9 gm.
Polysorbate 80, U.S.P.: 0.4 gm.
Sodium metabisulfite: 0.1 gm.
Methylparaben, U.S.P.: 0.18 gm.
Propylparaben, U.S.P.: 0.02 gm.
Water for injection, q.s. to: 100 ml.

The preceding sterile injectable is useful in the treatment of pain at a dose of ½ to 2 ml.

EXAMPLE 58

One thousand suppositories, each weighing 2.5 gm. and containing 50 mg. of N-methyl-N-{2-[N'-methyl-N'-2-hydroxyethyl)amino]cyclohexyl}-4-trifluoromethylbenzamide as the essential active ingredient, are prepared from the following ingredients:
Essential active ingredient: 150 gm.
Propylene glycol: 165 gm.
Polyethylene glycol 4000 q.s.: 2,500 gm.

The essential active ingredient is added to the propylene glycol and the mixture milled until uniformly dispersed. The PEG 4000 is melted and the propylene glycol dispersion added. The suspension is poured into molds and allowed to cool and solidify.

These suppositores are useful in the treatment of post-surgical pain at a dose of 1 suppository rectally twice a day.

EXAMPLE 59

One thousand hard gelatin capsules for oral use, each containing 20 mg. of the Example 56 essential active ingredient and 40 mg. ketazolam are prepared from the following ingredients:
Essential active ingredient, micronized: 20 gm.
Ketazolam: 40 gm.
Starch: 125 gm.
Talc: 25 gm.
Magnesium stearate: 1.5 gm.

One capsule 4 times a day is useful in the relief of pain in adult humans.

EXAMPLE 60

Ten thousand scored tablets for oral use, each containing 80 mg. of N-methyl-N-[2-(N',N-dimethylamino)cyclohexyl]-4-methoxybenzamide as the essential active ingredient and 32 mg. of caffeine are prepared from the following ingredients:
Essential active ingredient, micronized: 800 gm.
Caffeine: 320 gm.
Lactose: 1,500 gm.
Corn starch: 500 gm.
Talc: 500 gm.
Calcium stearate: 25 gm.

The ingredients are thoroughly mixed and slugged. The slugs are broken down by forcing through a number 16 screen. The resulting granules are then compressed into tablets each containing 80 mg. of the acetamide derivative essential active ingredient and 32 mg. of caffeine.

This combination of active materials is effective in reducing pain in adult humans. The dose is one-half of two tablets 3 times a day, depending on the severity of the condition.

EXAMPLE 61

Ten thousand tablets for oral use, each containing 60 mg. of trans-N-methyl-N[2-(N'methyl-N'-allylamino)-cyclohexyl]-4-trifluoromethylbenzamide as the essential active ingredient and 0.5 mg. of methyl prednisolone are prepared from the following ingredients using the procedure described in Example 60.
Essential active ingredient, micronized: 600 gm.
Methylprednisolone: 5 gm.
Lactose: 1,000 gm.
Corn starch: 500 gm.
Talc: 500 gm.
Calcium stearate: 25 gm.

These tablets are useful in treating adult humans suffering from arthritic pain by administering 1 tablet 3 times a day.

EXAMPLE 62

Ten thousand tablets for oral use, each containing 5 mg. of cis-N-methyl-N-[2-(N',N'-dimethylamino)cyclopentyl]-3,4-dichlorobenzamide hydrochloride as the essential active ingredient and 320 mg. acetaminophen, are prepared from the following ingredients and using the procedure of Example 60.
Essential active ingredient, finely powdered: 50 gm.
Acetaminophen, finely powdered: 3,200 gm.
Corn starch: 500 gm.
Talc: 500 gm.
Calcium stearate: 50 gm.

This tablet is useful in treating homotopic pain or headache in an adult patient by administering one or two tablets 3 times a day depending on the severity of the condition.

In similar formulations the acetaminophen can separately be replaced by aspirin (320 mg./tablet) or Phenacetin-Aspirin-Caffeine (P-A-C) compound (390 mg./tablet).

EXAMPLE 63

One thousand tablets for oral use, each containing 110 mg. of N-methyl-N-[2-(N'-pyrrolidinyl)-cyclohexyl]-4-trifluoromethylbenzamide as an essential active ingredient and 400 mg. of chlorophenesin carbamate (Maolate) are prepared from the following ingredients:

Essential active ingredient, micronized: 110 gm.
Maolate: 400 gm.
Lactose: 50 gm.
Starch: 15 gm.
Magnesium stearate: 1.5 gm.

The ingredients are thoroughly mixed and slugged. The slugs are broken down by forcing through a screen and the resulting granules are then compressed into tablets.

These tablets are useful in reducing pain and muscle spasms at a dose of 1 tablet one to 3 times per day, depending upon the severity of the condition.

EXAMPLES 64 to 87

Following the procedures of the preceding Examples 52 to 63, inclusive, similar dosage forms of other formula I compounds can be prepared by substituting an equivalent amount of the following compounds as the essential active ingredients; it is understood that these compounds can be the optically active or racemic cis or trans stereoisomers:

(64) N-[2-(N',N'-dimethylamino)cyclohexyl]-4-trifluoromethylbenzamide;
(65) N-[2-(N',N'-dimethylamino)cyclohexyl]-4-nitrobenzamide;
(66) N-[2-(N',N'Δdimethylamino)cyclohexyl]-4-bromobenzamide;
(67) N-methyl-N-[2-(N',N'-dimethylamino)cyclohexyl]-4-bromobenzamide;
(68) N-methyl-N-[2-(N',N'-dimethylamino)cyclohexyl]-4-acetylbenzamide;
(69) N-methyl-N-[2-(N',N'-dimethylamino)cyclohexyl]-3-methoxy-4-nitrobenzamide;
(70) N-methyl-N-[2-(N',N'-dimethylamino)cyclohexyl]-4-trifluoromethylbenzamide;
(71) N-[2-(N'-allyl-N'-methylamino)cyclohexyl]-3,4-dichlorobenzamide;
(72) N-methyl-N-[2-(N'-methyl-N'-n-propylamino)cyclohexyl]-4-trifluoromethylbenzamide;
(73) N-ethyl-N-[2-(N',N'-dimethylamino)cyclohexyl]-4-trifluoromethylbenzamide;
(74) N-[2-(N'-N,-dimethylamino)cycloheptyl]-4-trifluoromethylbenzamide;
(75) N-methyl-N-[2-(N',N'-dimethylamino)cycloheptyl]-4-trifluoromethylbenzamide;
(76) N-methyl-N-[2-(N',N,-dimethylamino)cyclooctyl]-4-trifluoromethylbenzamide;
(77) N-[2-(N',N'-dimethylamino)cyclooctyl]-4-trifluoromethylbenzamide;
(78) N-methyl-N-[2-(N',N'-dimethylamino)cyclohexyl]-4-nitrobenzamide;
(79) N-methyl-N-[2-(N',N'-dimethylamino)cyclohexyl]-4-methanesulfonylbenzamide;
(80) N-methyl-N-[2-(N',N'-dimethylamino)cyclohexyl]-3-bromo-4-hydroxybenzamide;
(81) N-methyl-N-[2-(N-methylamino)cyclohexyl]-4-trifluoromethylbenzamide;
(82) N-methyl-N-[2-(N'-methyl-N'-cyclobutylmethylamino) cyclohexyl]-4-trifluoromethylbenzamide;
(83) N-methyl-N-{[2-N'-methyl-N'-(3-methyl-2-butenyl)amino]cyclohexyl}-4-trifluoromethylbenzamide;
(84) N-methyl-N-[2-(N',N'-dimethylamino)cyclohexyl]-4-methoxybenzamide;
(85) N-methyl-N-[2-(N'-dimethyl-N'-butylamino)cyclohexyl]-3,4-dichlorobenzamide;
(86) N-methyl-N-[2-(N'-methyl-N'-butylamino)cyclohexyl]-4-cyanobenzamide; or

(87) N-methyl-N-[2-(N',N'-dimethylamino)cyclohexyl]-2-naphthamide.

EXAMPLE 88

One thousand grams of ointment for topical use, each gram containing 20 mg. of trans-N-[2-(N',N'-dimethylamino)cycloheptyl]-4-azidobenzamide as the essential active ingredient is prepared from the following ingredients:
Essential active ingredient: 20 gm.
Spermaceti: 115 gm.
White wax: 110 gm.
Mineral oil: 560 gm.
Sodium borate: 5 gm.
Purified water g.s. to: 1,000 gm. (190 ml)
Apply to site of pain 5 to 6 times daily.

Although not necessary in the embodiments of the inventive concept, additional active ingredients can be incorporated in the present pharmaceutical dosage unit forms as desired. For example, each pharmaceutical dosage unit form may contain therein an amount within the following non-toxic effective ranges: tranquilizers, anti-psychotic and anti-anxiety agents, such as, chlorpromazine (5 to 50 mg.), thioridazine (5 to 100 mg.), haloperidol (0.5 to 5 mg.), meprobamate (100 to 400 mg.), chlordiazepoxide (5 to 50 mg.), diazepam (2 to 15 mg.), triazolam (.025 to 1 mg.), ketazolam (5 to 300 mg.), and ectylurla (100 to 300 mg.); barbiturates, such as phenobarbital (8 to 60 mg.), butabarbital (8 to 60 mg.), and amobarbital (16 to 120 mg.); analgesics, antipyretics-anti-inflammatories, such as, aspirin (150 to 600 mg.), flurbiprofen (20 to 200 mg.), ibuprofen (2 to 400 mg.), naproxen (20 to 200 mg.), indomethacin (20 to 200 mg.), and acetaminophen (150 to 600 mg.); and antidepressants, such as, amitriptyline hydrochloride (10 to 50 mg.), methylphenidate hydrochloride (5 to 20 mg.), d-amphetamine sulfate (2 to 15 mg.), methamphetamine hydrochloride (2 to 15 mg.), depending upon the condition being treated.

What is claimed is:

1. A compound of the formula

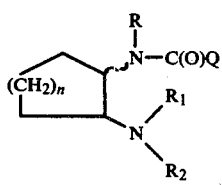   I wherein
the wavy line (∼) at the 1-position of the cycloaliphatic ring denotes trans-stereoconfiguration of the 1-position substituent with respect to the substituent in position 2 of the same cycloaliphatic ring; n is 1 to 8;
R is hydrogen or $C_1$ to $C_3$-alkyl;
$R_1$ and $R_2$, taken separately, are hydrogen, $C_1$ to $C_3$-alkyl, or when $R_1$ is hydrogen or $C_1$ to $C_3$-alkyl, $R_2$ is $C_1$ to $C_6$-alkyl, $CH_2CF_3$, -$C_3$ to $C_6$-(allylic-)alkenyl, a group of the formula

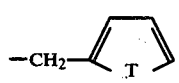

wherein T is —O— or —S—; $C_2$ to $C_5$-hydroxyalkyl, phenyl-$C_2$ to $C_3$-alkyl, $C_3$ to $C_6$-cycloalkyl, $C_3$ to $C_4$-cycloalkylmethyl, or $R_1$ and $R_2$, taken together with the nitrogen to which they are bonded, complete an azetidinyl, pyrrolidinyl, piperidinyl, or piperizinyl ring group, or an azetidinyl or pyrrolidinyl ring group substituted in the 3-position with hydroxy, $C_1$ to $C_3$-alkyl, $C_1$ to $C_3$-alkyloxy, $C_1$ to $C_3$-alkanoyloxy, a piperidinyl ring group substituted in the 3- or 4- position with hydroxy, $C_1$ to $C_3$-alkyl, $C_1$ to $C_3$ alkyloxy, or $C_1$ to $C_3$-alkanoyloxy or a piperazinyl ring group substituted on the p-nitrogen thereof with $C_1$ to $C_3$-alkyl,
Q is the radical

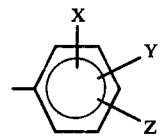

wherein one of X, Y and Z is azido, and the remaining X, Y and Z moieties are hydrogen, and the pharmaceutically acceptable salts thereof.

2. A compound according to claim 1 wherein the compound n is 1 to 4;
R is $C_1$ to $C_3$-alkyl;
$R_1$ and $R_2$ are each $C_1$ to $C_3$-alkyl; and
Q is

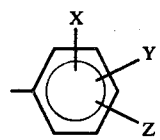

wherein X is azido and Y and Z are hydrogen, and the pharmaceutically acceptable salts thereof.

3. A compound according to claim 2 wherein the compound is trans-N-methyl-N-[2-(N',N'-dimethylamino)cycloheptyl]-4-azidobenzamide, and the pharmaceutically acceptable salts thereof.

4. A compound according to claim 2 wherein the compound is trans-N-methyl-N-[2-(N',N'-dimethylamino)cyclohexyl]-4-azidobenzamide, and the pharmaceutically acceptable salts thereof.

5. A composition useful in pharmaceutical dosage unit form in an amount ranging from about 0.5 to about 350 mg. per dosage unit for alleviating pain in warm blooded animals which comprises a compound of Formula I of claim 1 in combination with a pharmaceutically acceptable carrier.

6. A composition according to claim 5 wherein the compound of formula I is a compound of claim 2.

7. A composition according to claim 6 wherein the compound of formula I is a compound of claim 3.

8. A composition according to claim 6 wherein the compound of formula I is a compound of claim 4.

9. A method for alleviating pain in a warm blooded animal which comprises administering to the warm blooded animal suffering pain a compound of formula I in claim 1 in an amount effective to relieve the pain.

10. A method according to claim 9 wherein the compound of formula I in claim 1 is administered in an amount between about 0.5 to 350 mg. per dose in a pharmaceutical carrier.

* * * * *

UNITED STATES PATENT AND TRADEMARK OFFICE
CERTIFICATE OF CORRECTION

PATENT NO. : 4,179,501
DATED : December 18, 1979
INVENTOR(S) : Jacob Szmuszkovicz It is certified that error appears in the above—identified patent and that said Letters Patent is hereby corrected as shown below:

Front Page [54], change Title "Analgesic N-(2-Aminocycloaliphatic-)azidobenzamides"

to --- Analgesic N-(2-Aminocycloaliphatic)-azidobenzamides---.

[57] Abstract: change

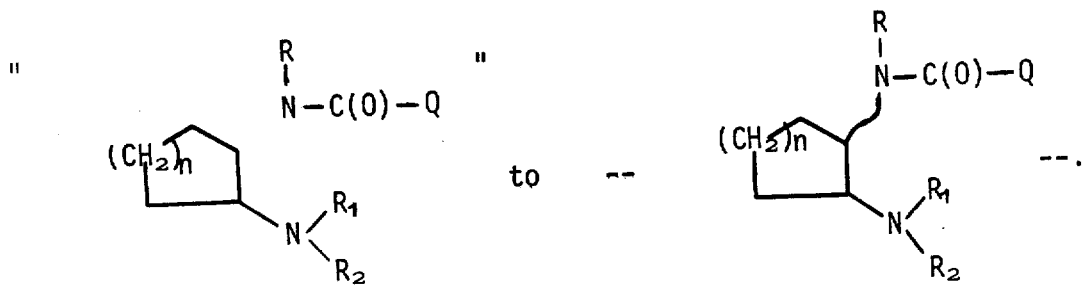

Column 1, line 11: change "naphthaylamides" to --naphthamides--.
Column 5, line 4: change 2-,3-,4- or 5 hexenyl groups" to --2-hexenyl groups--
Column 5, line 49: change ",$C_3$ the remaining" to --, the remaining--.
Column 5, line 50: change "N and Z" to --Y and Z--.
Column 6, line 5: change "$R_2$ to $C_5$-hydroxyalkyl" to --$R_2$ is $C_2$ to $C_5$-hydroxyalkyl--.
Column 6, line 19: change "$C_2$" to --$C_1$--.
Column 9, line 61: change "imdazole" to --imidazole--.
Column 16, line 4: change "morphin" to --morphine--.

UNITED STATES PATENT AND TRADEMARK OFFICE
CERTIFICATE OF CORRECTION

PATENT NO. : 4,179,501
DATED : December 18, 1979
INVENTOR(S) : Jacob Szmuszkovicz It is certified that error appears in the above—identified patent and that said Letters Patent is hereby corrected as shown below:

Column 16, line 48: change "naloxon" to --naloxone--.

Column 19, line 5: change "CDCl$_2$" to --CDCl$_3$--.

Column 21, No. U: change "  " to -- 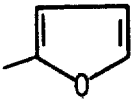 --.

Column 24, line 9: change "CH 1465, CN/other..." to
      --CH 1465, 1440; CN/other--.

Column 24, line 66: change "CdCl$_3$" to --CDCl$_3$--.

Column 25, line 55: change

" 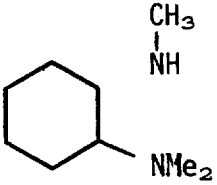 " to -- 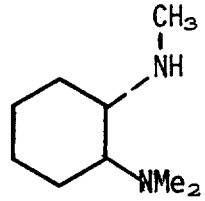 --.

Column 26, line 28: change "N+H/OH≈3000 broad" to --$\overset{+}{N}H$/OH~3000 broad--.

Column 34, line 29: change "peak was 3.4 minutes was..." to
      --peak 3.4 minutes, was....--.

Column 35, line 31: change "(HClO$_4$9...." to --(HClO$_4$).....--.

Column 37, line 38: change "49-90" to --46-90--.

Column 37, line 48: change "N, 12.96" to --N, 12.86--.

Column 37, line 59: change "Me:" to --MeI--.

Column 39, line 7: change "F, 13.13" to --F, 15.13--.

UNITED STATES PATENT AND TRADEMARK OFFICE
CERTIFICATE OF CORRECTION

PATENT NO. : 4,179,501
DATED : December 18, 1979
INVENTOR(S) : Jacob Szmuszkovicz It is certified that error appears in the above—identified patent and that said Letters Patent is hereby corrected as shown below:

Column 50, line 59: change "damine" to --diamine--.

Column 50, line 65: change "C, 840" to --C, 78.40--.

Column 51, line 6: change "$C_{17}H_{25}N_2 \cdot 2...$" to --$C_{17}H_{28}N_2 \cdot 2...$--.

Column 51, line 40: change "Dimethylaminp" to --Dimethylamino--.

Column 52, line 4: change "furmate" to --formate--.

Column 52, line 12: change "$...N_2P...$" to --$N_2O...$--.

Column 52, line 40: change "Anal. Calcd. for $C_{11}H_{24}N_2 1-1/2C_2H_2O_4$

Found: C, 41.15; H, 8.45; N, 8.45"

to      -- Anal. Calcd. for $C_{11}H_{24}N_2 \cdot 1-1/2C_2H_2O_4$

C, 52.66; H, 8.52; N, 8.14

Found: C, 52.26; H, 8.45; N, 8.45 --.

Column 54, line 44, change "diethylamino);cyclohexyl..." to

--diethylamino)cyclohexyl...--.

UNITED STATES PATENT AND TRADEMARK OFFICE
CERTIFICATE OF CORRECTION

PATENT NO. : 4,179,501

DATED : December 18, 1979

INVENTOR(S) : Jacob Szmuszkovicz

It is certified that error appears in the above—identified patent and that said Letters Patent is hereby corrected as shown below:

Column 59, line 28: change "ectylurla" to --ectylurea--.

*Signed and Sealed this*

*Twenty-fourth* Day of *March 1981*

[SEAL]

*Attest:*

RENE D. TEGTMEYER

*Attesting Officer*   *Acting Commissioner of Patents and Trademarks*